United States Patent
Ogawa et al.

(10) Patent No.: US 9,809,545 B2
(45) Date of Patent: Nov. 7, 2017

(54) FACTOR XIA INHIBITORS

(71) Applicant: Merck Sharp & Dohme Corp., Rahway, NJ (US)

(72) Inventors: Anthony Ogawa, New Providence, NJ (US); Scott Edmondson, Clark, NJ (US); Mark Erion, Mountainside, NJ (US); Santhosh Neelamkavil, Edison, NJ (US); Zhuyan Guo, Scotch Plains, NJ (US); Rudrajit Mal, Edison, NJ (US); Jiafang He, South Brunswick, NJ (US); Weiguo Liu, Princeton, NJ (US); Ellen K. Vande Bunte, Hawthorne, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/778,765

(22) PCT Filed: Mar. 21, 2014

(86) PCT No.: PCT/US2014/031388
§ 371 (c)(1),
(2) Date: Sep. 21, 2015

(87) PCT Pub. No.: WO2014/160592
PCT Pub. Date: Oct. 2, 2014

(65) Prior Publication Data
US 2016/0046581 A1   Feb. 18, 2016

Related U.S. Application Data

(60) Provisional application No. 61/805,733, filed on Mar. 27, 2013.

(51) Int. Cl.
| | |
|---|---|
| *C07D 401/14* | (2006.01) |
| *C07D 213/64* | (2006.01) |
| *A61K 31/551* | (2006.01) |
| *C07D 401/04* | (2006.01) |
| *C07D 405/14* | (2006.01) |
| *C07D 413/14* | (2006.01) |
| *C07D 401/06* | (2006.01) |
| *C07D 401/10* | (2006.01) |
| *C07D 401/12* | (2006.01) |
| *C07D 405/12* | (2006.01) |
| *C07D 413/06* | (2006.01) |
| *C07D 413/12* | (2006.01) |
| *C07D 471/04* | (2006.01) |
| *C07D 471/10* | (2006.01) |
| *C07D 487/04* | (2006.01) |
| *C07D 487/10* | (2006.01) |
| *C07D 491/044* | (2006.01) |
| *C07D 491/052* | (2006.01) |
| *C07F 9/6558* | (2006.01) |

(52) U.S. Cl.
CPC .......... *C07D 213/64* (2013.01); *A61K 31/551* (2013.01); *C07D 401/04* (2013.01); *C07D 401/06* (2013.01); *C07D 401/10* (2013.01); *C07D 401/12* (2013.01); *C07D 401/14* (2013.01); *C07D 405/12* (2013.01); *C07D 405/14* (2013.01); *C07D 413/06* (2013.01); *C07D 413/12* (2013.01); *C07D 413/14* (2013.01); *C07D 471/04* (2013.01); *C07D 471/10* (2013.01); *C07D 487/04* (2013.01); *C07D 487/10* (2013.01); *C07D 491/044* (2013.01); *C07D 491/052* (2013.01); *C07F 9/65583* (2013.01)

(58) Field of Classification Search
CPC . C07D 401/14; C07F 9/65583; C07F 9/66583
USPC .......................... 546/24, 268.4; 514/80, 338
See application file for complete search history.

(56) References Cited

U.S. PATENT DOCUMENTS

| 8,093,392 B2 | 1/2012 | Golec et al. |
| 8,163,779 B2 | 4/2012 | Cheruvallath et al. |
| 2007/0037822 A1 | 2/2007 | Letourneau et al. |

(Continued)

FOREIGN PATENT DOCUMENTS

| EP | 1847537 A1 | 10/2007 |
| WO | 2013022818 A1 | 2/2013 |

(Continued)

OTHER PUBLICATIONS

Courtney et al., "Pyridinone and, etc.," CA 159:181751 (2013).*

(Continued)

*Primary Examiner* — Patricia L Morris
(74) *Attorney, Agent, or Firm* — Nicole M. Beeler; Catherine D. Fitch

(57) ABSTRACT

The present invention provides a compound of Formula (I)

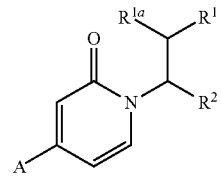

and pharmaceutical compositions comprising one or more said compounds, and methods for using said compounds for treating or preventing thromboses, embolisms, hypercoagu-ability or fibrotic changes.

7 Claims, No Drawings

(56) References Cited

U.S. PATENT DOCUMENTS

2011/0130365 A1 6/2011 Benbow et al.

FOREIGN PATENT DOCUMENTS

| WO | WO2013022814 A1 | 2/2013 |
| WO | WO2013093484 A1 | 6/2013 |

OTHER PUBLICATIONS

International Search Report and Written Opinion for PCT/US2014/031388, dated Oct. 28, 2014, 11 pages.
Extended European Search Report for 14776100.1, dated Sep. 2, 2016, 5 pages.

* cited by examiner

FACTOR XIa INHIBITORS

CROSS REFERENCE TO RELATED APPLICATIONS

This application is a U.S. National Phase application under 35 U.S.C. §371 of PCT Application No. PCT/US14/031388 filed Mar. 21, 2014, which claims priority from U.S. Provisional Application Ser. No. 61/805,733, filed Mar. 27, 2013.

BACKGROUND OF THE INVENTION

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commences after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. Clotting factor IX can be activated by means of the intrinsic pathway and the extrinsic pathway. The activation of factor XIa is thus a central point of intersection between the two pathways of activation of clotting. Factor XIa has an important role in blood clotting.

WO2013022814 describes macrocyclic Factor XIa inhibitors.

SUMMARY OF THE INVENTION

The invention includes compounds for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compounds may optionally include anticoagulants, antiplatelet agents, and thrombolytic agents. The compounds can be added to blood, blood products, or mammalian organs in order to effect the desired inhibitions.

The invention also includes a compound for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compounds may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

Compounds of the invention are Factor XIa inhibitors and may have therapeutic value in, for example, preventing coronary artery disease.

The invention includes compounds of formula I

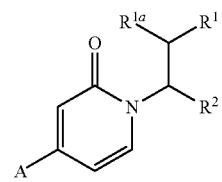

and pharmaceutically acceptable salts thereof, where
A is
1) 6-membered monocyclic carbocycle unsubstituted or mono-substituted with $R^3$ or di-substituted with $R^3$ and $R^4$,
2) 5 or 6 membered monocyclic heterocycle having 1 or 2 N atoms and unsubstituted or mono-substituted with $R^3$ or di-substituted with $R^3$ and $R^4$,
3) 10-membered bicyclic carbocycle unsubstituted or substituted with $R^3$, or
4) 10-membered bicyclic unsubstituted heterocycle having 1 N atom and unsubstituted or substituted with $R^3$;
$R^1$ is
1) $C_{1-6}$ alkyl,
2) 6-membered monocyclic carbocycle unsubstituted or substituted with $R^7$, or
3) 5- or 6-membered monocyclic heterocycle having one, two or three heteroatoms, wherein the heteroatoms are selected from the group of 1-2 N atoms and 1 O atom, and unsubstituted or mono-substituted with $R^3$ or di-substituted with $R^3$ and $R^4$;
$R^{1a}$ is H or $CH_3$;
$R^2$ is
1) $-C(O)NHR^8$,
2) $-C(O)N(CH_2R^8)(CH_2R^{10})$,
3) $-C(O)R^{11}$,
4) 5-membered heterocycle having 1-3 heteroatoms and unsubstituted or substituted with $R^{16}$, $R^{17}$ or $R^{18}$;
5) 9-membered bicyclic heterocycle having 1-3 heteroatoms and unsubstituted or substituted with $R^{16}$, $R^{17}$ or $R^{18}$; or 6) 13 or 14-membered tricyclic heterocycle having 1-3 heteroatoms and unsubstituted or substituted with $R^{16}$, $R^{17}$ or $R^{18}$;

$R^3$ and $R^4$ are each independently
1) —C(NH)$NH_2$,
2) —$NH_2$,
3) Halogen,
4) —$C_{1-6}$ alkyl, unsubstituted or substituted with OH, F or $NH_2$;
5) —C(O)O$C_{1-6}$ alkyl,
6) —$CF_3$,
7) 5-membered heterocycle with 1-4 N atoms which is unsubstituted or mono-substituted with $R^5$ or di-substituted with $R^5$ and $R^6$,
8) —$NO_2$,
9) —CN, or
10) —O$C_{1-6}$ alkyl;

$R^5$ and $R^6$ are each independently selected from unsubstituted $C_{1-6}$ alkyl or $C_{1-6}$ alkyl substituted with F;

$R^7$ is halogen, —$CF_3$ or $OCF_3$;

$R^8$ is
1) 6-membered monocyclic carbocycle substituted with $R^{12}$,
2) 9-membered bicyclic heterocycle having 2 or 3 heteroatoms and unsubstituted or substituted with =O or $CF_3$, or
3) 6-membered heteroaryl having 1 or 2 N atoms and unsubstituted or substituted with $R^{12}$;

$R^{10}$ is
1) 4-6-membered carbocycle either unsubstituted or substituted with —NHC(O)OH, or
2) $C_{1-6}$ alkyl unsubstituted or substituted with a 9-membered heterocycle having 1 N atom;

$R^1$ is
1) 5-7-membered monocyclic heterocycle, having 1 or 2 N atoms, said heterocycle mono-substituted with $R^{13}$ or di-substituted with $R^{13}$ and $R^{14}$,
2) 8-10-membered bicyclic heterocycle, having 2 or 3 N atoms, said heterocycle substituted with $R^{13}$, or
3) 13-membered tricyclic heterocycle, having 2 or 3 N atoms, said heterocycle substituted with $R^{13}$;

$R^{12}$ is —C(O)OH, —C(O)O$C_{1-6}$ alkyl, —NHC(O)O$C_{1-6}$ alkyl, halogen, —$SO_2C_{1-6}$ alkyl, —P(O)(O$C_{1-6}$ alkyl)(O$C_{1-6}$ alkyl), —P(O)(OH)$_2$ or 5-membered unsubstituted heterocycle having 1-4 N atoms;

$R^{13}$ is
1) C(O)O$C_{1-6}$ alkyl,
2) $C_{1-6}$ alkyl unsubstituted or mono- or bi-substituted with a group selected from OH, —$CHF_2$, 5-membered monocyclic heterocycle having 1 N atom, 9-membered bicyclic heterocycle having 1 or 2 N atoms,
3) 5 or 6-membered saturated or unsaturated heterocycle unsubstituted or substituted with —OH, or
4) 6-membered unsaturated carbocycle unsubstituted or substituted with $R^{15}$;

$R^{14}$ is $C_{1-6}$ alkyl unsubstituted or substituted with —OH, —$C_6H_5$, or —((CH$_2$)$_n$—O)$_m$—$CH_3$, where m is 1 or 2 and n is 1 or 2;

$R^{15}$ is —O$C_{1-6}$ alkyl or —N($C_{1-6}$ alkyl)($C_{1-6}$alkyl);

$R^{16}$ is and $R^{17}$ are each independently
1) 6-membered carbocycle unsubstituted or substituted with $R^{20}$, or
2) 6-membered heterocycle having 1 or 2 N atoms unsubstituted or substituted with $R^{20}$,
3) 6-membered carbocycle unsubstituted or substituted with $R^{19}$, or
4) 6-membered heterocycle having 1 or 2 N atoms unsubstituted or substituted with $R^{19}$;

$R^{18}$ is
1) —C(O)O$C_{1-6}$ alkyl,
2) —C(O)OH,
3) halogen,
4) —P(O)(O$C_{1-6}$ alkyl)(O$C_{1-6}$ alkyl),
5) —P(O)(OH)$_2$,
6) —$SO_2C_{1-6}$ alkyl,
7) —CN,
8) —$CF_3$,
9) —C(O)NH$R^{10}$
10) —NHC(O)O$R^{14}$
11) —NHC(O)$R^{10}$, or
12) —P(O)(NH$C_{1-6}$ alkyl)(NH$C_{1-6}$ alkyl);

$R^{19}$ and $R^{20}$ are each independently
1) halogen,
2) —$SO_2C_{1-6}$ alkyl,
3) —$CF_3$,
4) —CN,
5) —O$C_{1-6}$ alkyl,
6) —$OCF_3$,
7) —$C_{1-6}$ alkyl,
8) —C(O)NH$R^{10}$
9) —NHC(O)$R^{10}$
10) —P(O)(OH)$_2$,
11) —P(O)(O$C_{1-6}$ alkyl)(O$C_{1-6}$ alkyl), and
12) —P(O)(NH$C_{1-6}$ alkyl)(NH$C_{1-6}$ alkyl).

In one embodiment, the invention includes compounds of formula I and pharmaceutically acceptable salts thereof, where A is
1) 6-membered monocyclic carbocycle unsubstituted or mono-substituted with $R^3$ or di-substituted with $R^3$ and $R^4$,
2) 5 or 6 membered monocyclic heterocycle having 1 or 2 N atoms and unsubstituted or mono-substituted with $R^3$ or di-substituted with $R^3$ and $R^4$,
3) 10-membered bicyclic carbocycle unsubstituted or substituted with $R^3$, or
4) 10-membered bicyclic unsubstituted heterocycle having 1 N atom and unsubstituted or substituted with $R^3$;

$R^1$ is
1) $C_{1-6}$ alkyl,
2) 6-membered monocyclic carbocycle unsubstituted or substituted with $R^7$, or
3) 5- or 6-membered monocyclic heterocycle having one, two or three heteroatoms, wherein the heteroatoms are selected from the group of 1-2 N atoms and 1 O atom, and unsubstituted or mono-substituted with $R^3$ or di-substituted with $R^3$ and $R^4$;

$R^{1a}$ is H or $CH_3$;

$R^2$ is
1) —C(O)NH$R^8$,
2) —C(O)N(CH$_2$R)(CH$_2R^{10}$),
3) —C(O)$R^{11}$,
4) 5-membered heterocycle having 1-3 heteroatoms and unsubstituted or substituted with $R^{18}$;
5) 9-membered bicyclic heterocycle having 1-3 heteroatoms and unsubstituted or substituted with $R^{18}$; or
6) 13 or 14-membered tricyclic heterocycle having 1-3 heteroatoms and unsubstituted or substituted with $R^{18}$;

$R^3$ and $R^4$ are each independently
1) —C(NH)$NH_2$,
2) —$NH_2$,
3) Halogen,

4) —$C_{1-6}$ alkyl, unsubstituted or substituted with —OH, F or —$NH_2$,
5) —C(O)O$C_{1-6}$ alkyl,
6) —$CF_3$,
7) 5-membered heterocycle with 1-4 N atoms which is unsubstituted or mono-substituted with $R^5$ or di-substituted with $R^5$ and $R^6$,
8) —$NO_2$,
9) —CN, or
10) —O$C_{1-6}$ alkyl;

$R^5$ and $R^6$ are each independently selected from unsubstituted $C_{1-6}$ alkyl or $C_{1-6}$ alkyl substituted with F;

$R^7$ is halogen, —$CF_3$ or —$OCF_3$;

$R^8$ is
1) 6-membered monocyclic carbocycle substituted with $R^{12}$,
2) 9-membered bicyclic heterocycle having 2 or 3 heteroatoms and unsubstituted or substituted with =O or $CF_3$, or
3) 6-membered heteroaryl having 1 or 2 N atoms and unsubstituted or substituted with $R^{12}$;

$R^{10}$ is
1) 4-6-membered carbocycle either unsubstituted or substituted with —NHC(O)OH, or
2) $C_{1-6}$ alkyl unsubstituted or substituted with a 9-membered heterocycle having 1 N atom;

$R^{11}$ is
1) 5-7-membered monocyclic heterocycle, having 1 or 2 N atoms, said heterocycle mono-substituted with $R^{13}$ or di-substituted with $R^{13}$ and $R^{14}$,
2) 8-10-membered bicyclic heterocycle, having 2 or 3 N atoms, said heterocycle substituted with $R^{13}$, or
3) 13-membered tricyclic heterocycle, having 2 or 3 N atoms, said heterocycle substituted with $R^{13}$;

$R^{12}$ is —C(O)OH, —C(O)O$C_{1-6}$ alkyl, —NHC(O)O$C_{1-6}$ alkyl, halogen, —$SO_2C_{1-6}$ alkyl, —P(O)(O$C_{1-6}$ alkyl)(O$C_{1-6}$ alkyl), —P(O)(OH)$_2$ or 5-membered unsubstituted heterocycle having 1-4 N atoms;

$R^{13}$ is
1) C(O)O$C_{1-6}$ alkyl,
2) $C_{1-6}$ alkyl unsubstituted or mono- or bi-substituted with a group selected from OH, —$CHF_2$, 5-membered monocyclic heterocycle having 1 N atom, 9-membered bicyclic heterocycle having 1 or 2 N atoms,
3) 5 or 6 membered saturated or unsaturated heterocycle unsubstituted or substituted with —OH, or
4) 6-membered unsaturated carbocycle unsubstituted or substituted with $R^{15}$;

$R^{14}$ is $C_{1-6}$ alkyl unsubstituted or substituted with —OH, —$C_6H_5$, or —(($CH_2)_n$—O)$_m$—$CH_3$, where m is 1 or 2 and n is 1 or 2;

$R^{15}$ is —O$C_{1-6}$ alkyl or —N($C_{1-6}$ alkyl)($C_{1-6}$alkyl);

$R^{18}$ is
1) —C(O)O$C_{1-6}$ alkyl,
2) —C(O)OH,
3) halogen,
4) —P(O)(O$C_{1-6}$ alkyl)(O$C_{1-6}$ alkyl),
5) —P(O)(OH)$_2$,
6) —$SO_2C_{1-6}$ alkyl,
7) —CN,
8) —$CF_3$,
9) —C(O)NH$R^{10}$
10) —NHC(O)O$R^{14}$
11) —NHC(O)$R^{10}$, or
12) —P(O)(NH$C_{1-6}$ alkyl)(NH$C_{1-6}$ alkyl);

$R^{19}$ and $R^{20}$ are each independently
1) halogen,
2) —$SO_2C_{1-6}$ alkyl,
3) —$CF_3$,
4) —CN,
5) —O$C_{1-6}$ alkyl,
6) —$OCF_3$,
7) —$C_{1-6}$ alkyl,
8) —C(O)NH$R^{10}$,
9) —NHC(O)$R^{10}$
10) —P(O)(OH)$_2$,
11) —P(O)(O$C_{1-6}$ alkyl)(O$C_{1-6}$ alkyl), and
12) —P(O)(NH$C_{1-6}$ alkyl)(NH$C_{1-6}$ alkyl).

Another embodiment of the invention includes compounds of formula Ia

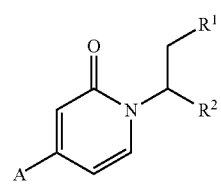

or a pharmaceutically acceptable salt thereof, where

A is
1) 6-membered monocyclic carbocycle unsubstituted or mono-substituted with $R^3$ or di-substituted with $R^3$ and $R^4$,
2) 5 or 6 membered monocyclic heterocycle having 1 or 2 N atoms and unsubstituted or mono-substituted with $R^3$ or di-substituted with $R^3$ and $R^4$,
3) 10-membered bicyclic carbocycle unsubstituted or substituted with $R^3$, or 4) 10-membered bicyclic unsubstituted heterocycle having 1 N atom and unsubstituted or substituted with $R^3$;

$R^1$ is
1) $C_{1-6}$ alkyl,
2) 6-membered monocyclic carbocycle unsubstituted or substituted with $R^7$, or 3) 5- or 6-membered monocyclic heterocycle having one, two or three heteroatoms, wherein the heteroatoms are selected from the group of 1-2 N atoms and 1 O atom, and unsubstituted or mono-substituted with $R^3$ or di-substituted with $R^3$ and $R^4$;

$R^2$ is
1) —C(O)NH$R^8$,
2) —C(O)N(CH$_2$R)(CH$_2R^{10}$),
3) —C(O)$R^{11}$,
4) 5-membered heterocycle having 1-3 heteroatoms and unsubstituted or substituted with $R^{18}$;
5) 9-membered bicyclic heterocycle having 1-3 heteroatoms and unsubstituted or substituted with $R^{18}$; or
6) 13 or 14-membered tricyclic heterocycle having 1-3 heteroatoms and unsubstituted or substituted with $R^{18}$;

$R^3$ is
1) —C(NH)NH$_2$,
2) NH$_2$,
3) Halogen,
4) $C_{1-6}$ alkyl, unsubstituted or substituted with —OH, F, —NH$_2$,
5) C(O)O$C_{1-6}$alkyl,
6) $CF_3$, or
7) 5-membered heterocycle with 1-4 N atoms which is unsubstituted or mono-substituted with $R^5$ or di-substituted with $R^5$ and $R^6$;

R[4] is —NO$_2$, C$_{1-6}$ alkyl, —CN, —NH$_2$, —OC$_{1-6}$ alkyl, or 5-membered unsubstituted heterocycle with 1-4 N atoms;
R[5] and R[6] are each independently selected from unsubstituted C$_{1-6}$ alkyl or C$_{1-6}$ alkyl substituted with F;
R[7] is halogen, —CF$_3$ or —OCF$_3$;
R[8] is
  1) 6-membered monocyclic carbocycle substituted with R[12], or
  2) 9-membered bicyclic heterocycle having 2 or 3 heteroatoms and unsubstituted or substituted with =O or CF$_3$;
R[10] is
  1) 4-6-membered carbocycle either unsubstituted or substituted with —NHC(O)OH, or
  2) C$_{1-6}$ alkyl unsubstituted or substituted with a 9-membered heterocycle having 1 N atom;
R[11] is
  1) 5-7-membered monocyclic heterocycle, having 1 or 2 N atoms, said heterocycle mono-substituted with R[13] or di-substituted with R[13] and R[14],
  2) 8-10-membered bicyclic heterocycle, having 2 or 3 N atoms, said heterocycle substituted with R[13], or
  3) 13-membered tricyclic heterocycle, having 2 or 3 N atoms, said heterocycle substituted with R[13];
R[12] is —C(O)OH, —C(O)OC$_{1-6}$ alkyl, —NHC(O)OC$_{1-6}$ alkyl, halogen, —SO$_2$C$_{1-6}$ alkyl, —P(O)(OC$_{1-6}$ alkyl)(OC$_{1-6}$ alkyl), —P(O)(OH)$_2$ or 5-membered unsubstituted heterocycle having 1-4 N atoms;
R[13] is
  1) C(O)OC$_{1-6}$ alkyl,
  2) C$_{1-6}$ alkyl unsubstituted or mono- or bi-substituted with a group selected from OH, —CHF$_2$, 5-membered monocyclic heterocycle having 1 N atom, 9-membered bicyclic heterocycle having 1 or 2 N atoms,
  3) 5 or 6-membered saturated or unsaturated heterocycle unsubstituted or substituted with —OH, or
  4) 6-membered unsaturated carbocycle unsubstituted or substituted with R[15];
R[14] is C$_{1-6}$ alkyl unsubstituted or substituted with —OH, —C$_6$H$_5$, or —((CH$_2$)$_n$—O)$_m$—CH$_3$, where m is 1 or 2 and n is 1 or 2;
R[15] is —OC$_{1-6}$ alkyl or —N(C$_{1-6}$ alkyl)(C$_{1-6}$alkyl);
R[18] is
  1) —C(O)OC$_{1-6}$ alkyl,
  2) —C(O)OH,
  3) halogen,
  4) —P(O)(OC$_{1-6}$ alkyl)(OC$_{1-6}$ alkyl),
  5) —P(O)(OH)$_2$,
  6) —SO$_2$C$_{1-6}$ alkyl,
  7) —CN,
  8) —CF$_3$,
  9) —C(O)NHR[10],
  10) —NHC(O)OR[14],
  11) —NHC(O)R[10], or
  12) —P(O)(NHC$_{1-6}$ alkyl)(NHC$_{1-6}$ alkyl);
R[19] and R[20] are independently
  1) halogen,
  2) —SO$_2$C$_{1-6}$ alkyl,
  3) —CF$_3$,
  4) —CN,
  5) —OC$_{1-6}$ alkyl,
  6) —OCF$_3$,
  7) —C$_{1-6}$ alkyl,
  8) —C(O)NHR[10],
  9) —NHC(O)R[10],
  10) —P(O)(OH)$_2$,
  11) —P(O)(OC$_{1-6}$ alkyl)(OC$_{1-6}$ alkyl), and
  12) —P(O)(NHC$_{1-6}$ alkyl)(NHC$_{1-6}$ alkyl).

In another embodiment, the invention includes compounds of formula Ia:

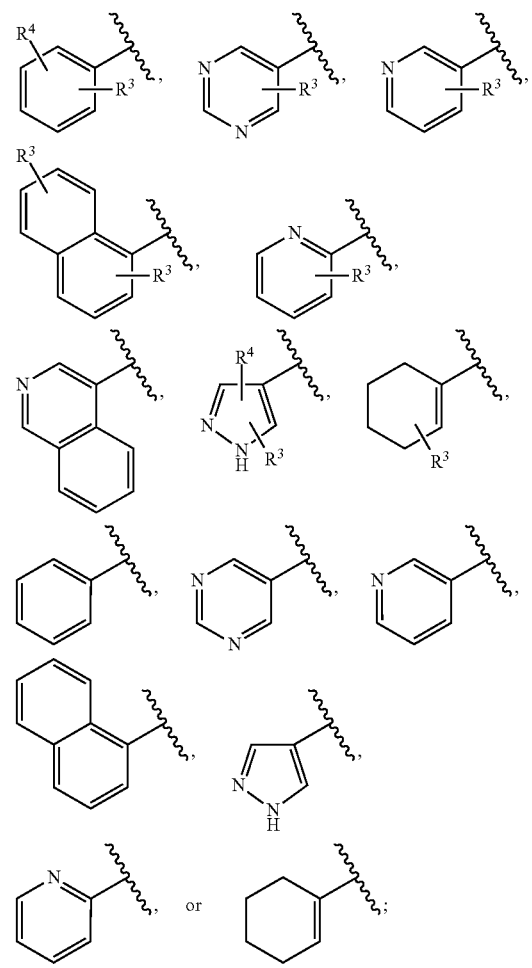

and pharmaceutically acceptable salts thereof, where A is

R[1] is
  —C$_{1-6}$alkyl,

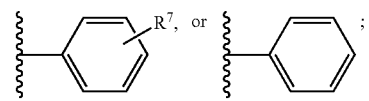

$R^2$ is
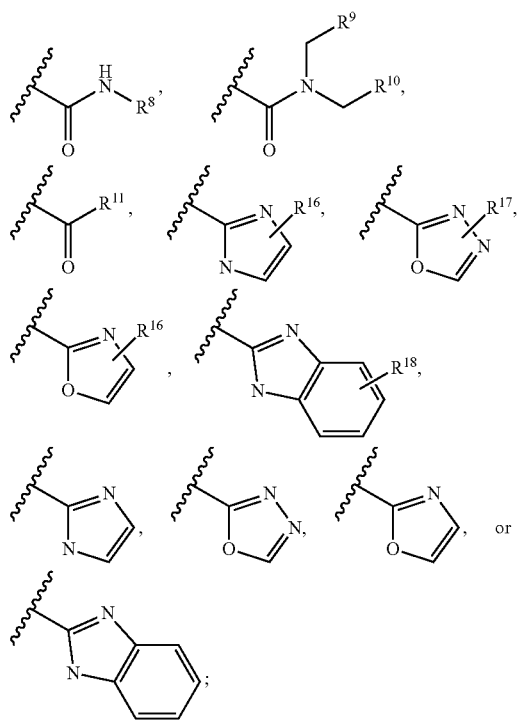
$R^3$ is
—C(NH)NH$_2$, NH$_2$, —Cl, —CH(CH$_3$)OH, —CH$_3$, —C(O)OCH$_2$CH$_3$, —OF$_3$,
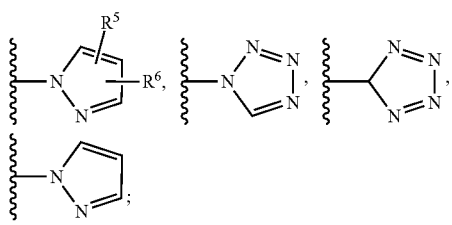
$R^4$ is
—NO$_2$, —CH$_3$, —CN, —NH$_2$, —OCH$_3$, or
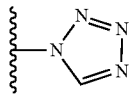
$R^5$ and $R^6$ are independently selected from —CH$_3$;
$R^7$ is —Cl, F, or —OCF$_3$;
$R^8$ is
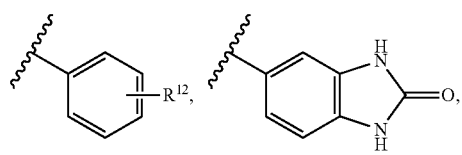
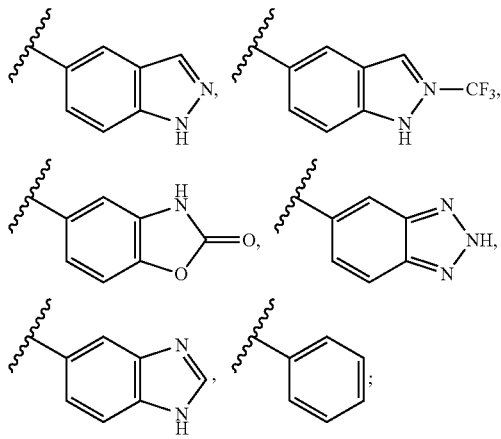
$R^9$ is
—CH$_2$OH or
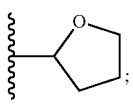 [SMILES: *C1CCCO1 ; ";"]
$R^{10}$ is
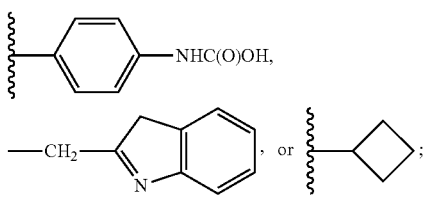
$R^{11}$ is
—OH, —C(O)OC(CH$_3$)$_3$, —CH(OH)CHF$_2$, —CH(CH$_3$)$_2$,
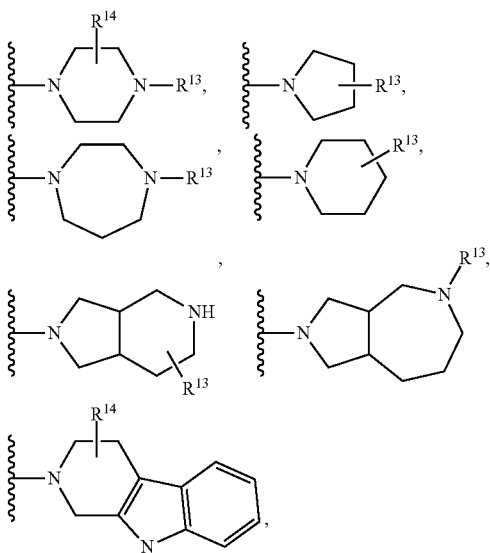

-continued

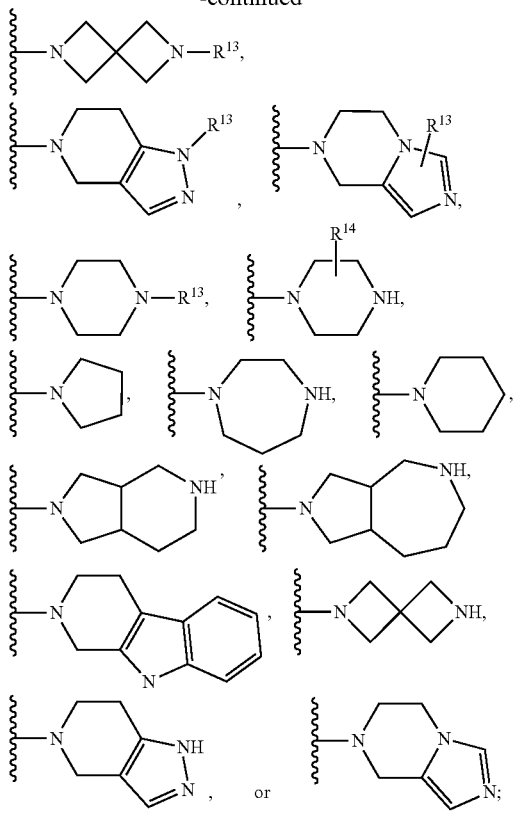

$R^{12}$ is —C(O)OH, —C(O)OC(CH$_3$)$_3$, —NHC(O)OCH$_3$, —NHC(O)OCH$_2$CH$_3$, F or

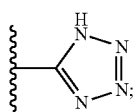

$R^{13}$ is —C(O)OC(CH$_3$)$_3$, —CH(OH)CHF$_2$, —CH(CH$_3$)$_2$,

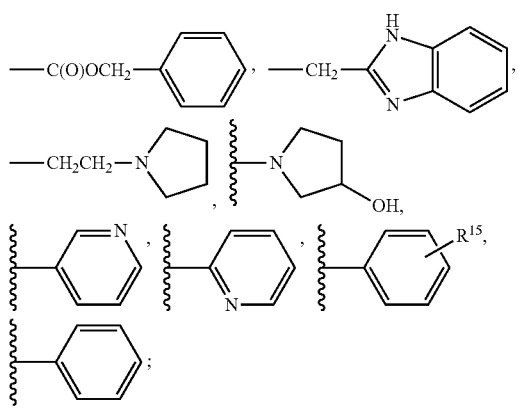

$R^{14}$ is —CH$_2$OH or —CH$_2$C$_6$H$_5$;
$R^{15}$ is —OCH$_3$, or —N(CH$_3$)$_2$;
$R^{18}$ is —C(O)OCH$_3$, —C(O)OCH$_2$CH$_3$, —C(O)OH, —F, —P(O)(OCH$_2$CH$_3$)$_2$, —P(O)(OH)$_2$, —C(O)OC(CH$_3$)$_3$, —CN or —P(O)(NHC$_{1-6}$ alkyl)(NHC$_{1-6}$ alkyl);

$R^{19}$ is —C(O)OH, F, Cl, —OCF$_3$, —P(O)(OH)$_2$ or P(O)(NHC$_{1-6}$ alkyl)(NHC$_{1-6}$ alkyl);
$R^{20}$ is, —F, —SO$_2$CH$_3$, —Cl, —CF$_3$, —CN, —OCH$_3$, —OCF$_3$, or —CH$_3$.

In another embodiment of the invention,
A is

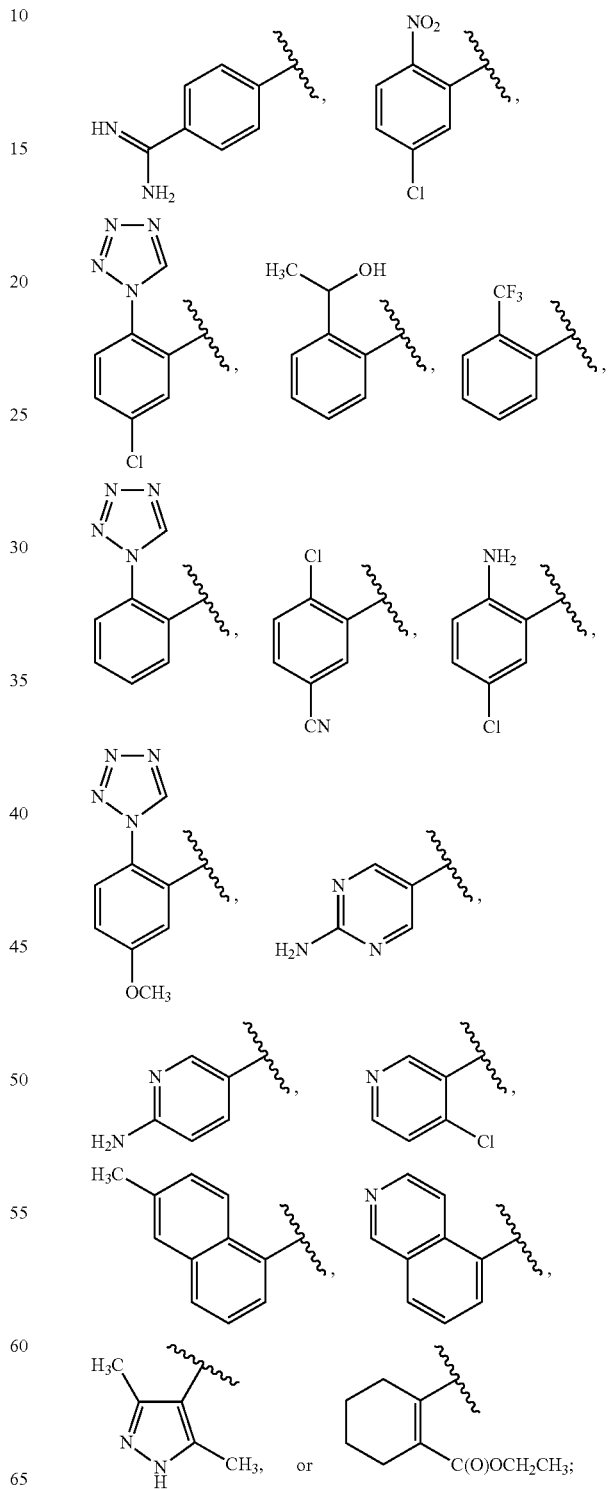

R¹ is
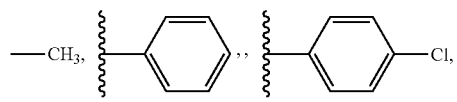 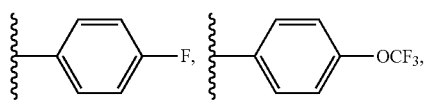 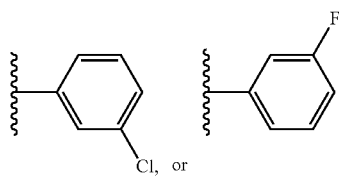;
R² is
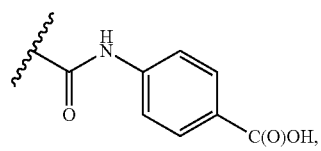
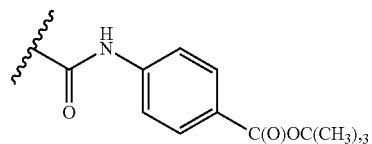
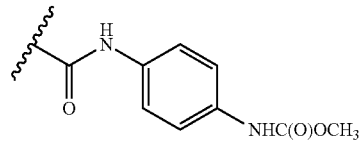
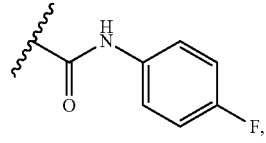
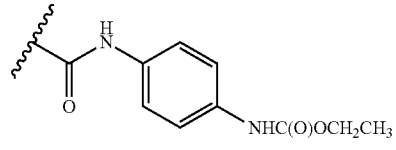
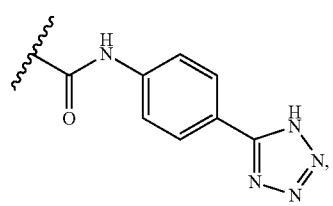
-continued
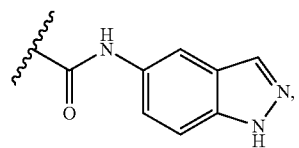
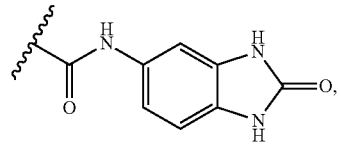
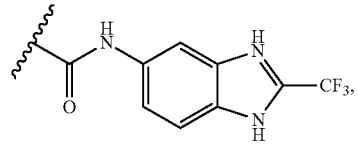
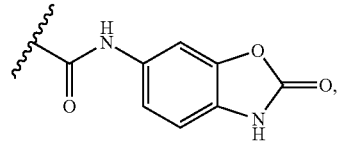
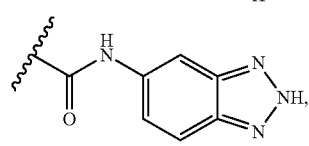
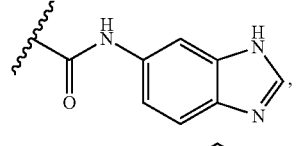
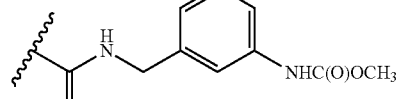
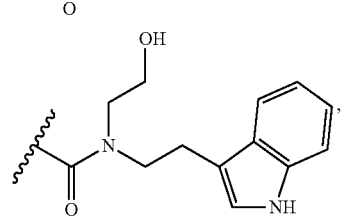
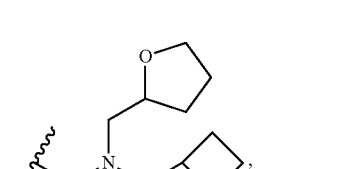
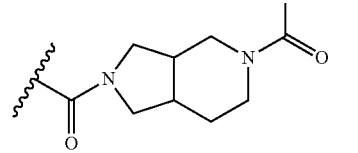

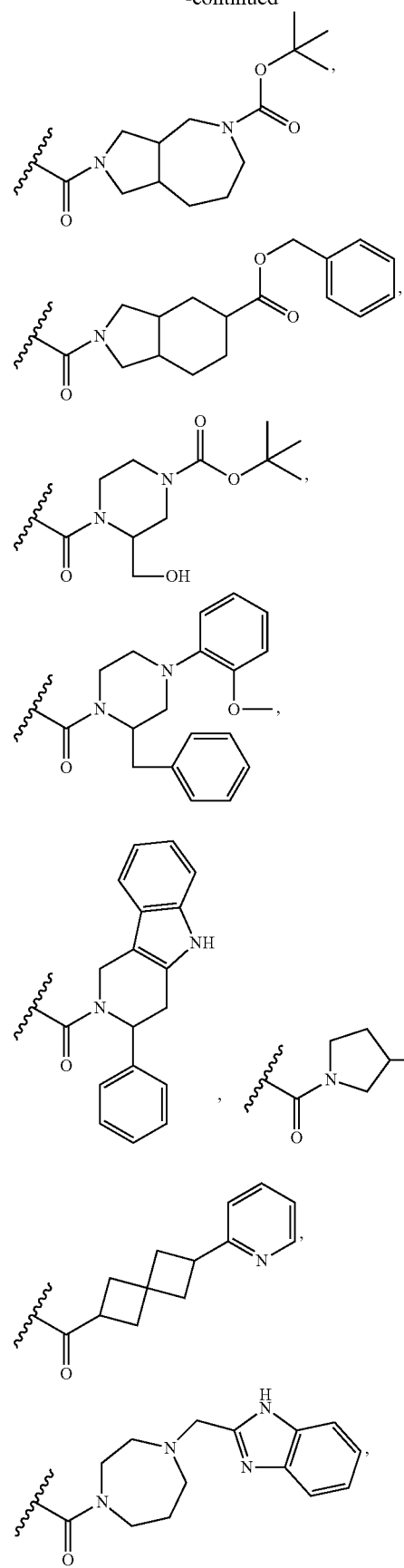
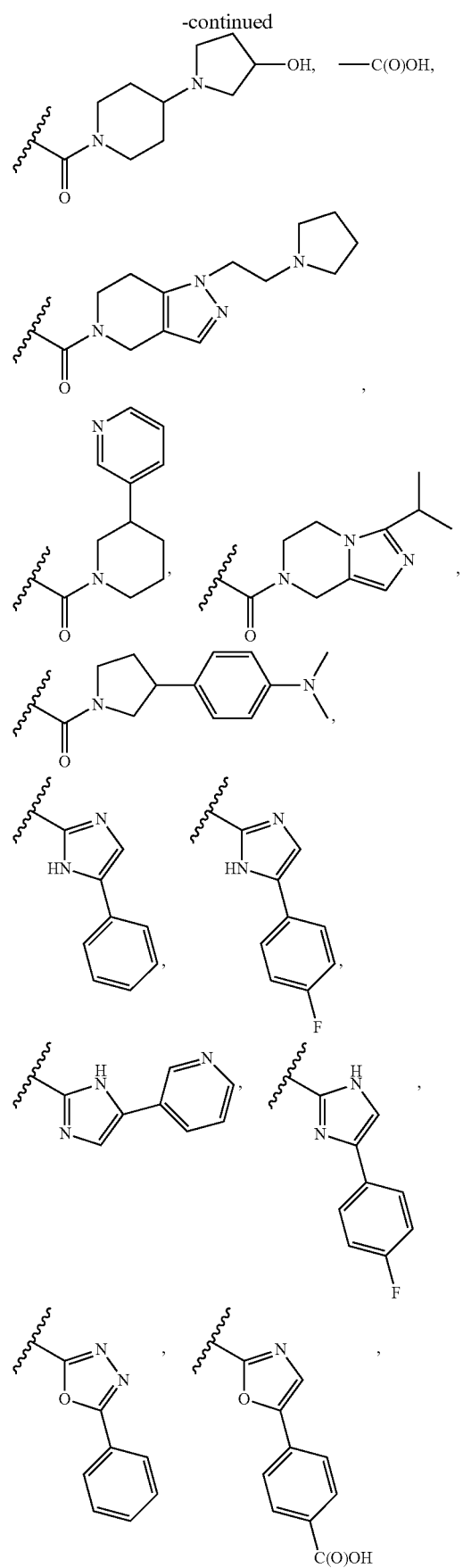

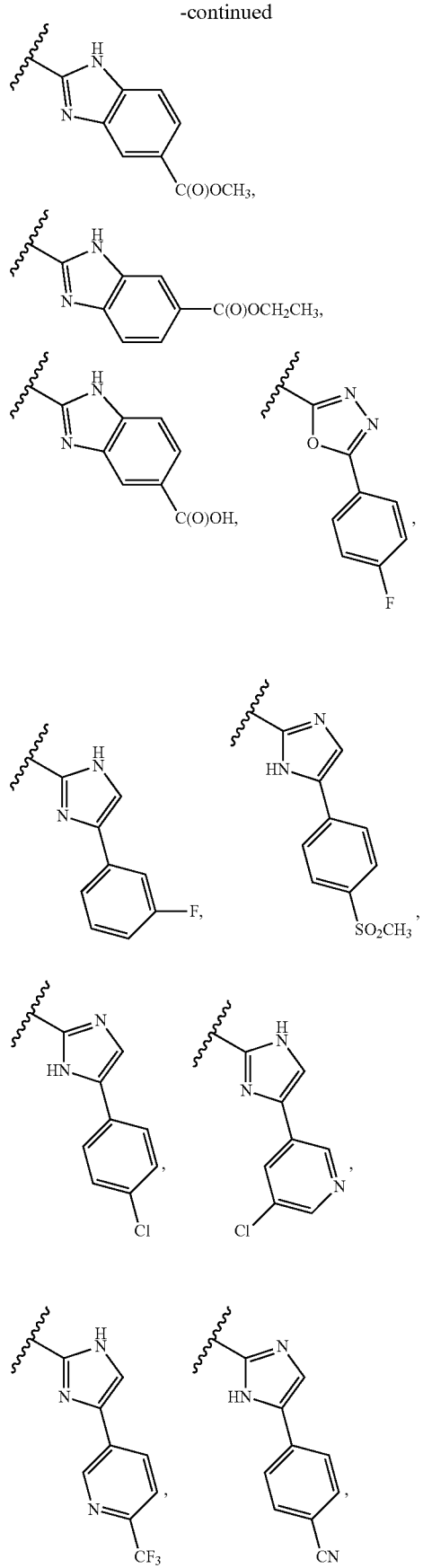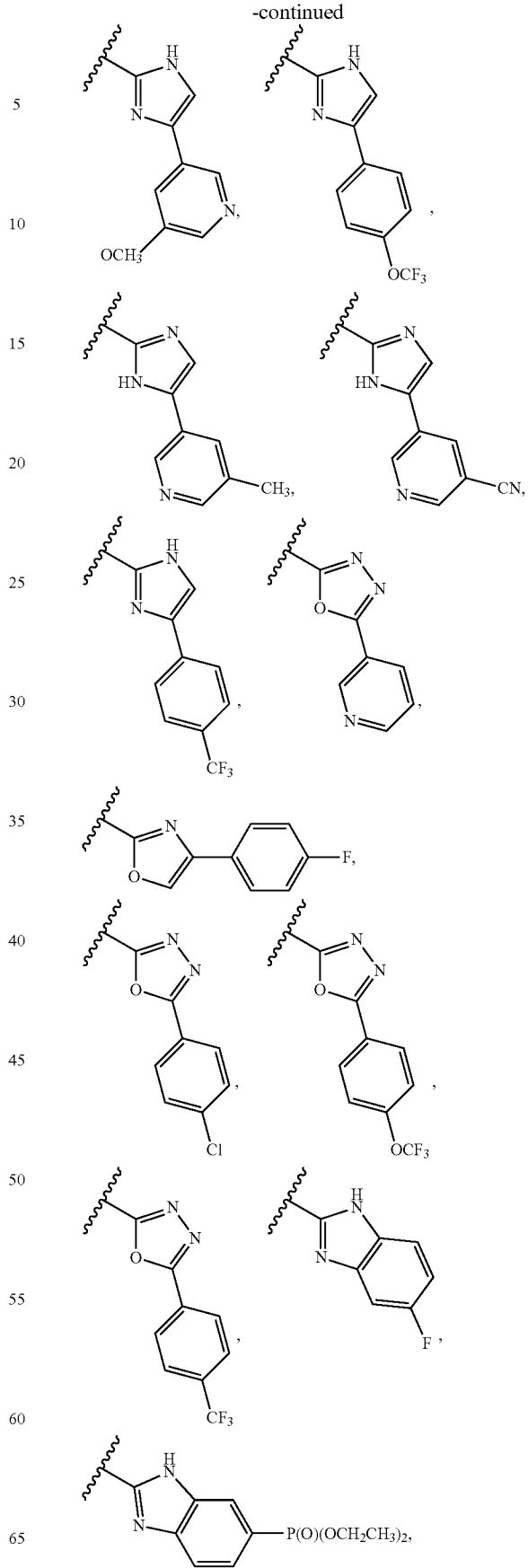

-continued

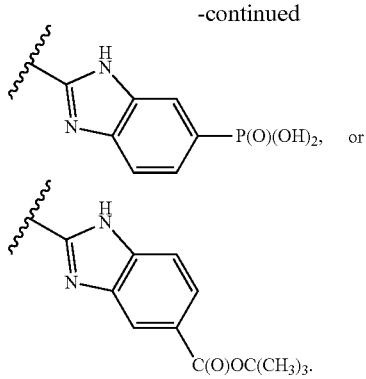

In another embodiment of the invention, $R^{16}$ is

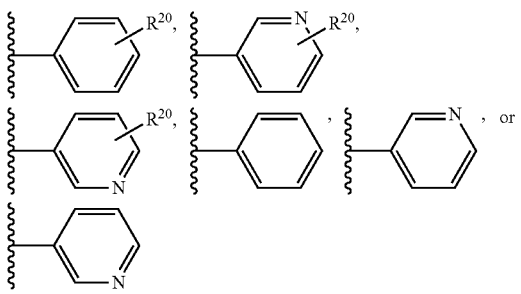

In another embodiment of the invention, $R^{17}$ is

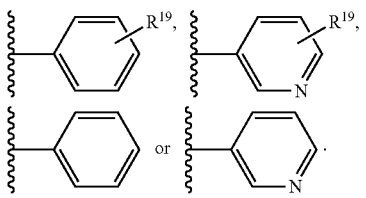

In another embodiment of the invention, the compounds are those prepared in Examples 1-7.

It will be understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, diglu-conate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis.

Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Reference to the compounds of this invention as those of a specific formula or embodiment, e.g., Formula I or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

Except where noted herein, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or $CH_3$ or a symbol that is an extended bond as the terminal group, e.g.

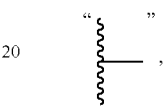

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. For example, the structures

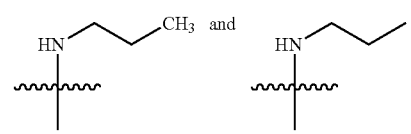

have equivalent meanings. $C_{1-4}$ alkyl includes n-, iso-, sec- and t-butyl, n- and isopropyl, ethyl and methyl. If no number is specified, 1-4 carbon atoms are intended for linear or branched alkyl groups.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically acceptable salts.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

When any variable occurs more than one time in any constituent or in formula I, its definition on each occurrence is independent of its definition at every other occurrence. Also, combinations of substituents and/or variables are permissible only if such combinations result in stable compounds.

Except where noted herein, "alkanol" is intended to include aliphatic alcohols having the specified number of carbon atoms, such as methanol, ethanol, propanol, etc., where the —OH group is attached at any aliphatic carbon, e.g., propan-1-ol, propan-2-ol, etc.

Except where noted herein, alkyl groups may be unsubstituted, or substituted with 1 to 3 substituents on any one or more carbon atoms, with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, HS(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)C(O)NH—, $H_2$N—C(NH)—, —O($C_1$-$C_6$ alkyl)$CF_3$, HC(O)—, ($C_1$-$C_6$ alkyl)C(O)—, HOC(O)—, ($C_1$-$C_6$ alkyl)OC(O)—, HO($C_1$-$C_6$ alkyl)-, ($C_1$-$C_6$ alkyl)O($C_1$-$C_6$ alkyl)-, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$—, HOC(O)NH—, ($C_1$-$C_6$ alkyl)OC(O)NH—, aryl, aralkyl, heterocycle, heterocyclyl-alkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

Except where noted, the term "halogen" means fluorine, chlorine, bromine or iodine.

Except where noted, the term "heterocycle" refers to a stable 4- to 7-membered mono-cyclic or stable 7- to 12-membered bicyclic or stable 12- to 14-membered tricyclic heteroatom-containing ring system unsubstituted or substituted with $C_1$-4 alkyl or halogen, any ring of which may be saturated or unsaturated, and which consists of carbon atoms and from one to four heteroatoms independently selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyridyl N-oxide, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, tetrazole, thienyl, benzothienyl, thiamorpholinyl, thiamorpholinyl sulfoxide, thiamorpholinyl sulfone, and oxadiazolyl. Morpholino is the same as morpholinyl.

Except where noted herein, the term "heteroaryl" refers to a monocyclic unsaturated heterocycle having a specified number of atom members (e.g., 4, 5, 6 or 7-membered), including a specified number of heteroatoms (e.g., 1, 2, 3 or 4 heteroatoms independently selected from N, O or S), or a bicyclic unsaturated ring system having a specified number of atom members (e.g., 7, 8, 9, 10, 11 or 12-membered) including a specified number of heteroatoms (e.g., 1, 2, 3, 4, 5, 6, 7, 8, 9 or 10 heteroatoms independently selected from N, S or O) or a tricyclic unsaturated ring system having a specified number of atom members (e.g., 12-, 13- or 14-membered) including a specified number of heteroatoms (e.g., 1, 2, 3, 4, 5, 6, 7, 8, 9 or 10 heteroatoms independently selected from N, S or O) e.g., 5-membered rings containing one nitrogen (pyrrole), one oxygen (furan) or one sulfur (thiophene) atom, 5-membered rings containing one nitrogen and one sulfur (thiazole) atom, 5-membered rings containing one nitrogen and one oxygen (oxazole or isoxazole) atom, 5-membered rings containing two nitrogen (imidazole or pyrazole) atoms, five-membered aromatic rings containing three nitrogen atoms, five-membered aromatic rings containing one oxygen, one nitrogen or one sulfur atom, five-membered aromatic rings containing two heteroatoms independently selected from oxygen, nitrogen and sulfur, 6-membered rings containing one nitrogen (pyridine), or one oxygen (pyran) atom, 6-membered rings containing two nitrogen (pyrazine, pyrimidine, or pyridazine) atoms, 6-membered rings containing three nitrogen (triazine) atoms, a tetrazolyl ring; a thiazinyl ring; or coumarinyl. Examples of such ring systems are furanyl, thienyl, pyrrolyl, pyridinyl, pyrimidinyl, indolyl, imidazolyl, triazinyl, thiazolyl, isothiazolyl, pyridazinyl, pyrazolyl, oxazolyl, oxadiazolyl, triazolyl and isoxazolyl.

The term "saturated heterocycle" refers to a saturated monocyclic 5- to 8-membered ring having 1-4 heteroatoms selected from N, O and S, or a 7- to 12-membered saturated bicyclic ring system having 1-6 heteroatoms selected from N, O and S, or a 12- to 14-membered ring having 1-4 heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Except where noted herein, the term "carbocycle" (and variations thereof such as "carbocyclic" or "carbocyclyl") as used herein, unless otherwise indicated, refers to a $C_3$ to $C_8$ monocyclic saturated or unsaturated ring, e.g., $C_3$-8 carbocycle or a $C_{10}$ bicyclic saturated or unsaturated ring. The carbocycle may be attached to the rest of the molecule at any carbon atom which results in a stable compound. Saturated carbocyclic rings are also referred to as "cycloalkyl" rings, e.g., cyclopropyl, cyclobutyl, etc. Unsaturated carbocyclic rings are also referred to as aryl rings.

Except where noted, the term "aryl" refers to a stable 6- to 10-membered mono- or bicyclic ring system such as phenyl, or naphthyl. The aryl ring can be unsubstituted or substituted with one or more of $C_1$-4 alkyl, hydroxyl, alkoxy, halogen, or amino.

"Celite®" (Fluka) diatomite is diatomaceous earth, and can be referred to as "celite".

Except where noted herein, aryl groups and carbocycle groups may be unsubstituted, or substituted on any one or more carbon atoms, with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, HS(O)$_{0-2}$—, ($C_1$-$C_6$ alkyl)S(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)S(O)$_{0-2}$, ($C_1$-$C_6$ alkyl)C(O)NH—, HC(O)NH—, $H_2$N—C(NH)—, —O($C_1$-$C_6$ alkyl)$CF_3$, ($C_1$-$C_6$ alkyl)C(O)—, HC(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)C(O)$_{1-2}$($C_1$-$C_6$ alkyl)-, ($C_1$-$C_6$ alkyl)C(O)$_{1-2}$—, HC(O)$_{1-2}$($C_1$-$C_6$ alkyl)-, ($C_1$-$C_6$ alkyl)OC(O)NH—, HOC(O)NH—, —P(O)(OH)$_2$, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

Except where noted herein, heterocycles may be unsubstituted, or substituted on any one or more carbon atoms, with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, HS(O)$_{0-2}$—, ($C_1$-$C_6$ alkyl)S(O)$_{0-2}$ ($C_1$-$C_6$ alkyl)-, HS(O)$_{0-2}$($C_1$-$C_6$ alkyl)-, ($C_1$-$C_6$ alkyl)S(O)$_{0-2}$—, ($C_1$-$C_6$ alkyl)C(O)NH—, HC(O)NH—, $H_2$N—C(NH)—, —O($C_1$-$C_6$ alkyl)$CF_3$, HC(O)—, ($C_1$-$C_6$ alkyl)C(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)O—, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$, ($C_1$-$C_6$ alkyl)OC(O)NH—, HOC(O) NH—, silyl groups (including trimethylsilyl, tetramethylsilyl, or supersilyl groups such as tri(trimethylsilyl)silyl or a silicon group connected to tert butyl groups), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, or independently or additionally substituted with 1 substituent on any one or more nitrogen atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, —C(O)$C_1$-6 alkyl, —C(O)NH$C_1$-$C_6$ alkyl, —C(O) NH$_2$, —$C_1$-$C_6$ alkylC(O)NH$_2$, —$C_1$-$C_6$ alkylOC(O)NH$_2$, or independently or additionally substituted with 1 substituent on any one or more sulfur atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, where such substitution results in formation of a stable compound.

Except where noted herein, structures containing substituent variables such as variable "R" below:

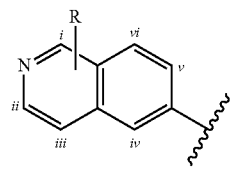

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also includes derivatives of the compound of Formula I, acting as prodrugs and solvates. Prodrugs, following administration to the patient, are converted in the body by normal metabolic or chemical processes, such as through hydrolysis in the blood, to the compound of Formula 1. Such prodrugs include those that demonstrate enhanced bioavailability, tissue specificity, and/or cellular delivery, to improve drug absorption of the compound of Formula I. The effect of such prodrugs may result from modification of physicochemical properties such as lipophilicity, molecular weight, charge, and other physicochemical properties that determine the permeation properties of the drug.

The preparation of pharmacologically acceptable salts from compounds of the Formula (I) capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula (I) form stable alkali metal, alkaline earth metal or optionally substituted ammonium salts. If the compounds of the Formula (I) have basic groups, stable acid addition salts can also be prepared using strong acids. For this, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerophosphoric, lactic, malic, adipic, citric, fumaric, maleic, gluconic, glucuronic, palmitic or trifluoroacetic acid are suitable.

The invention also relates to medicaments containing at least one compound of the Formula (I) and/or of a pharmaceutically acceptable salt of the compound of the Formula (I) and/or an optionally stereoisomeric form of the compound of the Formula (I) or a pharmaceutically acceptable salt of the stereoisomeric form of the compound of Formula (I), together with a pharmaceutically suitable and pharmaceutically acceptable vehicle, additive and/or other active substances and auxiliaries.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Factor XIa inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the Factor XIa inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

The compounds of the invention may also be kallikrein inhibitors and especially useful for treatment of hereditary angioedema.

Examples of devices that come into contact with blood include vascular grafts, stents, orthopedic prosthesis, cardiac prosthesis, and extracorporeal circulation systems The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor XIa inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor XIa inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the Factor XIa inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Abbreviations used herein are as follows: ABCA1 is adenosyltriphosphate-binding cassette-family A1; Ac is acetyl; AcOH is acetic acid; AIBN is 2,2'-azobis(2-methyl-propionitrile); aq. is aqueous; Ar is Aryl; atm is normal atmospheric pressure; Bn is benzyl; Boc is tert-butyloxy-carbonyl; br is broad; Bu is butyl; tBu is tert-butyl; celite is Celite® diatomaceous earth; conc. is concentrated (for HCl, conc. is a 12 M aq. solution); cpm is counts per minute; DAST is diethylaminosulfur trifluoride; DBU is 1,8-diaz-abicyclo[5.4.0]undec-7-ene; DCE is 1,2-dichlorethane; DCM is dichloromethane; d is doublet; DEAD is diethyl-azodicarboxylate; DIAD is diisopropylazodicarboxylate; DIBAL-H is diisobutyl-aluminum hydride; DIPEA is diiso-propylethylamine; DMA is N,N-dimethylacetamide; DMAP is 4-dimethylaminopyridine; DMF is N,N-dimethylforma-mide; DMPU is 1,3-dimethyl-3,4,5,6-tetrahydro-2(1H)-py-rimidinone; dppf is 1,1'-bis(diphenylphosphino)ferrocene; DMSO is dimethyl sulfoxide; EDC is N-(3-dimethylamino-propyl)-N'-ethylcarbodiimide hydrochloride; EDTA is eth-ylendiamine tetraacetic acid; equiv. is equivalent(s); ES-MS is electrospray ion-mass spectroscopy; Et is ethyl; $Et_2O$ is diethyl ether; EtOH is ethanol, EtOAc is ethyl acetate; FXR is farnesoid X receptor; g is gram; h is hours; HATU is O-(7-azabenzotriazol-1-yl)-N,N,N',N'-tetramethyluronium hexafluorophosphate; HetAr or HAR is Heteroaryl; HMG-CoA is 3-hydroxy-3-methyl-glutaryl coenzyme A; HOAt is 1-hydroxy-7-azabenzotriazole; HOBt is 1-hydroxybenzotri-azole; HPLC is high performance liquid chromatography; i is Iso; $IC_{50}$ is concentration at which 50% inhibition exists; IPA is isopropyl alcohol; kg is kilogram; L is liter; LDA is lithium diisopropylamide; LG is leaving group; LHMDS is lithium bis(trimethylsilyl)amide; LTB4 is leukotriene B4; LXR is liver X receptor; m is meta; m is multiplet; M is molar; Me is methyl; m.p. is melting point; mg is milligram; μg is microgram; MeOH is methanol; MHz is megahertz; min is minute; mL is milliliter; mm is millimeter; μL is microliter; mM is milimolar; μM is micromolar; mmol is milimoles; Ms is methanesulfonyl; MS is mass spectrum, and a mass spectrum obtained by ES-MS may be denoted herein by "ES"; m/z is mass to charge ratio; n is normal; N is normal; NBS is N-bromosuccinimide; nm is nanometer; nM is nanomolar; NMM is N-methylmorpholine; NMO is N-methylmorpholine-N-oxide; NMP is N-methylpyrolidin-2-one; nPr is n-propyl; o is ortho; p is pentet; p is para; PEG is polyethylene glycol; pH is a logarithmic scale measure of the activity of a hydrogen ion; Ph is phenyl; Phth is phthalimidoyl; PPARα is peroxisome proliferator activated receptor alpha; Pr is propyl; iPr is isopropyl; psi is pounds per square inch of pressure; p-TSA is para-toluenesulfonic acid; PyBOP is benzotriaxole-1-yl-oxy-tris-pyrrolidino-phosphonium hexafluorophosphate; q is quartet; rt is room temperature; s is singlet; sec is secondary; SFC is super-critical fluid chromatography; t is triplet; tBuOH is tert-butanol; tert is tertiary; Tf is trifluoromethanesulfonyl; TFA is trifluoroacetic acid; and THF is tetrahydrofuran; TLC is thin layer chromatography; Ts is tosyl; UV is ultraviolet; W is watts; wt. % is percentage by weight; xg is times gravity; $α_D$ is the specific rotation of polarized light at 589 nm; ° C.

is degrees Celsius; % w/v is percentage in weight of the former agent relative to the volume of the latter agent.

Methods for Making the Compounds of Present Invention

General Methods

The compounds of the present invention can be readily produced from known compounds or commercially available compounds by, for example, known processes described in published documents, and produced by production processes described below. The present invention is not limited to the production processes described below. The invention also includes processes for the preparation of compounds of the invention.

It should be noted that, when compounds of the present invention synthesized has a reactive group such as hydroxy group, amino group, carboxyl group, or thiol group as its substituent, such group may be adequately protected with a protective group in each reaction step and the protective group may be removed at an adequate stage. The process of such introduction and removal of the protective group may be adequately determined depending on the group to be protected and the type of the protective group, and such introduction and removal are conducted, for example, by the process described in the review section of Greene, T. W., et. al., "*Protective Groups in Organic Synthesis*", 2007, 4th Ed., Wiley, New York, or Kocienski, P., "*Protecting Groups*" 1994, Thieme.

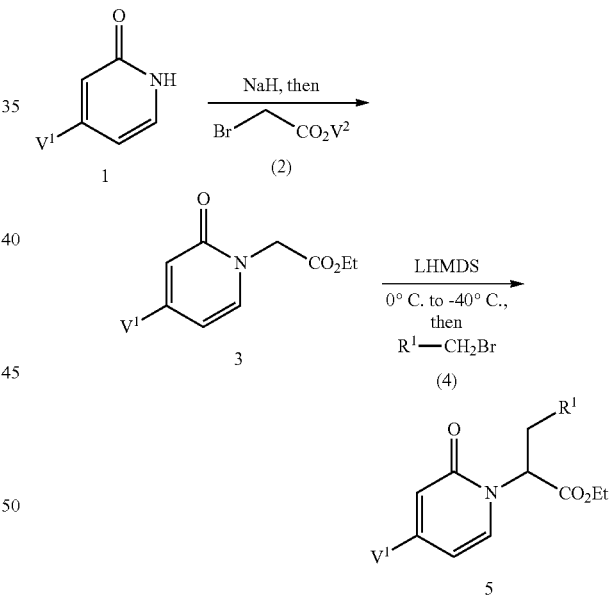

Scheme A $V^1$ = Br, OBn, or a suitable representation of A, as described in formula I
$V^2$ = methyl or ethyl Reaction scheme A illustrates a method of synthesis of compounds of structural formula 5. In the most common examples, 4-substituted pyridones of type 1 are treated with a suitable base, such as NaH, or the like, in an inert solvent, such as THF or DMF, at temperatures typically between 0° C. and room temperature for time periods within, but not limited to, 15 min to 1 h. The corresponding alkylating agent, such as methyl bromoacetate is then added, and the reaction is allowed to stir within the above temperature range for 1-24 h.

The product of the reaction is an N-substituted pyridone acetate of type 3 that is then treated with a base, such as LHMDS or LDA, in an inert solvent, such as THF, DMF, DMA or mixtures thereof, at temperatures typically between −20° C. and −78° C. The resulting anion is then treated with an electrophile of type 4, that is commonly a substituted or unsubstituted benzyl bromide, or in some cases, allyl bromide, and is added in a dropwise manner. The reaction is commonly stirred at the addition temperature for a period of time, typically 15-30 min, and subsequently warmed to 0° C. and allowed to stir for up to 3 h. The product of the reaction is an α-substituted pyridone acetate of type 5 that can be carried on to afford compounds of the present invention (I).

Scheme B

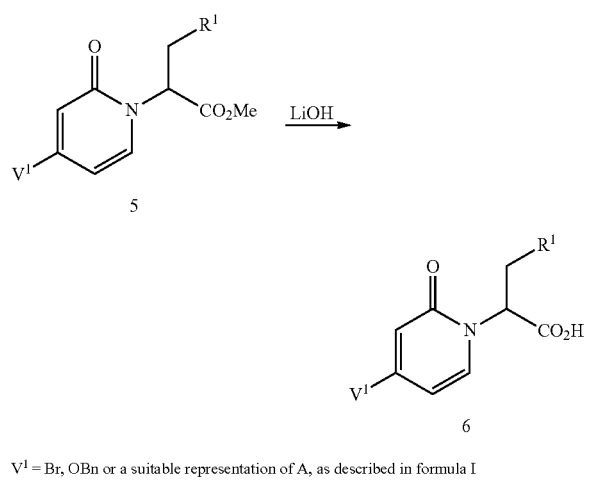

$V^1$ = Br, OBn or a suitable representation of A, as described in formula I

Reaction scheme B illustrates a method of synthesis of compounds of type 6. In this method, a compound of type 5 can be hydrolyzed to a carboxylic acid of type 6 using a variety of methods known to those skilled in organic synthesis. The product carboxylic acid of structural formula 6 can be used as a coupling partner in reaction Scheme D or synthetically modified using a variety of methods known in organic synthesis to afford compounds of the present invention (I).

Scheme C

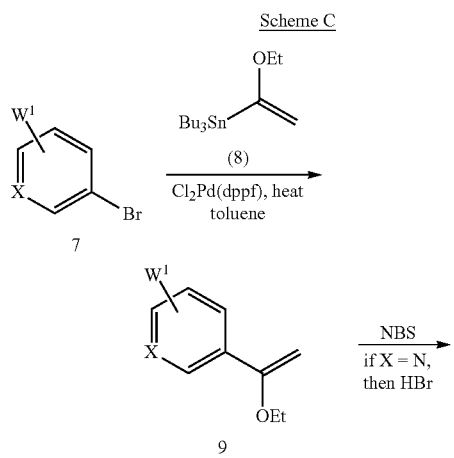

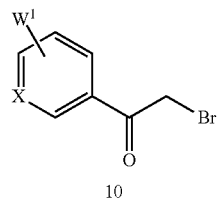

X = CH or N
$W^1$ = $R^{19}$ or $R^{20}$, as described in formula I

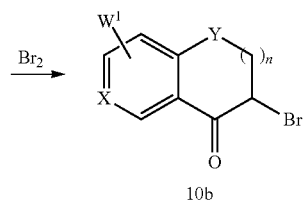

Y = CH$_2$ or O
n = 0, 1 or 2

Reaction scheme C illustrates a method for the synthesis of aryl and heteroaryl α-bromoketones of type 10 and type 10b. In this method, aryl or heteroaryl bromides of type 7 are treated with a stannyl vinyl ether, such as example 8, in a reaction commonly referred to as a Stille coupling. The reaction is performed in a suitable inert solvent, such as toluene or xylene, or the like, at temperatures typically between 70° C. and the solvent boiling temperature for between 1-24 h. The Stille coupling reaction employs a suitable palladium catalyst, suitable palladium catalyst, such as [1,1'-bis(diphenylphosphino)ferrocene]-dichloropalladium(II), or tetrakis(triphenylphosphine) palladium (0), or the like. The product of the reaction is a vinyl ether of type 9, which is subsequently reacted with a brominating reagent, commonly NBS, in a suitable inert solvent, such as THF, to afford α-bromoketones of type 10. When α-bromoketones of type 10 contain a basic atom (X=N), a preferred method of isolation involves subsequent treatment with a suitable acid, such as HBr, which affords the corresponding pyridinium salt that can be isolated as a stable solid.

An alternate method for the synthesis of α-bromoketones of type 10b involves treatment of a cyclic ketone of type 10a with a suitable brominating reagent, such as bromine. The reaction is typically run in an inert solvent, such as diethyl ether or the like, at reduced temperatures at or below 0° C., to afford α-bromoketones of type 10b.

Scheme D

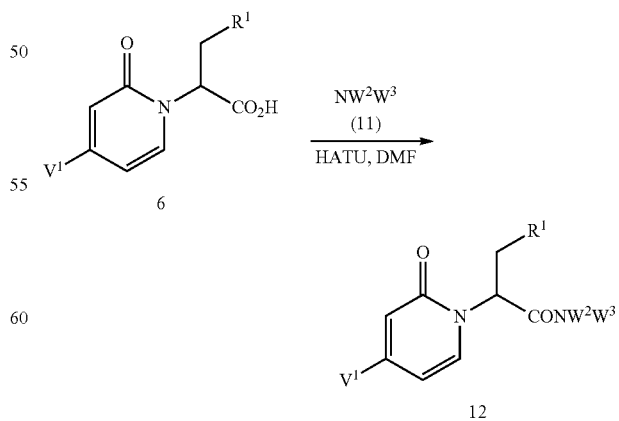

$W^2$ and $W^3$ = suitable representations of $R^2$, as defined in formula I

Reaction scheme D illustrates a method of synthesis of compounds of structural formula 12. In the most general case, 6 is treated with an amine of type 11 to afford amides of type 13. The amide bond coupling reaction illustrated in reaction scheme D is conducted in an appropriate inert solvent such as DMF, DCM or the like and may be performed with a variety of reagents suitable for amide coupling reactions such as HATU, EDC or PyBOP. Preferred conditions for the amide bond coupling reaction shown in reaction Scheme D are known to those skilled in organic synthesis. Such modifications may include, but are not limited to, the use of basic reagents such as triethylamine, DIPEA, or NMM, or the addition of an additive such as HOAt or HOBt. Alternatively, 11 may be treated with an activated ester or acid chloride derivative of 6, to afford 12. The amide bond coupling shown in reaction Scheme D is usually conducted at temperatures between 0° C. and room temperature, occasionally at elevated temperatures, and the coupling reaction is typically conducted for periods of 1 to 24 hours. Amide 12 can be carried on to afford compounds of the present invention (I).

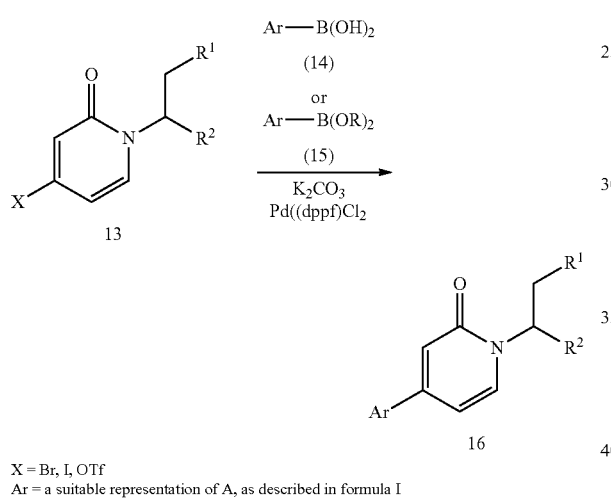

X = Br, I, OTf
Ar = a suitable representation of A, as described in formula I

Reaction scheme E illustrates a method of synthesis of compounds of structural formula 16. In this method, commonly referred to as the Suzuki reaction, compounds of type 13 can be treated with an aryl- or heteroaryl-boronic acid of type 14, or alternatively, an aryl- or heteroaryl-boronate of type 15, in the presence of a suitable palladium catalyst, such as [1,1'-bis(diphenylphosphino)ferrocene]-dichloropalladium(II), or tetrakis(triphenylphosphine) palladium (0), or the like, and a mild base, such as sodium carbonate, sodium phosphate tribasic, or the like (*Pure Appl. Chem.* 1991, 63, 419-422). The reaction is usually performed in a suitable degassed aqueous mixture of inert organic solvents, such as toluene, ethanol or dioxane, at elevated temperatures, generally between 70° C. and the boiling temperature of the solvent mixture, for a period of 3-24 h. Alternatively, those skilled in the art can perform the Suzuki reaction described above in a suitable vessel that enables heating in a microwave reactor to superheated reaction temperatures that can reduce reaction times to between 1 min and 1 h. Recently, conditions suitable for performing Suzuki reactions at room temperature have been published (for example, see: *J. Am. Chem. Soc.* 2000, 122, 4020-4028, and references therein). The products of the Suzuki reaction, 16, can, if necessary, be carried forward to compounds of the present invention (I).

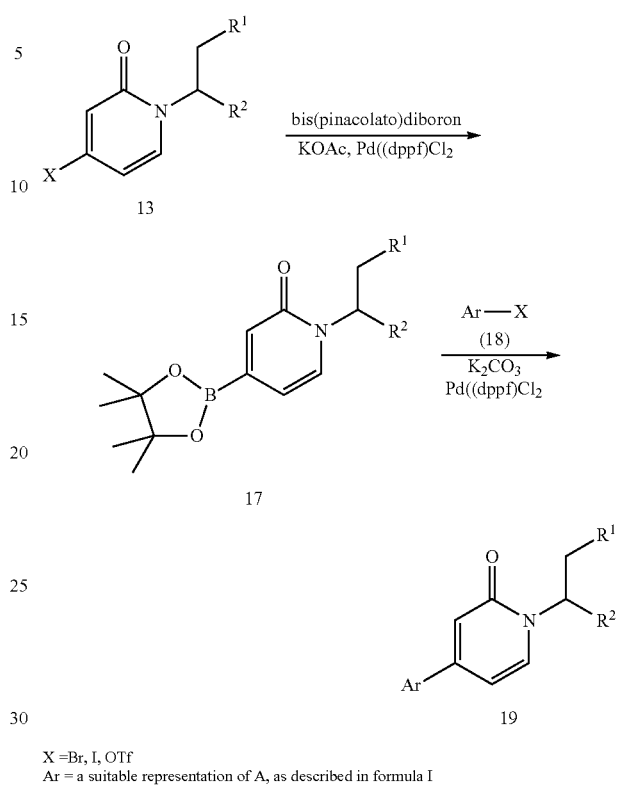

X = Br, I, OTf
Ar = a suitable representation of A, as described in formula I

Reaction scheme F illustrates an alternate method of synthesis of compounds of structural formula 19. In this method, a compound of type 13 is treated with bis(pinacolato)diboron in the presence of a suitable palladium catalyst, such as [1,1'-bis(diphenylphosphino)ferrocene]-dichloropalladium(II), and an activating reagent, such as potassium acetate, or the like. The reaction is usually performed in a suitable degassed inert organic solvent, such as dimethyl sulfoxide or dioxane, or the like, at elevated temperatures, generally between 70° C. and 100° C., for a period of 1-24 h (*J. Org. Chem.* 1995, 60, 7508-7510). The product of this reaction is an intermediate boronate of type 17, which can employ a reagent of type 18 and participate in organotransition metal catalyzed cross-coupling reactions, such as the Suzuki reaction (Scheme E), to afford compounds of type 19, that if necessary, can be carried forward to compounds of the present invention (I).

Scheme G

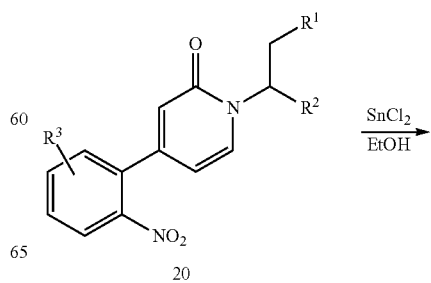

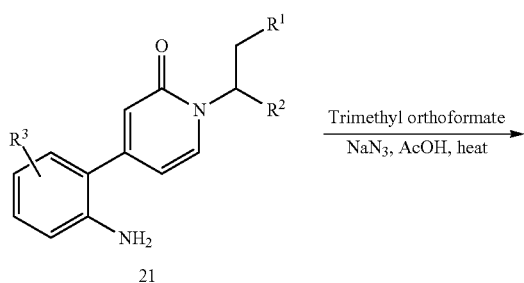

21

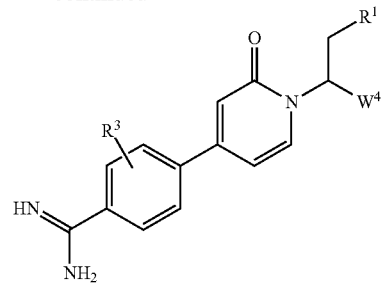

24

W⁴ = a suitable representation of R², as described in formula I

Reaction scheme H illustrates a preferred method for converting nitriles of type 23 to the corresponding amidines of type 24. In this method, the aryl nitrile (23) is treated with an ammonia equivalent, such as LHMDS, in an inert solvent, such as THF. This reaction is typically performed at room temperature, and the direct product of the reaction, silylamide (not shown), is subsequently hydrolyzed in situ by treatment with a suitable acid source, such as HCl, to afford amidines of type 24 that can be carried forward, if necessary, to compounds of the present invention (I).

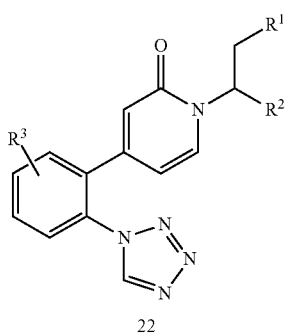

22

Reaction scheme G illustrates a preferred method for the synthesis of N1-aryl tetrazoles of type 22. In this method, nitrophenyl intermediates of type 20 are treated with a mild reducing agent, such as tin(II)chloride, in a suitable polar solvent, such as ethanol, isopropanol or mixtures thereof, at temperatures ranging between room temperature and 60° C. to effect reduction of the nitrophenyl moiety to the corresponding aniline of type 21. The anilide (21) is then transformed into an N1-linked tetrazole of type 22 by further reacting with sodium azide and a formate donor, such as trimethyl orthoformate, in a suitable solvent, such as acetic acid. The tetrazole formation derived from intermediates of type 21 is optimally performed at elevated temperatures ranging from 80-110° C. for periods of 1.5-3.5 h, as longer reaction times can lead to additional side reactions that compromise the overall yield of 22. Compounds of type 22, that if necessary, can be carried forward to compounds of the present invention (I).

Scheme I

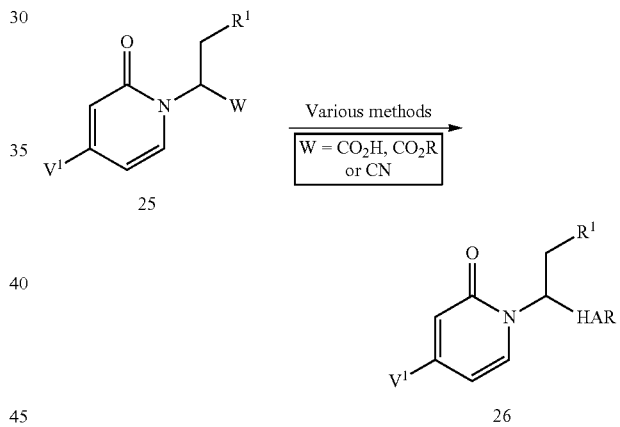

$V^1$ = Br, OBn, or a suitable representation of A, as described in formula I
HAR = a suitable representation of R², as described in formula I Scheme I illustrates that compounds of structural formula 25 can be elaborated to a variety of heterocyclic (HAR) derivatives of structural formula 26 using known methods in organic synthesis. Specific examples of such transformations are shown in the Examples section.

Leading references for effecting such transformations include:
1) Joule, J. A; Mills, K and Smith, G. F. *Heterocyclic Chemistry*, Chapman & Hall, 1995, 3rd Edn., and references cited therein;
2) Katrittzky, A. R.; Rees, C. W. (Eds), *Comprehensive Heterocyclic Chemistry: The Structure, Reactions, Synthesis, and Uses of Heterocyclic Compounds*, Pergamon Press, Oxford, 1984, 8v, and references cited therein; and
3) *Comprehensive Heterocyclic Chemistry II: Review of the Literature 1982-1995: The Structure, Reactions, Synthesis and Uses of Heterocyclic Compounds*, Pergamon Press, New York, 2nd Edn., 1996, 1 v, and references cited therein.

Scheme H

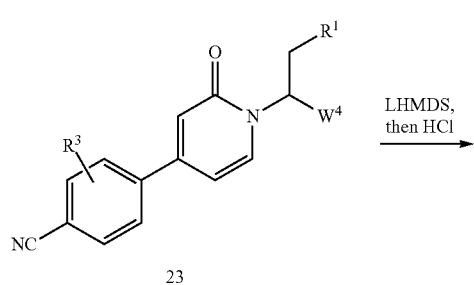

23

Scheme J

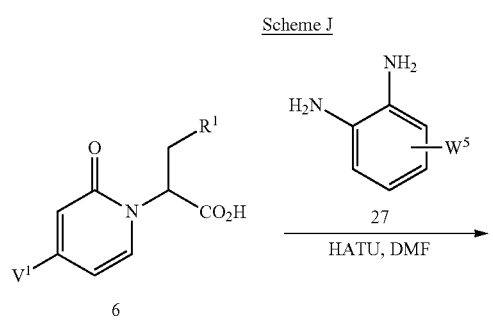

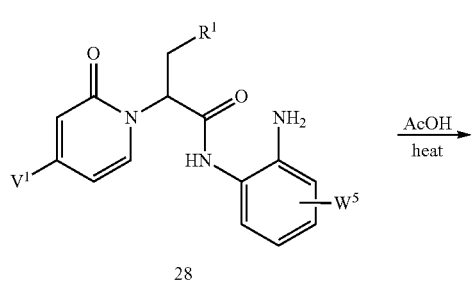

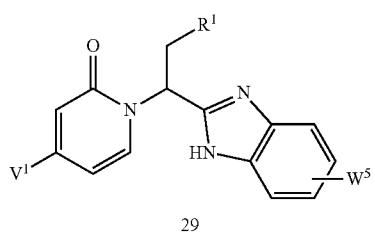

$V^1$ = Br, OBn, or a suitable representation of A, as described in formula I
$W^5$ = a suitable representation of $R^{18}$, as described in formula I Reaction scheme J illustrates a preferred method for the synthesis of benzimidazoles of type 29. In this method, carboxylic acids of type 6 are coupled with aryl diamines of type 27 under reaction conditions similar to those described above in scheme D to afford an o-amino anilide (28) that is subsequently cyclized to afford benzimidazoles of type 29. The cyclization reaction is commonly performed in high boiling solvents, such as acetic acid, at elevated temperatures, commonly between 70° C. and the boiling temperature of the solvent, commonly for 2-16 h. The product of the reaction (29) can be carried forward, if necessary, to compounds of the present invention (I).

Scheme K

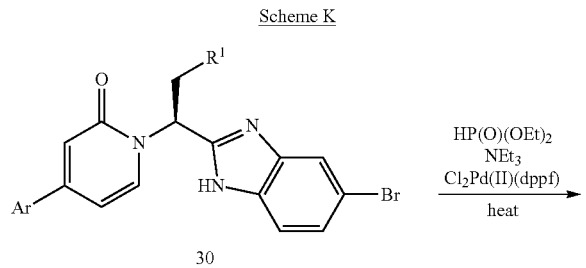

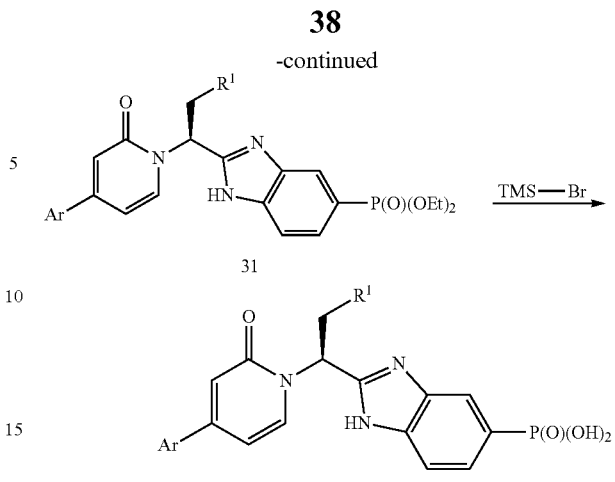

Ar = a suitable representation of A, as described in formula I

Reaction scheme K illustrates a preferred method for the synthesis of phosphonic acids of type 32. In this method, an aryl bromide, exemplified by benzimidazole 30, is treated with a phosphorylating agent, such as diethyl phosphite, in the presence of a palladium catalyst, such as [1,1'-bis(diphenylphosphino)ferrocene]-dichloropalladium(II), or tetrakis(triphenylphosphine) palladium (0), or the like, and a mild base, such as triethylamine or the like (for example, see: J. Med. Chem. 1992, 35, 1345). The reaction is conducted in a suitable degassed inert solvent, such as toluene or xylene, at elevated temperatures between 100° C. and the boiling temperature of the solvent for 12-24 h. An alternate preferred method involves heating the degassed reaction mixture described above in a microwave reactor, which can result in shorter required reaction times. The product of the reaction is a phosphodiester of type 31, which can be converted to the corresponding phosphonic acid, 32, via treatment with bromotrimethylsilane in an inert solvent, such as dichloromethane, at room temperature for 12-72 h (for example, see: J. Med. Chem. 2011, 54, 153).

Scheme L

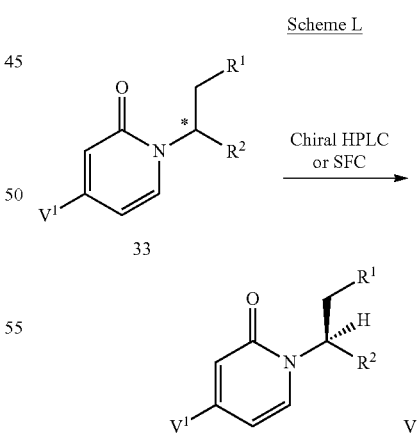

$V^1$ = Br, OBn or a suitable representation of A, as described in formula I

Scheme L illustrates a method for the resolution of a compound of structural formula 33 in which the asterisked carbon is a center of chirality. Generally, the latter, or intermediates en route to their preparation, may be resolved to afford enantiomerically pure compounds such as 34 and 35 by chiral stationary phase liquid chromatography techniques or other suitable methods known in organic synthesis.

Intermediate i-1

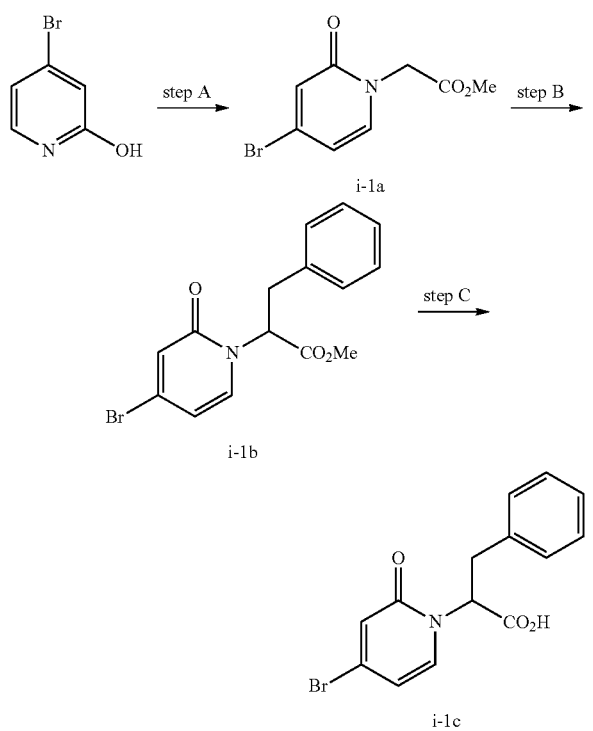

Step A: Preparation of methyl 2-(4-bromo-2-oxopyridin-1(2H)-yl)acetate (i-1a)

A solution of 4-bromopyridine (4.20 g, 24.1 mmol) in THF (80 mL) was cooled to 0° C. Sodium hydride (965 mg of a 60% dispersion in mineral oil, 24.1 mmol) was added in several portions over 5 min, and the resulting mixture was stirred at 0° C. for 15 min, at which point the cooling bath was removed. After warming to rt over 30 min, the mixture was recooled to 0° C., and methyl bromoacetate (2.2 mL, 24.1 mmol) was added rapidly, and the reaction mixture was allowed to warm slowly to rt over 2 h. The reaction was quenched by addition of satd. aq. NH$_4$Cl, and the resulting mixture was extracted w/EtOAc. The combined organics were dried (Na$_2$SO$_4$), filtered and concentrated to afford the title compound as a pale yellow oil. m/z (ES) 248 (MH)$^+$.

Step B: Preparation of methyl 2-(4-bromo-2-oxopyridin-1(2H)-yl)-3-phenylpropanoate (i-1b)

LHMDS (18.5 mL of a 1.0 M THF solution, 18.5 mmol) was added dropwise to a stirred solution of i-1a (4.13 g, 16.8 mmol) in THF (55 mL) at −78° C. The resulting mixture was stirred at −78° C. for 1 h, at which time, benzyl bromide (2.0 mL, 16.8 mmol) was added rapidly dropwise, and the reaction mixture was allowed to stir at −78° C. After 1.5 h, the reaction was warmed to 0° C. and allowed to stir at 0° C. for 4 h. The reaction was quenched via addition of satd. aq. NH$_4$Cl and extracted with EtOAc. The layers were separated, and the aq. layer was extracted with EtOAc. The combined organics were washed with brine, dried (Na$_2$SO$_4$), filtered and concentrated to afford a crude residue that was purified by flash chromatography on silica gel (gradient elution; 0%-40% EtOAc/hexanes as eluent) afforded the title compound i-1b as a white powder. m/z (ES) 336 (MH)$^+$.

Step C: Preparation of 2-(4-bromo-2-oxopyridin-1 (2H)-yl)-3-phenylpropanoic acid (i-1c)

Lithium hydroxide (5.3 mg, 0.22 mmol) was added to a stirred suspension of i-1b (50 mg, 0.15 mmol) in dioxane: water (750 μL of a 4:1 mixture), and the resulting mixture was heated to 50° C. After 2 h, the reaction was cooled to rt and adjusted to pH-3 via the addition of 1M aq. HCl. The mixture was diluted with EtOAc, dried (MgSO$_4$), filtered and concentrated to afford the title compound i-1c as a white solid. m/z (ES) 323 (MH)$^+$.

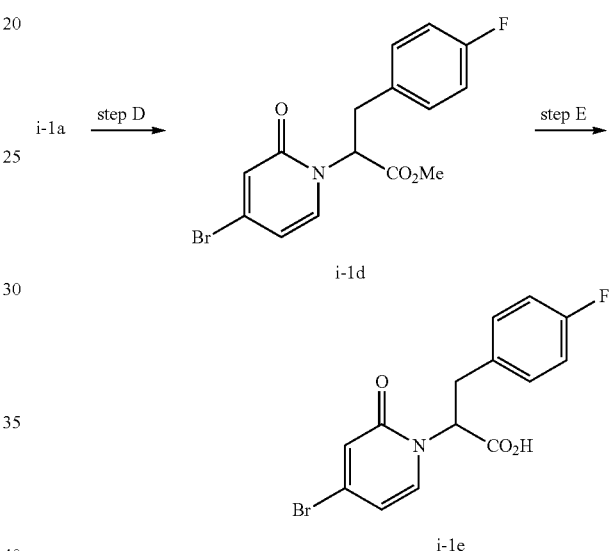

Step D: Preparation of methyl 2-(4-bromo-2-oxopyridin-1(2H)-yl)-3-(4-fluorophenyl)propanoate (i-1d)

LHMDS (16.7 mL of a 1.0 M THF solution, 16.7 mmol) was added slowly dropwise to a stirred solution of i-1a (3.92 g, 15.9 mmol) in DMA (50 mL) at −40° C. Upon addition of base, the reaction mixture became a bright orange-yellow slurry, and after 30 min, 4-fluorobenzyl bromide (1.99 mL, 15.9 mmol) was added rapidly dropwise. After 2 h, the reaction was quenched via the addition of satd. aq. NH$_4$Cl, and the resulting mixture was extracted with EtOAc. The combined organics were washed with water and brine, dried (Na$_2$SO$_4$) and concentrated in vacuo. Purification of the crude residue by flash chromatography on silica gel (gradient elution; 0%-40% EtOAc/hexanes as eluent) afforded the title compound i-1d. m/z (ES) 354 (MH)$^+$.

Step E: Preparation of 2-(4-bromo-2-oxopyridin-1 (2H)-yl)-3-(4-fluorophenyl)propanoic acid (i-1e)

Compound i-1e was prepared following procedures similar to those described from Intermediate i-1, Step C for the preparation of compound i-1c, substituting compound i-1d for i-1b. m/z (ES) 341 (MH)$^+$.

TABLE i-1

| R | R' | | |
|---|---|---|---|
| Br | 3-fluorophenyl | i-1f | i-1l |
| | 4-chlorophenyl | i-1g | i-1m |
| | 3-chlorophenyl | i-1h | i-1n |
| | 4-bromophenyl | i-1i | i-1o |
| | 4-(trifluoromethoxy)phenyl | i-1j | i-1p |
| OBn | vinyl | i-1k | i-1q |

Table i-1. Parent Ion m/z (MH)$^+$ data for compounds

For i-1f: methyl 2-(4-bromo-2-oxopyridin-1(2H)-yl)-3-(3-fluorophenyl)propanoate

For i-1g: methyl 2-(4-bromo-2-oxopyridin-1(2H)-yl)-3-(4-chlorophenyl)propanoate: m/z (ES) 370 (MH)$^+$ For i-1j: methyl 2-(4-bromo-2-oxopyridin-1(2H)-yl)-3-(4-(trifluoromethoxy)phenyl)propanoate For i-1k: methyl 2-(4-(benzyloxy)-2-oxopyridin-1(2H)-yl)pent-4-enoate: m/z (ES) 314 (MH)$^+$ For i-1l: 2-(4-bromo-2-oxopyridin-1(2H)-yl)-3-(3-fluorophenyl)propanoic acid: m/z (ES) 342 (MH)$^+$ Intermediate i-2

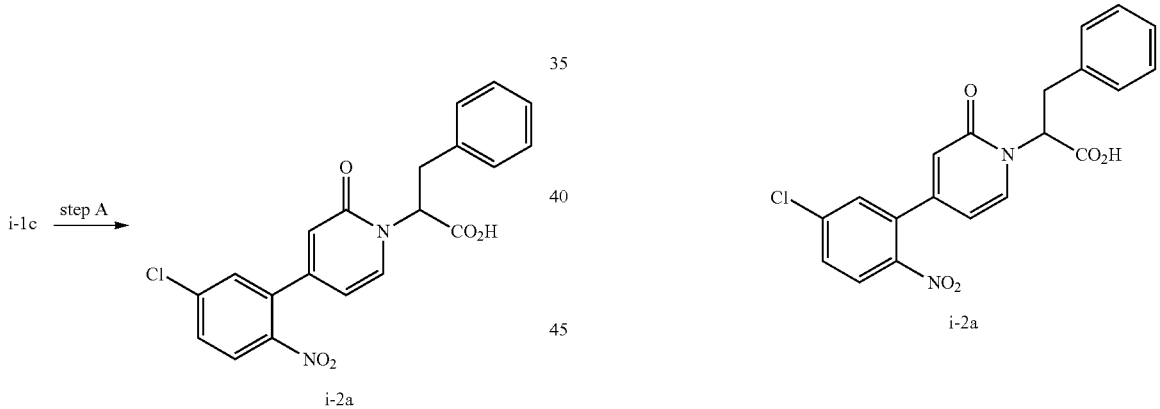

Step A: Preparation of 2-(4-(5-chloro-2-nitrophenyl)-2-oxopyridin-1(2H)-yl)-3-phenylpropanoic acid (i-2a)

A degassed suspension of i-1c (100 mg, 0.310 mmol), (5-chloro-2-nitrophenyl)boronic acid (94 mg, 0.466 mmol), potassium phosphate, tribasic (0.78 mL of a 1M aq. solution, 0.778 mmol), and 1,1'-bis(di-tert-butylphosphino)ferrocenepalladium dichloride (20 mg, 0.031 mmol) in NMP (2.6 mL) was heated to 90° C. After 16 h, the reaction mixture was cooled to rt, and partitioned between EtOAc and water. The layers were separated, the aq. layer was acidified with 1M HCl and extracted with EtOAc. The combined organics were washed with water and brine, dried (MgSO$_4$), filtered and concentrated to afford the title compound i-2a as a crude brown solid. m/z (ES) 399 (MH)$^+$.

Step B: Preparation of methyl 2-(4-(5-chloro-2-nitrophenyl)-2-oxopyridin-1(2H)-yl)-3-phenylpropanoate (i-2b)

A degassed suspension of i-1b (500 mg, 1.49 mmol), (5-chloro-2-nitrophenyl)boronic acid (329 mg, 1.64 mmol), potassium carbonate (206 mg, 1.49 mmol), and [1,1'-bis(diphenylphosphino)ferrocene]dichloropalladium(II) (163 mg, 0.22 mmol) in EtOH:toluene (10 mL of a 4:1 mixture) was heated in a microwave reactor to 110° C. for 10 min. After cooling to rt, the reaction mixture was diluted with EtOAc and filtered through a column of Celite®, which was rinsed with additional portions of EtOAc. The combined organics were dried (Na$_2$SO$_4$), filtered and concentrated, and the resulting crude residue was purified by flash chromatography on silica gel (gradient elution; 0%-30% EtOAc/hexanes as eluent) to afford the title compound i-2b as a white solid. m/z (ES) 413 (MH)$^+$.

Step C: Preparation of 2-(4-(5-chloro-2-nitrophenyl)-2-oxopyridin-1(2H)-yl)-3-phenylpropanoic acid (i-2a)

Lithium hydroxide (181 mg, 7.56 mmol) was added to a stirred solution of 1a (1.04 g, 2.52 mmol) in dioxane:water (12 mL of a 4:1 mixture), and the reaction mixture was heated to 60° C. After 1 h, the reaction was cooled to rt and adjusted to pH-3 via addition of 1M aq. HCl. The resulting mixture was diluted with EtOAc and washed with brine. The organics were dried ($Na_2SO_4$), filtered and concentrated to afford i-2a as a white solid. m/z (ES) 399 $(MH)^+$.

TABLE i-2

| R | | |
|---|---|---|
| | methyl ester | carboxylic acid |
| 4-fluorophenyl | i-2f | i-2l |
| 3-fluorophenyl | i-2g | i-2m |
| 4-chlorophenyl | i-2h | i-2n |
| 3-chlorophenyl | i-2i | i-2o |
| 4-bromophenyl | i-2j | i-2p |
| 4-(trifluoromethoxy)phenyl | i-2k | i-2q |

Table i-2. Parent Ion m/z $(MH)^+$ data for compounds

For i-2f: methyl 2-(4-(5-chloro-2-nitrophenyl)-2-oxopyridin-1(2H)-yl)-3-(4-fluorophenyl)propanoate; m/z (ES) 431 $(MH)^+$.

For i-2h: methyl 2-(4-(5-chloro-2-nitrophenyl)-2-oxopyridin-1(2H)-yl)-3-(4-chlorophenyl)propanoate; m/z (ES) 447 $(MH)^+$.

For i-2i: methyl 2-(4-(5-chloro-2-nitrophenyl)-2-oxopyridin-1(2H)-yl)-3-(3-chlorophenyl)propanoate; m/z (ES) 447 $(MH)^+$.

For i-2k: methyl 2-(4-(5-chloro-2-nitrophenyl)-2-oxopyridin-1(2H)-yl)-3-(4-(trifluoromethoxy)phenyl)propanoate; m/z (ES) 497 $(MH)^+$.

For i-2l: 2-(4-(5-chloro-2-nitrophenyl)-2-oxopyridin-1(2H)-yl)-3-(4-fluorophenyl)propanoic acid; m/z (ES) 417 $(MH)^+$.

For i-2n: 2-(4-(5-chloro-2-nitrophenyl)-2-oxopyridin-1(2H)-yl)-3-(4-chlorophenyl)propanoic acid; m/z (ES) 433 $(MH)^+$.

For i-2o: 2-(4-(5-chloro-2-nitrophenyl)-2-oxopyridin-1(2H)-yl)-3-(3-chlorophenyl)propanoic acid; m/z (ES) 433 $(MH)^+$.

For i-2q: 2-(4-(5-chloro-2-nitrophenyl)-2-oxopyridin-1(2H)-yl)-3-(4-(trifluoromethoxy)phenyl)propanoic acid; m/z (ES) 483 $(MH)^+$.

Intermediate i-3

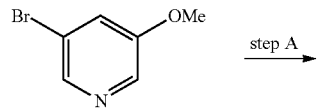

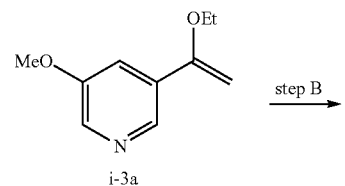

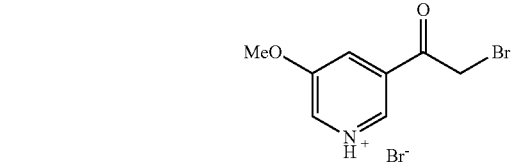

Step A: Preparation of 3-(1-ethoxyvinyl)-5-methoxypyridine (i-3a)

To a degassed stirred suspension of 3-bromo-5-methoxypyridine (1.50 g, 7.98 mmol) and [1,1'-bis(diphenylphosphino)ferrocene]dichloropalladium(II) (0.58 g, 0.80 mmol) in toluene (16 mL) was added tributyl(1-ethoxy)vinylstannane (3.2 mL, 9.58 mmol), and the resulting orangish mixture was heated to 110° C. After 1.5 h, the reaction was cooled to rt and diluted with EtOAc. The organics were filtered through a pad of Celite®, and the solid column was rinsed with EtOAc. The organics were dried ($Na_2SO_4$) and concentrated in vacuo. Purification of the crude residue by flash chromatography on silica gel (gradient elution; 0%-30% EtOAc/hexanes as eluent) afforded the title compound i-3a. m/z (ES) 180 $(MH)^+$.

Step B: Preparation of 3-(2-bromoacetyl)-5-methoxypyridin-1-ium bromide (i-3b)

N-Bromosuccinimide (0.63 g, 3.52 mmol) was added to a stirred solution of i-3a (0.63 g, 3.52 mmol) in THF (5.2 mL) and water (1.7 mL), and the resulting mixture was stirred at rt. After 20 min, the reaction mixture was partitioned between ether and water. The layers were separated, and the organic layer was washed with water and brine. HBr (33 wt. % in AcOH) was added dropwise to promote precipitation. The resulting slurry was filtered, and the filter cake was rinsed several times with ether to afford the title compound i-3b as a yellow-white solid. m/z (ES) 232 (MH)⁺.

TABLE i-3

| Compound | R |
|---|---|
| i-3c | 5-fluoro |
| i-3d | 5-chloro |
| i-3e | 5-methyl |
| i-3f | 5-cyano |
| i-3g | 4-trifluoromethyl |

Table i-3. Parent Ion m/z (MH)⁺ data for compounds
For i-3d: 3-(2-bromoacetyl)-5-chloropyridin-1-ium bromide; m/z (ES) 234 (MH)⁺.
For i-3e: 3-(2-bromoacetyl)-5-methylpyridin-1-ium bromide; m/z (ES) 214 (MH)⁺.
For i-3f: 3-(2-bromoacetyl)-5-cyanopyridin-1-ium bromide; m/z (ES) 225 (MH)⁺.
For 3g: 5-(2-bromoacetyl)-2-(trifluoromethyl)pyridin-1-ium bromide; m/z (ES) 268 (MH)⁺.

Intermediate i-4

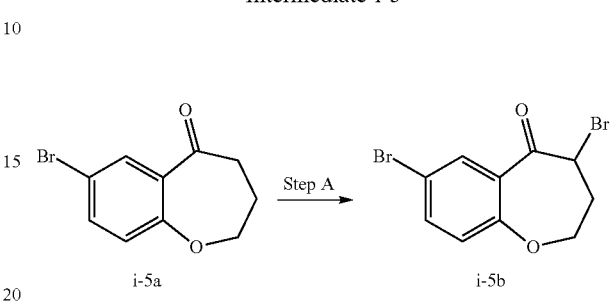

Step A: Preparation of 1-(1-ethoxyvinyl)-4-fluoro-2-nitrobenzene (i-4a) Intermediate i-4a was prepared following procedures similar to those reported above for the preparation of i-3a, substituting 2-bromo-5-fluoronitrobenzene for 3-bromo-5-methoxypyridine. m/z (ES) 235 (MNa)⁺.

Step B: Preparation of 2-bromo-1-(4-fluoro-2-nitrophenyl)ethanone (i-4b)

N-Bromosuccinimide (1.93 g, 10.9 mmol) was added to a stirred solution of i-4a (2.30 g, 10.9 mmol) in THF (16.0 mL) and water (5.7 mL), and the resulting mixture was stirred at rt. After 1 h, the reaction mixture was partitioned between EtOAc and water. The layers were separated, and the organic layer was washed with brine, dried (Na₂SO₄), filtered and concentrated. The crude residue was purified by flash chromatography on silica gel (gradient elution; 0%-20% EtOAc/hexanes as eluent) to afford the title compound i-4b as a yellow oil that solidified under vacuum. m/z (ES) 262 (MH)⁺.

Intermediate i-5

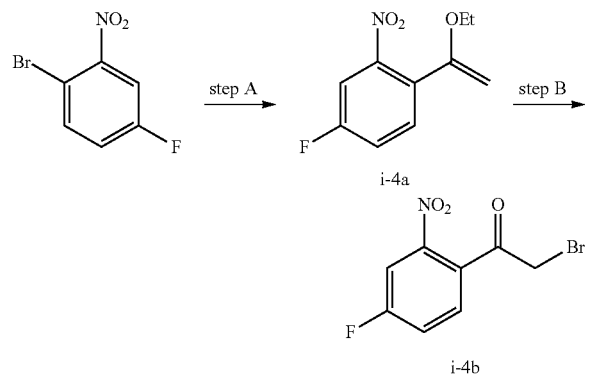

Step A: Preparation of 4,7-dibromo-3,4-dihydrobenzo[b]oxepin-5(2H)-one (i-5b)

Bromine (214 µL, 4.15 mmol) was added to a stirred solution of i-5a (1.00 g, 4.15 mmol) in ether (17 mL) at 0° C. After 30 min, the reaction was added to water, and the layers were separated. The organic layer was washed with water and brine, dried (Na₂SO₄), filtered and concentrated. The crude residue was purified by flash chromatography on silica gel (gradient elution; 0%-10% EtOAc/hexanes as eluent) to afford the title compound i-5b. m/z (ES) 319 (MH)⁺.

TABLE i-5

| Compound | R |
|---|---|
| i-5c | 6-bromo |
| i-5d | 6-iodo |
| i-5e | 7-bromo |
| i-5f | 6-diethylphosphono |
| i-5g | 7-methylcarbamoyl |

Table i-5. Parent Ion m/z (MH)⁺ data for compounds
For i-5c: 3,6-dibromochroman-4-one; m/z (ES) 305 (MH)⁺.
For i-5d: 3-bromo-6-iodochromane-4-one; m/z (ES) 353 (MH)⁺.
For i-5e: 3,7-dibromochroman-4-one; m/z (ES) 305 (MH)⁺.
For i-5f: diethyl (3-bromo-4-oxochroman-6-yl)phosphonate; m/z (ES) 363 (MH)⁺.
For i-5g: methyl (3-bromo-4-oxochroman-7-yl)carbamate; m/z (ES) 300 (MH)⁺.

EXAMPLES

Example 1

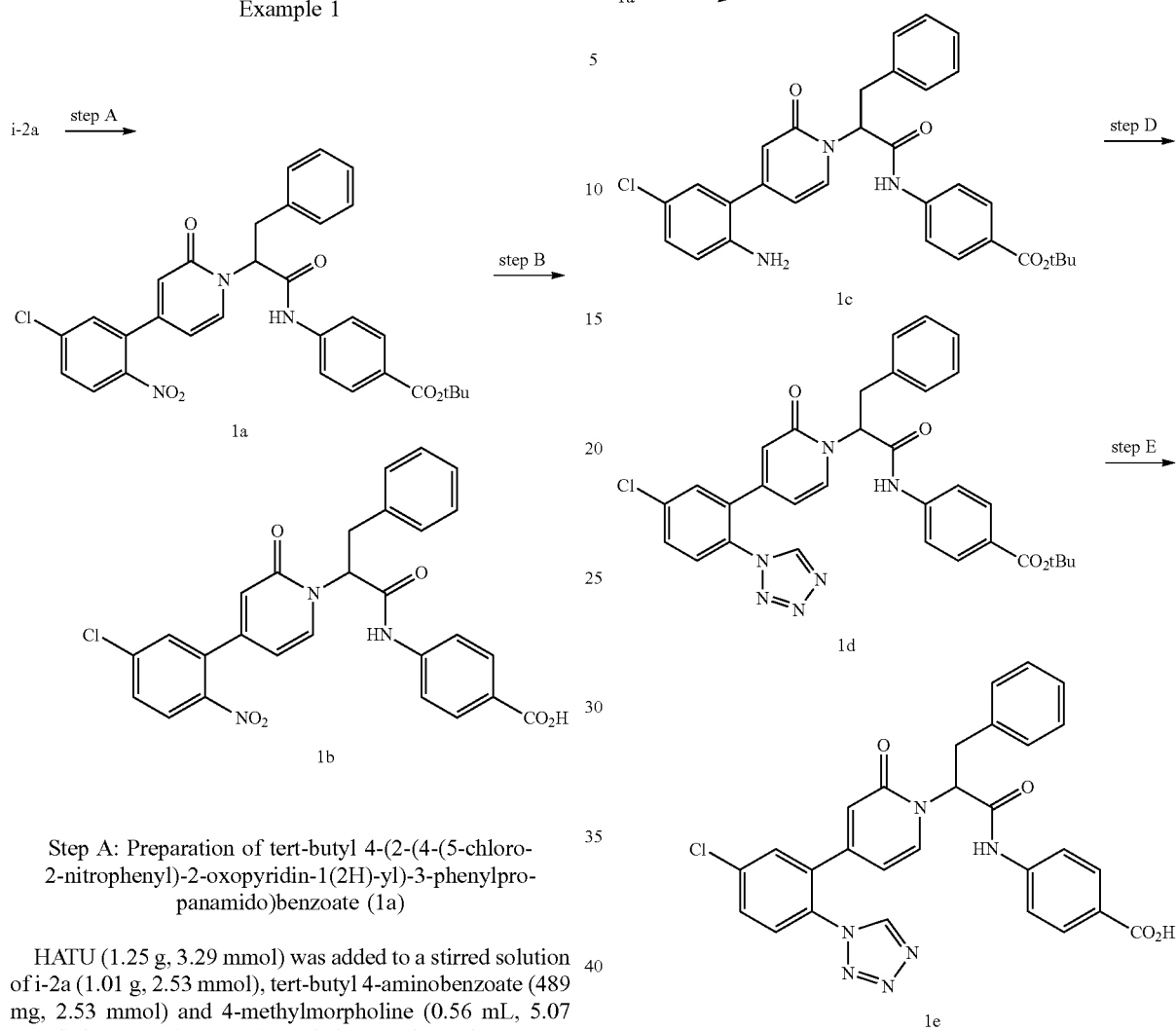

Step A: Preparation of tert-butyl 4-(2-(4-(5-chloro-2-nitrophenyl)-2-oxopyridin-1(2H)-yl)-3-phenylpropanamido)benzoate (1a)

HATU (1.25 g, 3.29 mmol) was added to a stirred solution of i-2a (1.01 g, 2.53 mmol), tert-butyl 4-aminobenzoate (489 mg, 2.53 mmol) and 4-methylmorpholine (0.56 mL, 5.07 mmol) in DMF (12.5 mL), and the reaction mixture was allowed to stir at rt. After 20 h, the reaction mixture was partitioned between EtOAc and water, and the layers were separated. The organic layer was washed with water and brine, dried (Na$_2$SO$_4$), filtered and concentrated. The resulting crude brown solid was dissolved in DCM, and hexanes was added to promote precipitation. The slurry was filtered, and the solid was rinsed with DCM and isolated to afford 1a as an off-white solid. Additional quantities of 1a were isolated from purification of the concentrated filtrate by flash chromatography on silica gel (gradient elution; 0%-50% EtOAc/hexanes as eluent). m/z (ES) 574 (MH)$^+$.

Step B: Preparation of 4-(2-(4-(5-chloro-2-nitrophenyl)-2-oxopyridin-1(2H)-yl)-3-phenylpropanamido)benzoic acid (1b)

Trifluoroacetic acid (160 µL) was added to a stirred solution of 1a (18 mg, 0.031 mmol) in DCM (0.48 mL) at rt. After 30 min, the reaction mixture was concentrated in vacuo, and the resulting crude residue was purified by preparative reverse phase HPLC on YMC Pack Pro C18 stationary phase (CH$_3$CN/H$_2$O as eluent, 0.05% TFA as modifier), and lyophilization of the purified fractions afforded the title compound 1b. m/z (ES) 518 (MH)$^+$.

Step C: Preparation of tert-butyl 4-(2-(4-(2-amino-5-chlorophenyl)-2-oxopyridin-1(2H)-yl)-3-phenylpropanamido)benzoate (1c)

Tin chloride dihydrate (5.66 g, 25.1 mmol) was added to a stirred suspension of 1a (4.80 g, 8.36 mmol) in EtOH (40 mL; 95% EtOH and 5% IPA), and the reaction mixture was heated to 35° C. After 16 h, the reaction was cooled to rt partially concentrated in vacuo. The resulting mixture was diluted with EtOAc and quenched via addition of 5N NaOH, which resulted in the formation of a white precipitate. The slurry was filtered through a Celite® column, and the column was rinsed with EtOAc. The organics were washed with water and brine, dried (Na$_2$SO$_4$), filtered and concentrated to afford 1c as a yellow solid. m/z (ES) 544 (MH)$^+$.

Step D: Preparation of tert-butyl 4-(2-(4-(5-chloro-2-(1H-tetrazol-1-yl)phenyl)-2-oxopyridin-1(2H)-yl)-3-phenylpropanamido)benzoate (1d)

Sodium azide (1.36 g, 21.0 mmol) was added to a stirred solution of 1c (3.80 g, 6.98 mmol) and trimethyl orthoformate (3.86 mL, 34.9 mmol) in AcOH (28 mL), and the resulting mixture was heated to 90° C. After 2.5 h, the reaction was cooled to 0° C., diluted with EtOAc and quenched via addition of satd. aq. NaHCO₃. The layers were separated, and the organics were washed with brine, dried (Na₂SO₄), filtered and concentrated. The resulting crude residue was purified by flash chromatography on silica gel (gradient elution; 0%-100% EtOAc/hexanes as eluent) to afford the title compound 1d as a white solid. m/z (ES) 619 (MNa)⁺.

Step E: Preparation of 4-(2-(4-(5-chloro-2-(1H-tetrazol-1-yl)phenyl)-2-oxopyridin-1(2H)-yl)-3-phenylpropanamido)benzoic acid (1e)

Trifluoroacetic acid (6.3 mL) was added to a stirred solution of 1d (1.70 g, 2.85 mmol) in DCM (12.5 mL) at rt. After 20 min, the reaction mixture was concentrated in vacuo, and the resulting crude residue was purified by preparative reverse phase HPLC on YMC Pack Pro C18 stationary phase (CH₃CN/H₂O as eluent, 0.05% TFA as modifier), and lyophilization of the purified fractions afforded the title compound 1e. m/z (ES) 563 (MNa)⁺.

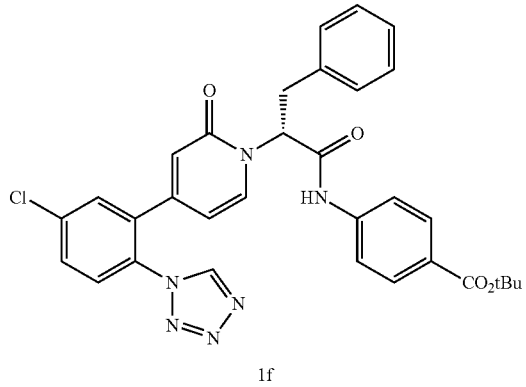

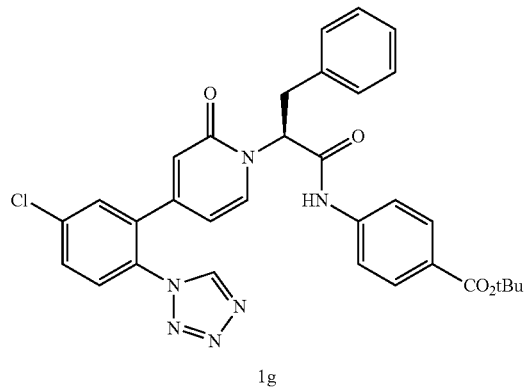

1f: (R)-tert-butyl 4-(2-(4-(5-chloro-2-(1H-tetrazol-1-yl)phenyl)-2-oxopyridin-1(2H)-yl)-3-phenylpropanamido)benzoate 1g: (S)-tert-butyl 4-(2-(4-(5-chloro-2-(1H-tetrazol-1-yl)phenyl)-2-oxopyridin-1(2H)-yl)-3-phenylpropanamido)benzoate Step F: Preparation of 1f and 1g Enantiomers 1f and 1g were separated using preparative normal phase chiral HPLC. A solution of 1d in methanol was injected onto a ChiralCel® OJ-H (available from Chiral Technologies, Inc., Exton, Pa.) semi-preparative (250×20 mm) HPLC column (eluting with 50% methanol and 0.2% diethylamine/CO₂ with a column temperature of 35° C. at 50 mL/min with UV detection at 220 nm). The enantiomers were separated with the faster eluting enantiomer 1f ($\alpha_D$ +52°, methanol) having a retention time of 2.99 min, and the slower eluting enantiomer 1g ($\alpha_D$ −40°, methanol) having a retention time of 4.85 min.

TABLE 1A

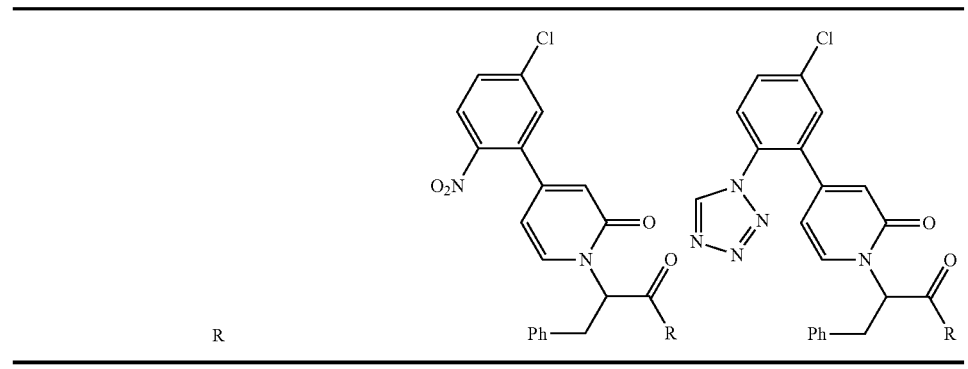

| R | 1Aa | 1Ba |
|---|-----|-----|

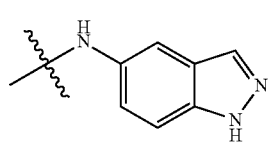 [SMILES: *Nc1ccc2[nH]ncc2c1]

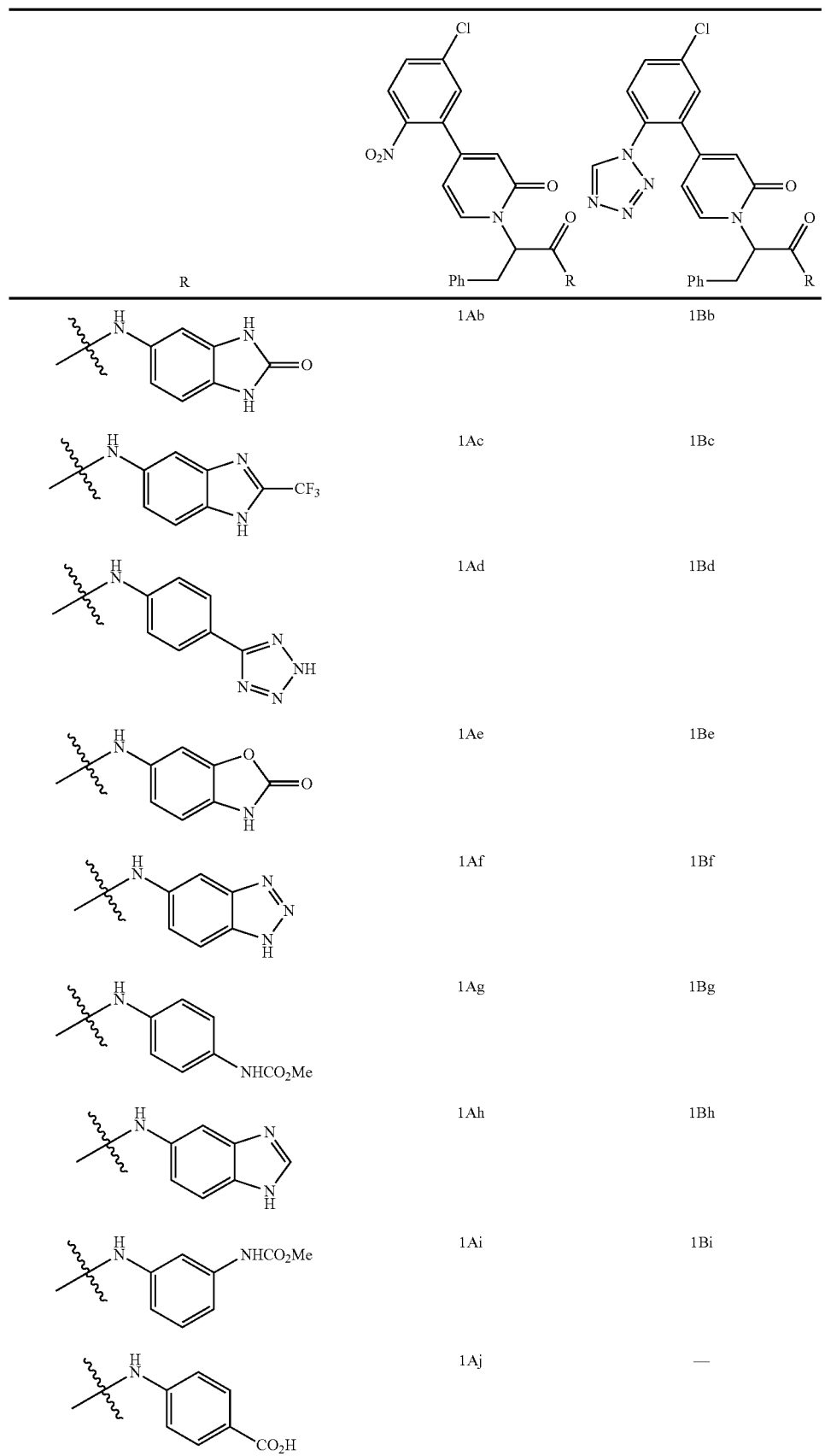

TABLE 1A-continued
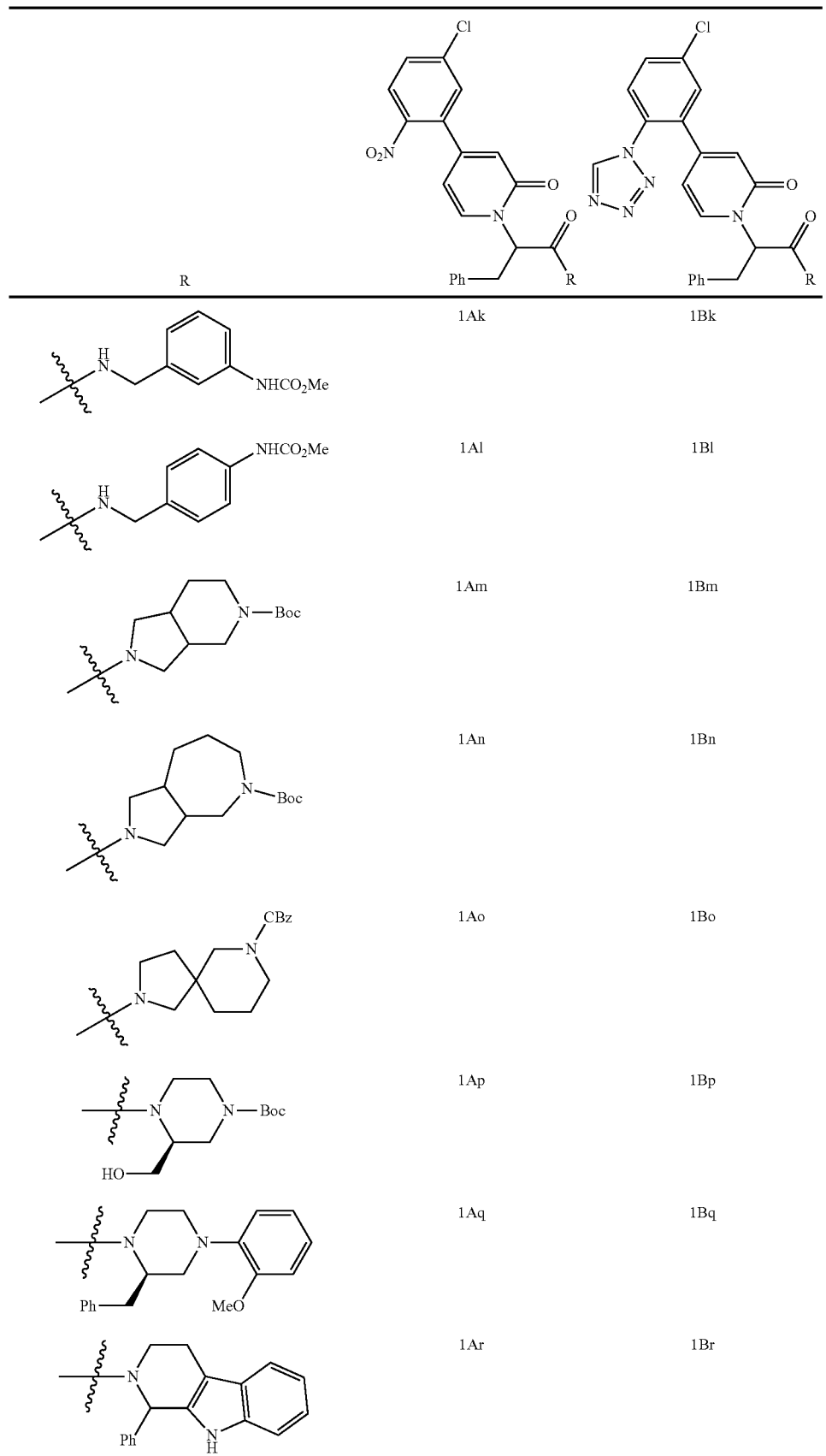
| R | 1Ak | 1Bk |
| --- | --- | --- |
| | 1Al | 1Bl |
| | 1Am | 1Bm |
| | 1An | 1Bn |
| | 1Ao | 1Bo |
| | 1Ap | 1Bp |
| | 1Aq | 1Bq |
| | 1Ar | 1Br |

TABLE 1A-continued
| R | | | |
|---|---|---|---|
| 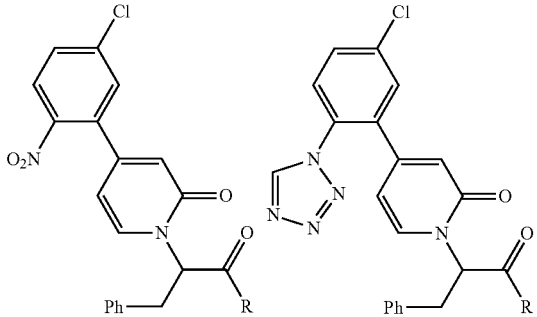 | 1As | 1Bs | |
|  | 1At | 1Bt | |
| 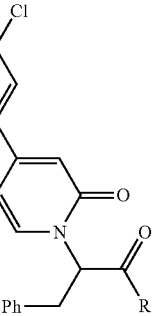 | 1Au | 1Bu | |
| 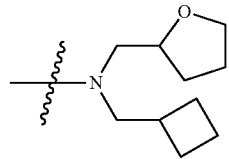 [SMILES: *N(CC1CCC1)CC1CCCO1] | 1Av | 1Bv | |
|  | 1Aw | 1Bw | |
|  | 1Ax | 1Bx | |
| 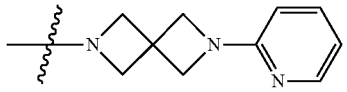 | 1Ay | 1By | |
|  | 1Az | 1Bz | |

TABLE 1A-continued

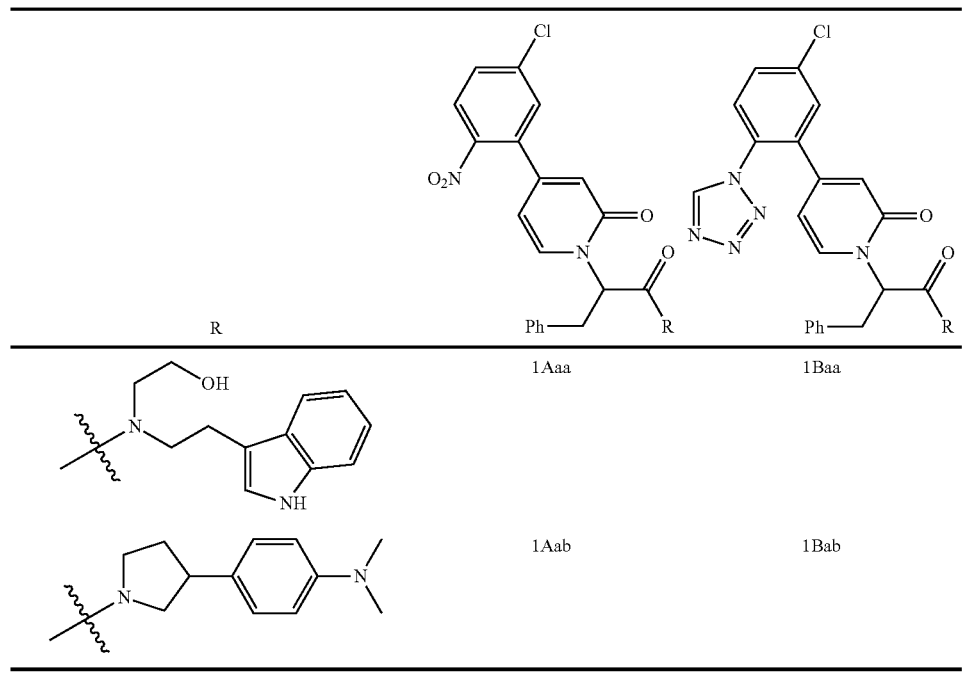

Table 1A. Parent Ion m/z (MH)+ data for compounds

For 1Aa: 2-(4-(5-chloro-2-nitrophenyl)-2-oxopyridin-(2H)-yl)-N-(1H-indazol-5-yl)-3-phenylpropanamide; m/z (ES) 514 (MH)+.

For 1Ab: 2-(4-(5-chloro-2-nitrophenyl)-2-oxopyridin-1(2H)-yl)-N-(2-oxo-2,3-dihydro-1H-benzo[d]imidazol-5-yl)-3-phenylpropanamide; m/z (ES) 530 (MH)+.

For 1Ac: 2-(4-(5-chloro-2-nitrophenyl)-2-oxopyridin-(2H)-yl)-3-phenyl-N-(2-(trifluoromethyl)-1H-benzo[d]imidazol-5-yl)propanamide; m/z (ES) 582 (MH)+.

For 1Ad: N-(4-(2H-tetrazol-5-yl)phenyl)-2-(4-(5-chloro-2-nitrophenyl)-2-oxopyridin-1(2H)-yl)-3-phenylpropanamide; m/z (ES) 542 (MH)+.

For 1Ae: 2-(4-(5-chloro-2-nitrophenyl)-2-oxopyridin-1(2H)-yl)-N-(2-oxo-2,3-dihydrobenzo[d]oxazol-6-yl)-3-phenylpropanamide; m/z (ES) 531 (MH)+.

For 1Af: N-(1H-benzo[d][1,2,3]triazol-5-yl)-2-(4-(5-chloro-2-nitrophenyl-2-oxopyridin-1(2)-yl)-3-phenylpropanamide; m/z (ES) 515 (MH)+.

For 1Ag: ethyl (4-(2-(4-(5-chloro-2-nitrophenyl)-2-oxopyridin-1(2H)-yl)-3-phenylpropanamido)phenyl)carbamate; m/z (ES) 582 (MNa)+.

For 1Ah: N-(1H-benzo[d]imidazol-6-yl)-2-(4-(5-chloro-2-nitrophenyl)-2-oxopyridin-1(2H)-yl)-3-phenylpropanamide; m/z (ES) 514 (MH)+.

For 1Ai: methyl (3-(2-(4-(5-chloro-2-nitrophenyl)-2-oxopyridin-1(2H)-yl)-3-(4-chlorophenyl)propanamido)phenyl)carbamate; m/z (ES) 547 (MH)+.

For 1Aj: 4-(2-(4-(5-chloro-2-nitrophenyl)-2-oxopyridin-1(2H)-yl)-3-phenylpropanamido)benzoic acid; m/z (ES) 518 (MH)+.

For 1Ak: methyl (3-((2-(4-(5-chloro-2-nitrophenyl)-2-oxopyridin-(2H)-yl)-3-phenylpropanamido)methyl)phenyl)carbamate; m/z (ES) 561 (MH)+.

For 1Al: methyl (4-((2-(4-(5-chloro-2-nitrophenyl)-2-oxopyridin-1(2H)-yl)-3-phenylpropanamido)methyl)phenyl)carbamate; m/z (ES) 561 (MH)+.

For 1Am: tert-butyl 2-(2-(4-(5-chloro-2-nitrophenyl)-2-oxopyridin-1(2H)-yl)-3-phenylpropanoyl)hexahydro-1H-pyrrolo[3,4-c]pyridine-5(6H)-carboxylate; m/z (ES) 607 (MH)+.

For 1An: tert-butyl 2-(2-(4-(5-chloro-2-nitrophenyl)-2-oxopyridin-1(2H)-yl)-3-phenylpropanoyl)octahydropyrrolo[3,4-c]azepine-5(1H)-carboxylate; m/z (ES) 621 (MH)+.

For 1Ao: benzyl 2-(2-(4-(5-chloro-2-nitrophenyl)-2-oxopyridin-1(2H)-yl)-3-phenylpropanoyl)-2,7-diazaspiro[4.5]decane-7-carboxylate; m/z (ES) 655 (MH)+.

For 1Ap: tert-butyl 4-(2-(4-(5-chloro-2-nitrophenyl)-2-oxopyridin-1(2H)-yl)-3-phenylpropanoyl)-3-(hydroxymethyl)piperazine-1-carboxylate; m/z (ES) 597 (MH)+.

For 1Aq: 1-(1-(2-benzyl-4-(2-methoxyphenyl)piperazin-1-yl)-1-oxo-3-phenylpropan-2-yl)-4-(5-chloro-2-nitrophenyl)pyridin-2(1H)-one; m/z (ES) 663 (MH)+.

For 1Ar: 4-(5-chloro-2-nitrophenyl)-1-(1-oxo-3-phenyl-1-(1-phenyl-3,4-dihydro-1H-pyrido[3,4-b]indol-2(9H)-yl)propan-2-yl)pyridin-2(1H)-one; m/z (ES) 629 (MH)+.

For 1As: 2-(4-(5-chloro-2-nitrophenyl)-2-oxopyridin-1(2H)-yl)-N-(cyclobutylmethyl)-3-phenyl-N-((tetrahydrofuran-2-yl)methyl)propanamide; m/z (ES) 550 (MH)+.

For 1 At: 4-(5-chloro-2-nitrophenyl)-1-(1-(3-(2,2-difluoro-1-hydroxyethyl)pyrrolidin-1-yl)-1-oxo-3-phenylpropan-2-yl)pyridin-2(1H)-one; m/z (ES) 532 (MH)+.

For 1Au: 4-(5-chloro-2-nitrophenyl)-1-(1-oxo-3-phenyl-1-(6-(pyridin-2-yl)-2,6-diazaspiro[3.3]heptan-2-yl)propan-2-yl)pyridin-2(1H)-one; m/z (ES) 556 (MH)+.

For 1Av: 1-(1-(4-((1H-benzo[d]imidazol-2-yl)methyl)-1,4-diazepan-1-yl)-1-oxo-3-phenylpropan-2-yl)-4-(5-chloro-2-nitrophenyl)pyridin-2(1H)-one; m/z (ES) 611 (MH)+.

For 1Aw: 4-(5-chloro-2-nitrophenyl)-1-(1-(4-((R)-3-hydroxypyrrolidin-1-yl)piperidin-1-yl)-1-oxo-3-phenylpropan-2-yl)pyridin-2(1H)-one; m/z (ES) 551 (MH)+.

For 1Ax: 4-(5-chloro-2-nitrophenyl)-1-(1-oxo-3-phenyl-1-(1-(2-(pyrrolidin-1-yl)ethyl)-6,7-dihydro-1H-pyrazolo[4,3-c]pyridin-5(4H)-yl)propan-2-yl)pyridin-2(1H)-one; m/z (ES) 601 (MH)+.

For 1Ay: 4-(5-chloro-2-nitrophenyl)-1-(1-oxo-3-phenyl-1-(3-(pyridin-3-yl)piperidin-1-yl)propan-2-yl)pyridin-2(1H)-one; m/z (ES) 543 (MH)+.

For 1Az: 4-(5-chloro-2-nitrophenyl)-1-(1-(3-isopropyl-5,6-dihydroimidazo[1,5-a]pyrazin-7(8H)-yl)-1-oxo-3-phenylpropan-2-yl)pyridin-2(1H)-one; m/z (ES) 546 (MH)+.

For 1Aaa: N-(2-(1H-indol-3-yl)ethyl)-2-(4-(5-chloro-2-nitrophenyl)-2-oxopyridin-1(2H)-yl)-N-(2-hydroxyethyl)-3-phenylpropanamide; m/z (ES) 585 (MH)+.

For 1Aab: 4-(5-chloro-2-nitrophenyl)-1-(1-(3-(4-(dimethylamino)phenyl)pyrrolidin-1-yl)-1-oxo-3-phenylpropan-2-yl)pyridin-2(1H)-one; m/z (ES) 571 (MH)+.

For 1Bb: 2-(4-(5-chloro-2-(1H-tetrazol-1-yl)phenyl)-2-oxopyridin-1(2H)-yl)-N-(2-oxo-2,3-dihydro-1H-benzo[d]imidazol-5-yl)-3-phenylpropanamide; m/z (ES) 553 (MH)+.

For 1Bh: N-(1H-benzo[d]imidazol-6-yl)-2-(4-(5-chloro-2-(1H-tetrazol-1-yl)phenyl)-2-oxopyridin-1(2H)-yl)-3-phenylpropanamide; m/z (ES) 537 (MH)+.

For 1Da: 4-(2-(4-(5-chloro-2-(1H-tetrazol-1-yl)phenyl)-2-oxopyridin-1(2H)-yl)-3-(4-fluorophenyl)propanamido)benzoic acid; m/z (ES) 559 (MH)+.

For 1Db: 4-(2-(4-(5-chloro-2-(1H-tetrazol-1-yl)phenyl)-2-oxopyridin-1(2H)-yl)-3-(3-fluorophenyl)propanamido)benzoic acid; m/z (ES) 559 (MH)+.

For 1De: 4-(2-(4-(5-chloro-2-(1H-tetrazol-1-yl)phenyl)-2-oxopyridin-1(2H)-yl)-3-(4-(trifluoromethoxy)phenyl)propanamido)benzoic acid; m/z (ES) 625 (MH)+.

For 1Ea: (S)-4-(2-(4-(5-chloro-2-(1H-tetrazol-1-yl)phenyl)-2-oxopyridin-1(2H)-yl)-3-(4-fluorophenyl)propanamido)benzoic acid; m/z (ES) 559 (MH)+.

For 1Eb: (S)-4-(2-(4-(5-chloro-2-(1H-tetrazol-1-yl)phenyl)-2-oxopyridin-1(2H)-yl)-3-(3-fluorophenyl)propanamido)benzoic acid; m/z (ES) 559 (MH)+.

For 1Ef: (S)-4-(2-(4-(5-chloro-2-(1H-tetrazol-1-yl)phenyl)-2-oxopyridin-1(2H)-yl)-3-phenylpropanamido)benzoic acid; m/z (ES) 541 (MH)+.

TABLE 1B

| R | | | | |
|---|---|---|---|---|
| 4-F-phenyl | 1Ca | 1Da | 1Ea | 1Fa |
| 3-F-phenyl | 1Cb | 1Db | 1Eb | 1Fb |
| 4-Cl-phenyl | 1Cc | 1Dc | 1Ec | 1Fc |
| 3-Cl-phenyl | 1Cd | 1Dd | 1Ed | 1Fd |
| 4-(CF3O)-phenyl | 1Ce | 1De | 1Ee | 1Fe |

Table 1B. Parent Ion m/z (MH)+ data for compounds

For 1Ca: 4-(2-(4-(5-chloro-2-nitrophenyl)-2-oxopyridin-1(2H)-yl)-3-(4-fluorophenyl)propanamido)benzoic acid; m/z (ES) 536 (MH)+.

For 1Cc: 4-(2-(4-(5-chloro-2-nitrophenyl)-2-oxopyridin-1(2H)-yl)-3-(4-chlorophenyl)propanamido)benzoic acid; m/z (ES) 552 (MH)+.

For 1Cd: 4-(2-(4-(5-chloro-2-nitrophenyl)-2-oxopyridin-1(2H)-yl)-3-(3-chlorophenyl)propanamido)benzoic acid; m/z (ES) 552 (MH)+.

For 1Fa: (R)-4-(2-(4-(5-chloro-2-(1H-tetrazol-1-yl)phenyl)-2-oxopyridin-1(2H)-yl)-3-(4-fluorophenyl)propanamido)benzoic acid; m/z (ES) 559 (MH)+.

For 1Fb: (R)-4-(2-(4-(5-chloro-2-(1H-tetrazol-1-yl)phenyl)-2-oxopyridin-1(2H)-yl)-3-(3-fluorophenyl)propanamido)benzoic acid; m/z (ES) 559 (MH)+.

For 1Ff: (R)-4-(2-(4-(5-chloro-2-(1H-tetrazol-1-yl)phenyl)-2-oxopyridin-1(2H)-yl)-3-phenylpropanamido)benzoic acid; m/z (ES) 541 (MH)+.

TABLE 1C

| R | 1Ga | 1Ha |
|---|---|---|

TABLE 1C-continued

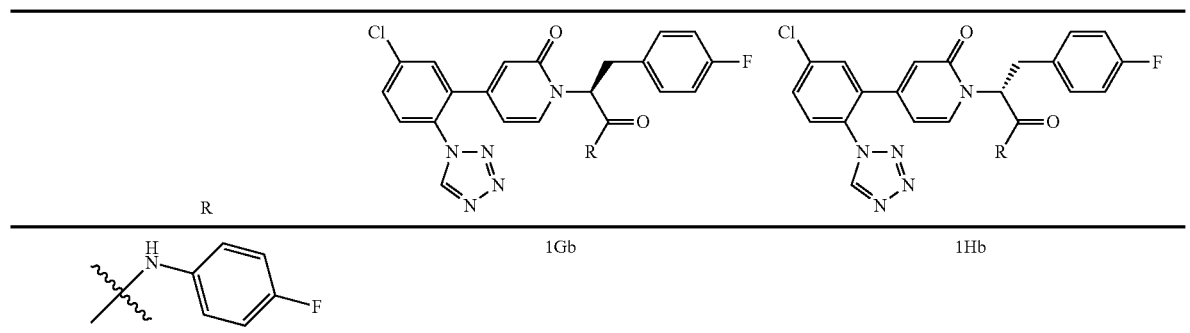

| 1Gb | 1Hb |
|---|---|

R

[structure: NH-phenyl-F]

Table 1C. Parent Ion m/z (MH)+ data for compounds

For 1Ga: (S)-ethyl (4-(2-(4-(5-chloro-2-(1H-tetrazol-1-yl)phenyl)-2-oxopyridin-1(2H)-yl)-3-(4-fluorophenyl)propanamido)phenyl)carbamate; m/z (ES) 624 (MNa)+.

For 1Gb: (S)-2-(4-(5-chloro-2-(1H-tetrazol-1-yl)phenyl)-2-oxopyridin-1(2H)-yl)-N,3-bis(4-fluorophenyl)propanamide; m/z (ES) 533 (MH)+.

For 1Ha: (R)-ethyl (4-(2-(4-(5-chloro-2-(1H-tetrazol-1-yl)phenyl)-2-oxopyridin-1(2H)-yl)-3-(4-fluorophenyl)propanamido)phenyl)carbamate; m/z (ES) 624 (MNa)+.

For 1Hb: (R)-2-(4-(5-chloro-2-(1H-tetrazol-1-yl)phenyl)-2-oxopyridin-1(2H)-yl)-N,3-bis(4-fluorophenyl)propanamide; m/z (ES) 533 (MH)+.

Example 2 i-1c →(step A)

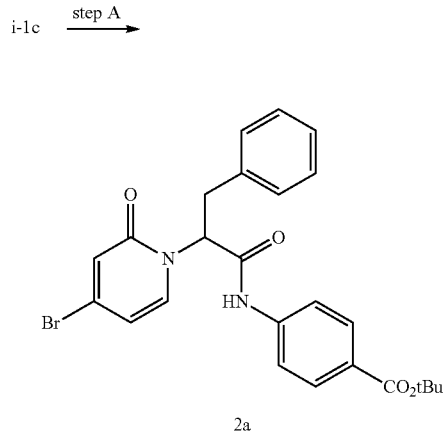

2a

↓ step B

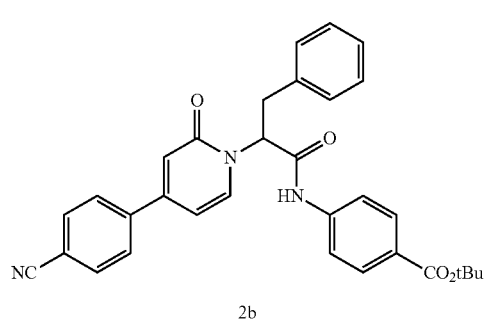

2b

↓ step C

[structure 2c with amidine and CO2tBu] → step D

[structure 2d with amidine and CO2H]

Step A: Preparation of tert-butyl 4-(2-(4-bromo-2-oxopyridin-1(2H)-yl)-3-phenylpropanamido)benzoate (2a)

Compound 2a was prepared following procedures similar to those described in Example 1, step A for the preparation of compound 1a, substituting i-1c for i-2a. m/z (ES) 497 (MH)+.

Step B: Preparation of tert-butyl 4-(2-(4-(4-cyanophenyl)-2-oxopyridin-1(2H)-yl)-3-phenylpropanamido)benzoate (2b)

Compound 2b was prepared following procedures similar to those described in Intermediate i-2, Step B for the preparation of compound i-2b, substituting 2a and (4-cyanophenyl)boronic acid for i-1b and (5-chloro-2-nitrophenyl)boronic acid. m/z (ES) 520 (MH)+.

Step C: Preparation of tert-butyl 4-(2-(4-(4-carbam-imidoylphenyl)-2-oxopyridin-1(2H)-yl)-3-phenyl-propanamido)benzoate (2c)

Lithium bis(trimethylsilyl)amide (144 μL of a 1.0 M THF solution, 0.144 mmol) was added to a stirred solution of 2b (15 mg, 0.029 mmol) in THF (0.29 mL), and the resulting mixture was allowed to stir at rt. After 20 min, the reaction was quenched via addition of methanol, and the solvent was removed in vacuo. The resulting crude residue was redissolved in THF, and 4M HCl in dioxane was added. After stirring at rt for 30 min, the mixture was concentrated in vacuo to afford the title compound 2c. m/z (ES) 537 (MH)+.

Step D: Preparation of 4-(2-(4-(4-carbamimidoyl-phenyl)-2-oxopyridin-1(2H)-yl)-3-phenylpropana-mido)benzoic acid (2d)

Compound 2d was prepared following procedures similar to those described in Example 1, step E for the preparation of compound 1e, substituting 2c for 1d. m/z (ES) 481 (MH)+.

TABLE 2

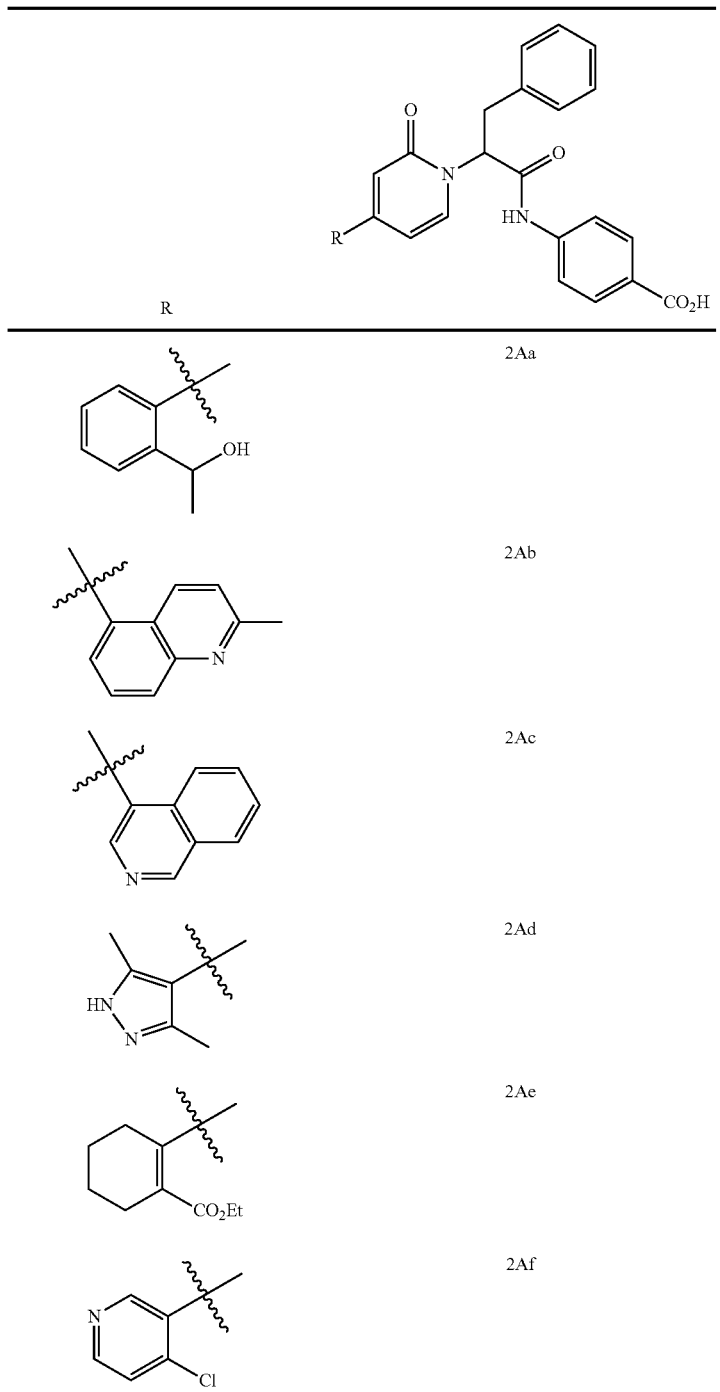

TABLE 2-continued

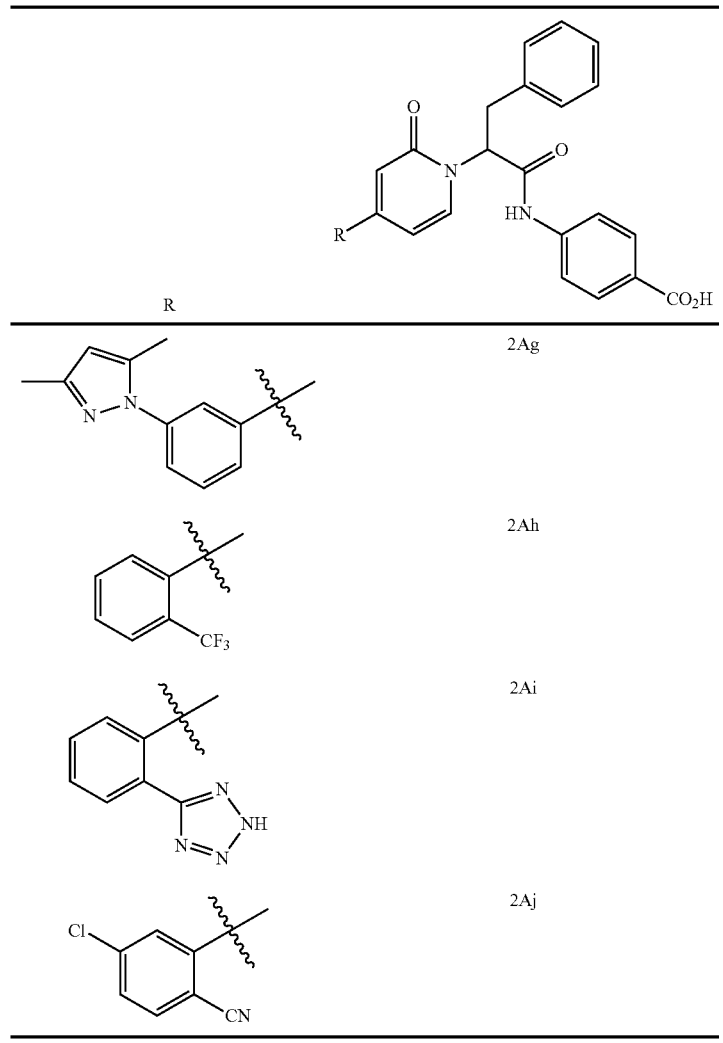

| R | |
|---|---|
| | 2Ag |
| | 2Ah |
| | 2Ai |
| | 2Aj |

Table 2. Parent Ion m/z (MH)+ data for compounds

For 2Aa: 4-(2-(4-(2-(1-hydroxyethyl)phenyl)-2-oxopyridin-1(2H)-yl)-3-phenylpropanamido)benzoic acid; m/z (ES) 483 (MH)+.

For 2Ab: 4-(2-(4-(2-methylquinolin-5-yl)-2-oxopyridin-1(2H)-yl)-3-phenylpropanamido)benzoic acid; m/z (ES) 504 (MH)+.

For 2Ac: 4-(2-(4-(isoquinolin-4-yl)-2-oxopyridin-1(2H)-yl)-3-phenylpropanamido)benzoic acid; m/z (ES) 490 (MH)+.

For 2Ad: 4-(2-(4-(3,5-dimethyl-1H-pyrazol-4-yl)-2-oxopyridin-1(2H)-yl)-3-phenylpropanamido)benzoic acid; m/z (ES) 457 (MH)+.

For 2Ae: 4-(2-(4-(2-(ethoxycarbonyl)cyclohex-1-en-1-yl)-2-oxopyridin-1(2H)-yl)-3-phenylpropanamido)benzoic acid; m/z (ES) 515 (MH)+.

For 2Af: 4-(2-(4-chloro-2'-oxo-[3,4'-bipyridin]-1'(2'H)-yl)-3-phenylpropanamido)benzoic acid; m/z (ES) 474 (MH)+.

For 2Ag: 4-(2-(4-(3-(3,5-dimethyl-1H-pyrazol-1-yl)phenyl)-2-oxopyridin-1(2H)-yl)-3-phenylpropanamido)benzoic acid; m/z (ES) 533 (MH)+.

For 2Ah: 4-(2-(2-oxo-4-(2-(trifluoromethyl)phenyl)pyridin-1(2H)-yl)-3-phenylpropanamido)benzoic acid; m/z (ES) 507 (MH)+.

For 2Ai: 4-(2-(4-(2-(2H-tetrazol-5-yl)phenyl)-2-oxopyridin-1(2H)-yl)-3-phenylpropanamido)benzoic acid; m/z (ES) 507 (MH)+.

For 2Aj: 4-(2-(4-(2-chloro-5-cyanophenyl)-2-oxopyridin-1(2H)-yl)-3-phenylpropanamido)benzoic acid; m/z (ES) 498 (MH)+.

Example 3

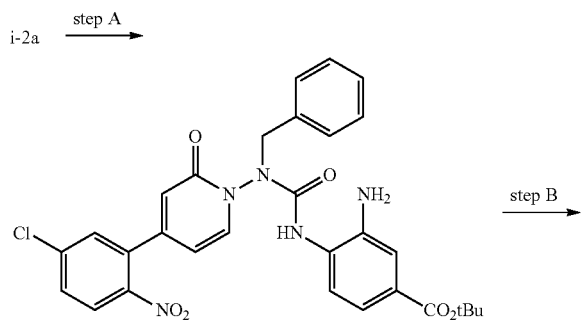

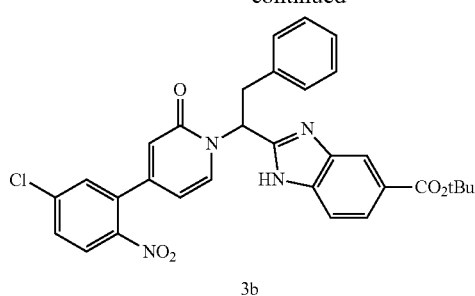

3b

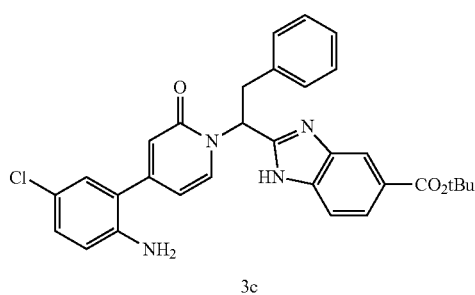

3c

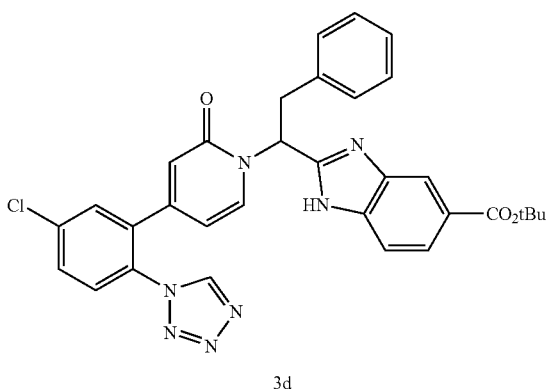

3d

Step A: Preparation of tert-butyl 3-amino-4-(2-(4-(5-chloro-2-nitrophenyl)-2-oxopyridin-1(2H)-yl)-3-phenylpropanamido)benzoate (3a)

Compound 3a was prepared following procedures similar to those described in Example 1, step A for the preparation of compound 1a, substituting tert-butyl 3,4-diaminobenzoate for tert-butyl 4-aminobenzoate. m/z (ES) 611 (MNa)+.

Step B: Preparation of tert-butyl 2-(1-(4-(5-chloro-2-nitrophenyl)-2-oxopyridin-1(2H)-yl)-2-phenylethyl)-1H-benzo[d]imidazole-5-carboxylate (3b)

A stirred solution of 3a (1.32 g, 2.24 mmol) in AcOH (30 mL) was heated to 70° C. After 2 h, the reaction mixture was cooled to rt and concentrated in vacuo. The resulting crude residue was partitioned between EtOAc and satd. aq. NaHCO₃. The layers were separated, and the organics were dried (Na₂SO₄), filtered and concentrated to afford 3b as a light brown foam. m/z (ES) 571 (MH)+.

Step C: Preparation of tert-butyl 2-(1-(4-(2-amino-5-chlorophenyl)-2-oxopyridin-1(2H)-yl)-2-phenylethyl)-1H-benzo[d]imidazole-5-carboxylate (3c)

Compound 3c was prepared following procedures similar to those described in Example 1, step C for the preparation of compound 1c, substituting compound 3b for compound 1a. m/z (ES) 541 (MH)+.

Step D: tert-butyl 2-(1-(4-(5-chloro-2-(1H-tetrazol-1-yl)phenyl)-2-oxopyridin-1(2H)-yl)-2-phenylethyl)-1H-benzo[d]imidazole-5-carboxylate (3d)

Compound 3d was prepared following procedures similar to those described in Example 1, step D for the preparation of compound 1d, substituting compound 3c for compound 1c. m/z (ES) 594 (MH)+.

Step E: Preparation of 3e and 3f

Enantiomers 3e and 3f were separated using preparative normal phase chiral HPLC. A solution of 3d in methanol was injected onto a ChiralCel® IC-H (available from Chiral Technologies, Inc., Exton, Pa.) semi-preparative (250×30 mm) HPLC column (eluting with 40% ethanol and 0.2% diethylamine/CO₂ with a column temperature of 35° C. at 70 mL/min with UV detection at 220 nm). The enantiomers were separated with the faster eluting enantiomer 3e ($\alpha_D$ −153°, methanol) having a retention time of 5.44 min, and the slower

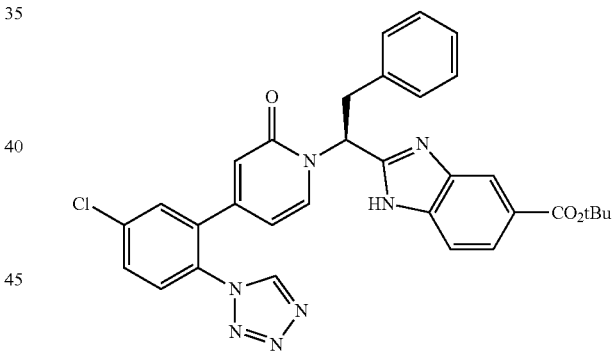

3e

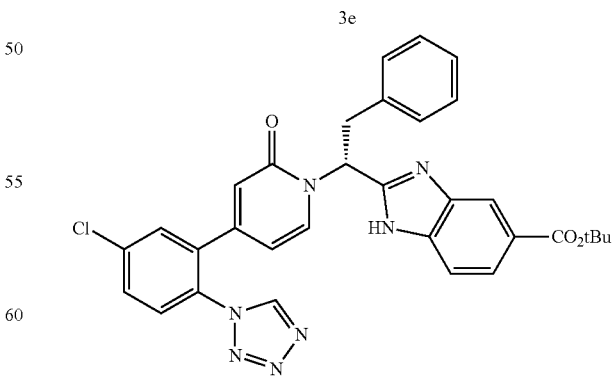

3f uting enantiomer 3f ($\alpha_D$ +153°, methanol) having a retention time of 6.28 min.

3e: (S)-tert-butyl 2-(1-(4-(5-chloro-2-(1H-tetrazol-1-yl)phenyl)-2-oxopyridin-1(2H)-yl)-2-phenylethyl)-1H-benzo[d]imidazole-5-carboxylate
3f: (R)-tert-butyl 2-(1-(4-(5-chloro-2-(1H-tetrazol-1-yl)phenyl)-2-oxopyridin-1(2H)-yl)-2-phenylethyl)-1H-benzo[d]imidazole-5-carboxylate

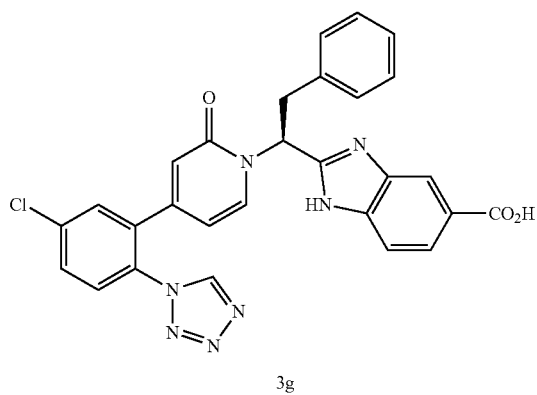

3g

Step F: Preparation of (S)-2-(1-(4-(5-chloro-2-(1H-tetrazol-1-yl)phenyl)-2-oxopyridin-1(2H)-yl)-2-phenylethyl)-1H-benzo[d]imidazole-5-carboxylic acid (3 g)

Trifluoroacetic acid (2.0 mL) was added to a stirred solution of 3e (367 mg, 0.618 mmol) in DCM (5.0 mL) at rt. After 2 h, the reaction mixture was concentrated in vacuo, and the resulting crude residue was purified by preparative reverse phase HPLC on YMC Pack Pro C18 stationary phase ($CH_3CN/H_2O$ as eluent, 0.1% formic acid as modifier), and lyophilization of the purified fractions afforded the title compound 3g. m/z (ES) 538 $(MH)^+$.

Table 3. Parent Ion m/z $(MH)^+$ data for compounds

For 3Aa: methyl 2-(1-(4-(5-chloro-2-(1H-tetrazol-1-yl)phenyl)-2-oxopyridin-1(2H)-yl)-2-phenylethyl)-1H-benzo[d]imidazole-5-carboxylate; m/z (ES) 552 $(MH)^+$.

For 3Ab: 2-(1-(4-(5-chloro-2-(1H-tetrazol-1-yl)phenyl)-2-oxopyridin-1(2H)-yl)-2-phenylethyl)-1H-benzo[d]imidazole-5-carboxylic acid; m/z (ES) 538 $(MH)^+$.

For 3Ae: 4-(5-chloro-2-(1H-tetrazol-1-yl)phenyl)-1-(1-(5-fluoro-1H-benzo[d]imidazol-2-yl)-2-(4-fluorophenyl)ethyl)pyridin-2(1H)-one; m/z (ES) 530 $(MH)^+$.

For 3Ba: (S)-methyl 2-(1-(4-(5-chloro-2-(1H-tetrazol-1-yl)phenyl)-2-oxopyridin-1(2H)-yl)-2-phenylethyl)-1H-benzo[d]imidazole-5-carboxylate; m/z (ES) 552 $(MH)^+$.

For 3Bc: (S)-ethyl 2-(1-(4-(5-chloro-2-(1H-tetrazol-1-yl)phenyl)-2-oxopyridin-1(2H)-yl)-2-(4-fluorophenyl)ethyl)-1H-benzo[d]imidazole-5-carboxylate; m/z (ES) 584 $(MH)^+$.

For 3Bd: (S)-2-(1-(4-(5-chloro-2-(1H-tetrazol-1-yl)phenyl)-2-oxopyridin-1(2H)-yl)-2-(4-fluorophenyl)ethyl)-1H-benzo[d]imidazole-5-carboxylic acid; m/z (ES) 556 $(MH)^+$.

For 3Be: (S)-4-(5-chloro-2-(1H-tetrazol-1-yl)phenyl)-1-(1-(5-fluoro-1H-benzo[d]imidazol-2-yl)-2-(4-fluorophenyl)ethyl)pyridin-2(1H)-one; m/z (ES) 530 $(MH)^+$.

For 3Bf: 1-(1-(5-bromo-1H-benzo[d]imidazol-2-yl)-2-(4-fluorophenyl)ethyl)-4-(5-chloro-2-(1H-tetrazol-1-yl)phenyl)pyridin-2(1H)-one; m/z (ES) 590 $(MH)^+$.

For 3Ca: (R)-methyl 2-(1-(4-(5-chloro-2-(1H-tetrazol-1-yl)phenyl)-2-oxopyridin-1(2H)-yl)-2-phenylethyl)-1H-benzo[d]imidazole-5-carboxylate; m/z (ES) 552 $(MH)^+$.

For 3Cb: (R)-2-(1-(4-(5-chloro-2-(1H-tetrazol-1-yl)phenyl)-2-oxopyridin-1(2H)-yl)-2-phenylethyl)-1H-benzo[d]imidazole-5-carboxylic acid; m/z (ES) 538 $(MH)^+$.

For 3Cc: (R)-ethyl 2-(1-(4-(5-chloro-2-(1H-tetrazol-1-yl)phenyl)-2-oxopyridin-1(2H)-yl)-2-(4-fluorophenyl)ethyl)-1H-benzo[d]imidazole-5-carboxylate; m/z (ES) 584 $(MH)^+$.

For 3Ce: (R)-4-(5-chloro-2-(1H-tetrazol-1-yl)phenyl)-1-(1-(5-fluoro-1H-benzo[d]imidazol-2-yl)-2-(4-fluorophenyl)ethyl)pyridin-2(1H)-one; m/z (ES) 530 $(MH)^+$.

TABLE 3

| R | R' | | | |
|---|---|---|---|---|
| H | CO2Me | 3Aa | 3Ba | 3Ca |
| H | CO2H | 3Ab | — | 3Cb |
| F | CO2Et | 3Ac | 3Bc | 3Cc |
| F | CO2H | 3Ad | 3Bd | 3Cd |
| F | F | 3Ae | 3Be | 3Ce |
| F | Br | 3Af | 3Bf | 3Cf |

Example 4

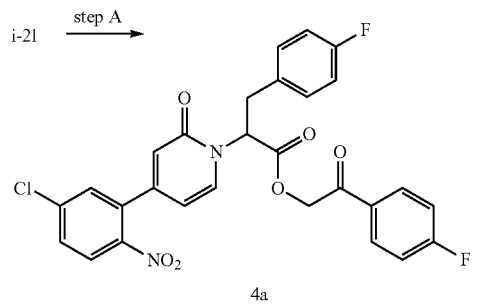

4a

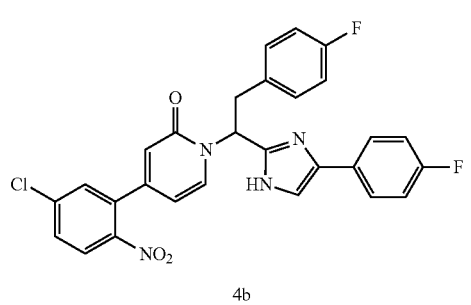

4b

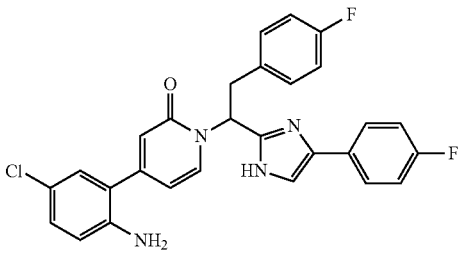

4c

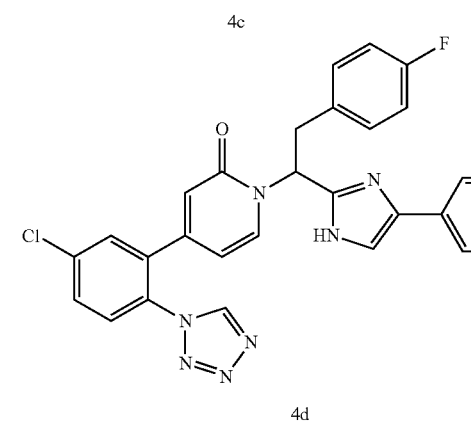

4d

Step A: Preparation of 2-(4-fluorophenyl)-2-oxoethyl 2-(4-(5-chloro-2-nitrophenyl)-2-oxopyridin-1(2H)-yl)-3-(4-fluorophenyl)propanoate (4a)

Cesium carbonate (469 mg, 1.44 mmol) was added to a stirred solution of i-21 (200 mg, 0.480 mmol) and 2-bromo-1-(4-fluorophenyl)ethanone (104 mg, 0.480 mmol) in DCE (3.2 mL), and the resulting mixture was heated to 60° C. After 4 h, the reaction was cooled to rt, and partitioned between DCM and water. The layers were separated, and the organics were washed with brine, dried (Na$_2$SO$_4$), filtered, and concentrated in vacuo to afford the title compound 4a. m/z (ES) 553 (MH)$^+$.

Step B: Preparation of 4-(5-chloro-2-nitrophenyl)-1-(2-(4-fluorophenyl)-1-(4-(4-fluorophenyl)-1H-imidazol-2-yl)ethyl)pyridin-2(1H)-one (4b)

Ammonium acetate (98 mg, 1.266 mmol) was added to a solution of 4a (175 mg, 0.317 mmol) in toluene (4.1 mL). The resulting mixture was heated in a microwave reactor at 150° C. for 1 h. After cooling to rt, the reaction was concentrated in vacuo, and the resulting crude residue was purified by flash chromatography on silica gel (gradient elution; 0%-50% EtOAc/hexanes as eluent) to afford the title compound 4b. m/z (ES) 533 (MH)$^+$.

Step C: Preparation of 4-(2-amino-5-chlorophenyl)-1-(2-(4-fluorophenyl)-1-(4-(4-fluorophenyl)-1H-imidazol-2-yl)ethyl)pyridin-2(1H)-one (4c)

Compound 4c was prepared following procedures similar to those described in Example 1, step C for the preparation of compound 1c, substituting compound 4b for compound 1a. m/z (ES) 503 (MH)$^+$.

Step D: Preparation of 4-(5-chloro-2-(1H-tetrazol-1-yl)phenyl)-1-(2-(4-fluorophenyl)-1-(4-(4-fluorophenyl)-1H-imidazol-2-yl)ethyl)pyridin-2(1H)-one (4d)

Compound 4d was prepared following procedures similar to those described in Example 1, step D for the preparation of compound 1d, substituting compound 4c for compound 1c. m/z (ES) 556 (MH)$^+$.

4b → step F

4e

4f

4e: (R)-4-(5-chloro-2-nitrophenyl)-1-(2-(4-fluorophenyl)-1-(5-(4-fluorophenyl)-1H-imidazol-2-yl)ethyl)pyridin-2(1H)-one 4f: (S)-4-(5-chloro-2-nitrophenyl)-1-(2-(4-fluorophenyl)-1-(5-(4-fluorophenyl)-1H-imidazol-2-yl)ethyl)pyridin-2(1H)-one

Step E: Preparation of 4e and 4f

Enantiomers 4e and 4f were separated using preparative normal phase chiral HPLC. A solution of 4b in methanol was injected onto a ChiralCel® IA-H (available from Chiral Technologies, Inc., Exton, Pa.) semi-preparative (250×30 mm) HPLC column (eluting with 75% (2:1) methanol: acetonitrile/$CO_2$ with a column temperature of 35° C. at 70 mL/min with UV detection at 220 nm). The enantiomers were separated with the faster eluting enantiomer 4e having a retention time of 8.0 min, and the slower eluting enantiomer 4f having a retention time of 17.0 min.

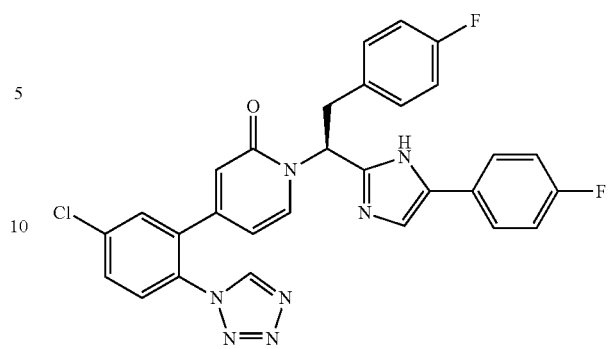

4g

Preparation of (S)-4-(5-chloro-2-(1H-tetrazol-1-yl)phenyl)-1-(2-(4-fluorophenyl)-1-(4-(4-fluorophenyl)-1H-imidazol-2-yl)ethyl)pyridin-2(1H)-one (4g)

Compound 4g was prepared from compound 4f following procedures similar to those described for the preparation of compound 1c in Example 1, Step C, substituting compound 4f for compound 1a. The product of this reaction was converted to compound 4g by substituting for compound 1c following procedures described in Example 1, Step D for the preparation of compound 1d. m/z (ES) 556 (MNa)$^+$. $\alpha_D$ −490, methanol.

TABLE 4

| R | R' | | | |
|---|---|---|---|---|
| H | pyridin-3-yl | 4Aa | 4Ba | 4Ca |
| F | pyridin-3-yl | 4Ae | 4Be | 4Ce |
| F | 4-fluorophenyl | 4Af | — | 4Cf |
| F | 3-fluorophenyl | 4Ag | 4Bg | 4Cg |
| F | 4-chlorophenyl | 4Ah | 4Bh | 4Ch |

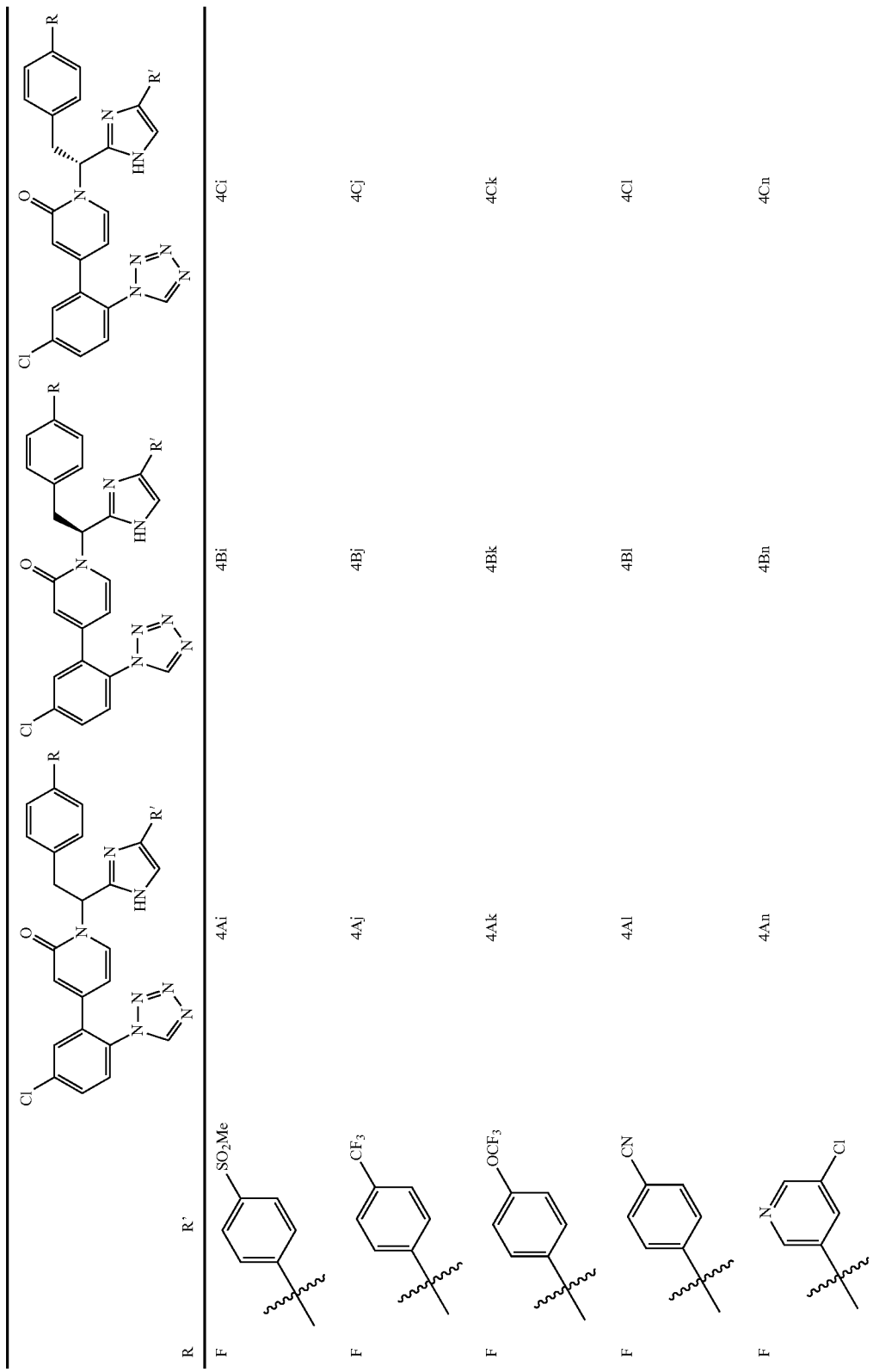
TABLE 4-continued

TABLE 4-continued

| R | R' | | | |
|---|---|---|---|---|
| | | 4Ao4An | 4Bo4Bn | 4Co4Cn |
| | | 4Ap4Ao | 4Bp4Bo | 4Cp4Co |
| FF | OMe (pyridine) | | | |
| | Cl (pyridine) | | | |
| FF | Me (pyridine) | | | |
| | OMe (pyridine) | | | |

TABLE 4-continued

| R | R' | | | |
|---|---|---|---|---|
| | | 4Aq4Ap | 4Bq4Bp | 4Cq4Cp |
| | | 4Ar4Aq | 4Br4Bq | 4Cr4Cq |
| | | 4Ar | 4Br | 4Cr |
| FF | 4-CN pyridyl | | | |
| FF | 4-CH₃ pyridyl | | | |
| F | 2-CH₃ pyridyl | | | |
| | 5-CN pyridyl | | | |
| | 2-CF₃ pyridyl | | | |

Table 4. Parent Ion m/z (MH)+ data for compounds

For 4Aa: 4-(5-chloro-2-(1H-tetrazol-1-yl)phenyl)-1-(2-phenyl-1-(4-(pyridin-3-yl)-1H-imidazol-2-yl)ethyl)pyridin-2 (1H)-one; m/z (ES) 539 (MH)+.

For 4Ag: 4-(5-chloro-2-(1H-tetrazol-1-yl)phenyl)-1-(2-(4-fluorophenyl)-1-(4-(3-fluorophenyl)-1H-imidazol-2-yl)ethyl)pyridin-2(1H)-one; m/z (ES) 556 (MH)+.

For 4Ah: 4-(5-chloro-2-(1H-tetrazol-1-yl)phenyl)-1-(1-(5-(4-chlorophenyl)-1H-imidazol-2-yl)-2-(4-fluorophenyl)ethyl)pyridin-2(1H)-one; m/z (ES) 572 (MH)+.

For 4Ai: 4-(5-chloro-2-(1H-tetrazol-1-yl)phenyl)-1-(2-(4-fluorophenyl)-1-(5-(4-(methylsulfonyl)phenyl)-1H-imidazol-2-yl)ethyl)pyridin-2(1H)-one; m/z (ES) 616 (MH)+.

For 4Aj: 4-(5-chloro-2-(1H-tetrazol-1-yl)phenyl)-1-(2-(4-fluorophenyl)-1-(5-(4-(trifluoromethyl)phenyl)-1H-imidazol-2-yl)ethyl)pyridin-2(1H)-one; m/z (ES) 606 (MH)+.

For 4Ak: 4-(5-chloro-2-(1H-tetrazol-1-yl)phenyl)-1-(2-(4-fluorophenyl)-1-(5-(4-(trifluoromethoxy)phenyl)-1H-imidazol-2-yl)ethyl)pyridin-2(1H)-one; m/z (ES) 622 (MH)+.

For 4Al: 4-(2-(1-(4-(5-chloro-2-(1H-tetrazol-1-yl)phenyl)-2-oxopyridin-1(2H)-yl)-2-(4-fluorophenyl)ethyl)-1H-imidazol-5-yl)benzonitrile; m/z (ES) 563 (MH)+.

For 4Ao: 4-(5-chloro-2-(1H-tetrazol-1-yl)phenyl)-1-(2-(4-fluorophenyl)-1-(5-(5-methoxypyridin-3-yl)-1H-imidazol-2-yl)ethyl)pyridin-2(1H)-one; m/z (ES) 569 (MH)+.

For 4Ar: 4-(5-chloro-2-(1H-tetrazol-1-yl)phenyl)-1-(2-(4-fluorophenyl)-1-(5-(6-(trifluoromethyl)pyridin-3-yl)-1H-imidazol-2-yl)ethyl)pyridin-2(1H)-one; m/z (ES) 607 (MH)+.

For 4Be: (S)-4-(5-chloro-2-(1H-tetrazol-1-yl)phenyl)-1-(2-(4-fluorophenyl)-1-(4-(pyridin-3-yl)-1H-imidazol-2-yl)ethyl)pyridin-2(1H)-one; m/z (ES) 539 (MH)+.

For 4Bh: (S)-4-(5-chloro-2-(1H-tetrazol-1-yl)phenyl)-1-(1-(5-(4-chlorophenyl)-1H-imidazol-2-yl)-2-(4-fluorophenyl)ethyl)pyridin-2(1H)-one; m/z (ES) 572 (MH)+.

For 4Bi: (S)-4-(5-chloro-2-(1H-tetrazol-1-yl)phenyl)-1-(2-(4-fluorophenyl)-1-(5-(4-(methylsulfonyl)phenyl)-1H-imidazol-2-yl)ethyl)pyridin-2(1H)-one; m/z (ES) 616 (MH)+.

For 4Bj: (S)-4-(5-chloro-2-(1H-tetrazol-1-yl)phenyl)-1-(2-(4-fluorophenyl)-1-(5-(4-(trifluoromethyl)phenyl)-1H-imidazol-2-yl)ethyl)pyridin-2(1H)-one; m/z (ES) 606 (MH)+.

For 4Bk: (S)-4-(5-chloro-2-(1H-tetrazol-1-yl)phenyl)-1-(2-(4-fluorophenyl)-1-(5-(4-(trifluoromethoxy)phenyl)-1H-imidazol-2-yl)ethyl)pyridin-2(1H)-one; m/z (ES) 622 (MH)+.

For 4Bl: (S)-4-(2-(1-(4-(5-chloro-2-(1H-tetrazol-1-yl)phenyl)-2-oxopyridin-1(2H)-yl)-2-(4-fluorophenyl)ethyl)-1H-imidazol-5-yl)benzonitrile; m/z (ES) 563 (MH)+.

For 4Bn: (S)-4-(5-chloro-2-(1H-tetrazol-1-yl)phenyl)-1-(1-(5-(5-chloropyridin-3-yl)-1H-imidazol-2-yl)-2-(4-fluorophenyl)ethyl)pyridin-2(1H)-one; m/z (ES) 573 (MH)+.

For 4Bo: (S)-4-(5-chloro-2-(1H-tetrazol-1-yl)phenyl)-1-(2-(4-fluorophenyl)-1-(5-(5-methoxypyridin-3-yl)-1H-imidazol-2-yl)ethyl)pyridin-2(1H)-one; m/z (ES) 569 (MH)+.

For 4Bp: (S)-4-(5-chloro-2-(1H-tetrazol-1-yl)phenyl)-1-(2-(4-fluorophenyl)-1-(5-(5-methylpyridin-3-yl)-1H-imidazol-2-yl)ethyl)pyridin-2(1H)-one; m/z (ES) 553 (MH)+.

For 4Bq: (S)-5-(2-(1-(4-(5-chloro-2-(1H-tetrazol-1-yl)phenyl)-2-oxopyridin-1(2H)-yl)-2-(4-fluorophenyl)ethyl)-1H-imidazol-5-yl)nicotinonitrile; m/z (ES) 564 (MH)+.

For 4Br: (S)-4-(5-chloro-2-(1H-tetrazol-1-yl)phenyl)-1-(2-(4-fluorophenyl)-1-(5-(6-(trifluoromethyl)pyridin-3-yl)-1H-imidazol-2-yl)ethyl)pyridin-2(1H)-one; m/z (ES) 607 (MH)+.

For 4Ce: (R)-4-(5-chloro-2-(1H-tetrazol-1-yl)phenyl)-1-(2-(4-fluorophenyl)-1-(4-(pyridin-3-yl)-1H-imidazol-2-yl)ethyl)pyridin-2(1H)-one; m/z (ES) 539 (MH)+.

For 4Cf: (R)-4-(5-chloro-2-(1H-tetrazol-1-yl)phenyl)-1-(2-(4-fluorophenyl)-1-(4-(4-fluorophenyl)-1H-imidazol-2-yl)ethyl)pyridin-2(1H)-one; m/z (ES) 556 (MH)+.

For 4Ch: (R)-4-(5-chloro-2-(1H-tetrazol-1-yl)phenyl)-1-(1-(5-(4-chlorophenyl)-1H-imidazol-2-yl)-2-(4-fluorophenyl)ethyl)pyridin-2(1H)-one; m/z (ES) 572 (MH)+.

For 4Ci: (R)-4-(5-chloro-2-(1H-tetrazol-1-yl)phenyl)-1-(2-(4-fluorophenyl)-1-(5-(4-(methylsulfonyl)phenyl)-1H-imidazol-2-yl)ethyl)pyridin-2(1H)-one; m/z (ES) 616 (MH)+.

For 4Cj: (R)-4-(5-chloro-2-(1H-tetrazol-1-yl)phenyl)-1-(2-(4-fluorophenyl)-1-(5-(4-(trifluoromethyl)phenyl)-1H-imidazol-2-yl)ethyl)pyridin-2(1H)-one; m/z (ES) 606 (MH)+.

For 4Cl: (R)-4-(2-(1-(4-(5-chloro-2-(1H-tetrazol-1-yl)phenyl)-2-oxopyridin-1(2H)-yl)-2-(4-fluorophenyl)ethyl)-1H-imidazol-5-yl)benzonitrile; m/z (ES) 563 (MH)+.

For 4Cn: (R)-4-(5-chloro-2-(1H-tetrazol-1-yl)phenyl)-1-(1-(5-(5-chloropyridin-3-yl)-1H-imidazol-2-yl)-2-(4-fluorophenyl)ethyl)pyridin-2(1H)-one; m/z (ES) 573 (MH)+.

For 4Co: (R)-4-(5-chloro-2-(1H-tetrazol-1-yl)phenyl)-1-(2-(4-fluorophenyl)-1-(5-(5-methoxypyridin-3-yl)-1H-imidazol-2-yl)ethyl)pyridin-2(1H)-one; m/z (ES) 569 (MH)+.

For 4Cp: (R)-4-(5-chloro-2-(1H-tetrazol-1-yl)phenyl)-1-(2-(4-fluorophenyl)-1-(5-(5-methylpyridin-3-yl)-1H-imidazol-2-yl)ethyl)pyridin-2(1H)-one; m/z (ES) 553 (MH)+.

For 4Cq: (R)-5-(2-(1-(4-(5-chloro-2-(1H-tetrazol-1-yl)phenyl)-2-oxopyridin-1(2H)-yl)-2-(4-fluorophenyl)ethyl)-1H-imidazol-5-yl)nicotinonitrile; m/z (ES) 564 (MH)+.

For 4Cr: (R)-4-(5-chloro-2-(1H-tetrazol-1-yl)phenyl)-1-(2-(4-fluorophenyl)-1-(5-(6-(trifluoromethyl)pyridin-3-yl)-1H-imidazol-2-yl)ethyl)pyridin-2(1H)-one; m/z (ES) 607 (MH)+.

Example 5

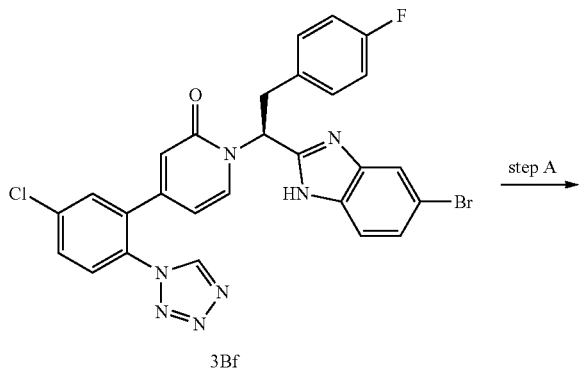

85

-continued

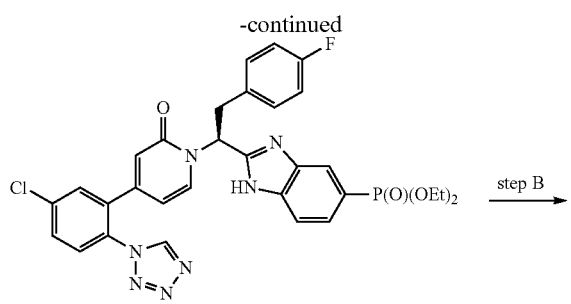

5a

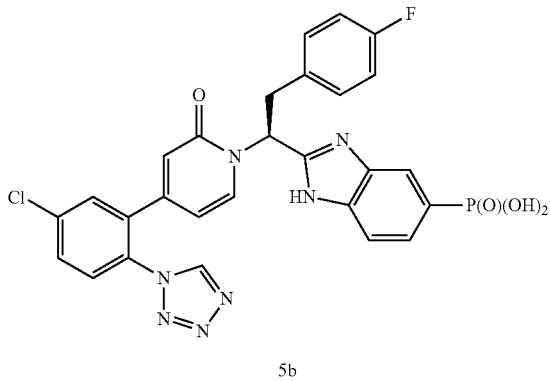

5b

Step A: Preparation of (S)-diethyl (2-(1-(4-(5-chloro-2-(1H-tetrazol-1-yl)phenyl)-2-oxopyridin-1(2H)-yl)-2-(4-fluorophenyl)ethyl)-1H-benzo[d]imidazol-5-yl)phosphonate (5a)

A degassed suspension of 3Bf (60 mg, 0.102 mmol), diethylphosphite (26 µL, 0.203 mmol), triethylamine (43 µL, 0.305 mmol), and [1,1'-bis(diphenylphosphino)ferrocene]dichloropalladium(II) (15 mg, 0.020 mmol) in dioxane (0.50 mL) was heated in a microwave reactor to 120° C. for 15 min. After cooling to rt, the reaction mixture was diluted with EtOAc and filtered through a column of Celite®, which was rinsed with additional portions of EtOAc. The combined organics were dried ($Na_2SO_4$), filtered and concentrated, and the resulting crude residue was purified by preparative reverse phase HPLC on YMC Pack Pro C18 stationary phase ($CH_3CN/H_2O$ as eluent, 0.05% TFA as modifier), and lyophilization of the purified fractions afforded the title compound 5a. m/z (ES) 648 $(MH)^+$.

Step B: Preparation of (S)-(2-(1-(4-(5-chloro-2-(1H-tetrazol-1-yl)phenyl)-2-oxopyridin-1(2H)-yl)-2-(4-fluorophenyl)ethyl)-1H-benzo[d]imidazol-5-yl)phosphonic acid (5b)

Bromotrimethylsilane (15 µL, 0.116 mmol) was added to a stirred solution of 5a (15 mg, 0.023 mmol) in DCM (0.23 mL), and the resulting mixture was allowed to stir at rt. After 72 h, the reaction was concentrated in vacuo, and the resulting crude residue was purified by preparative reverse phase HPLC on YMC Pack Pro C18 stationary phase ($CH_3CN/H_2O$ as eluent, 0.05% TFA as modifier), and

86 lyophilization of the purified fractions afforded the title compound 5b. m/z (ES) 592 $(MH)^+$.

Example 6 i-21 →step A→

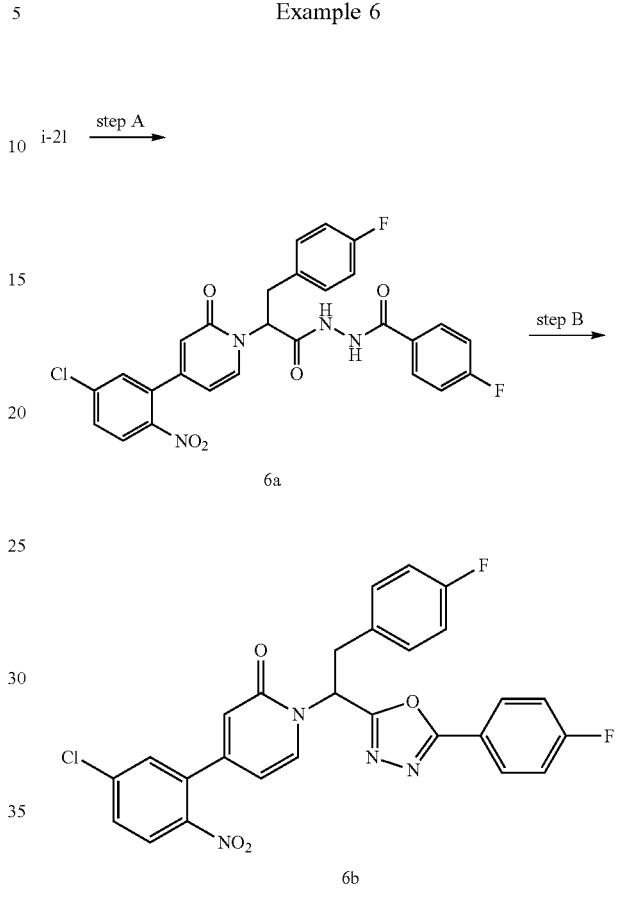

Step A: Preparation of N'-(2-(4-(5-chloro-2-nitrophenyl)-2-oxopyridin-1(2H)-yl)-3-(4-fluorophenyl)propanoyl)-4-fluorobenzohydrazide (6a)

Compound 6a was prepared following procedures similar to those described in Example 1, step A for the preparation of compound 1a, substituting 4-fluorobenzohydrazide for tert-butyl 4-aminobenzoate. m/z (ES) 575 $(MNa)^+$.

Step B: Preparation of 4-(5-chloro-2-nitrophenyl)-1-(2-(4-fluorophenyl)-1-(5-(4-fluorophenyl)-1,3,4-oxadiazol-2-yl)ethyl)pyridin-2(1H)-one (6b)

Burgess reagent was added to a stirred solution of 6a in THF, and the resulting mixture was heated to 65° C. After 2.5 h, the reaction was cooled to rt, diluted with water and extracted with EtOAc. The combined organics were washed with brine, dried ($Na_2SO_4$), filtered and concentrated. The resulting crude residue was purified by flash chromatography on silica gel (gradient elution; 0%-100% EtOAc/hexanes as eluent) to afford the title compound 6b as a yellow oil. m/z (ES) 535 $(MH)^+$.

i-2b →step C→

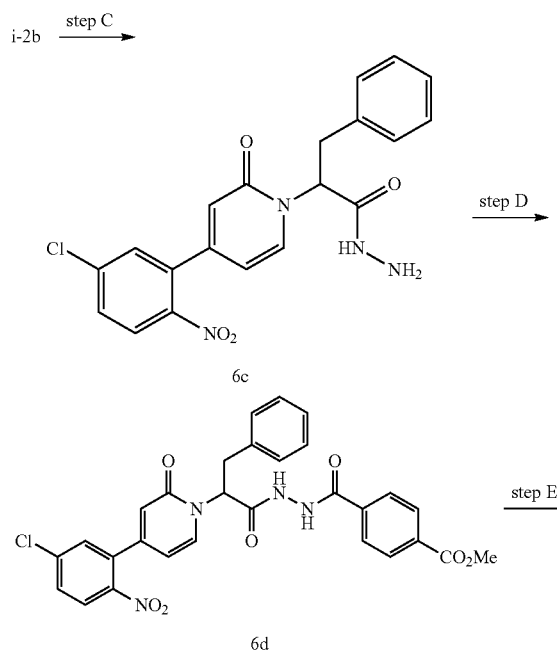

6c

6d

6e

Step C: Preparation of 2-(4-(5-chloro-2-nitrophenyl)-2-oxopyridin-1(2H)-yl)-3-phenylpropanehydrazide (6c)

Hydrazine monohydrate (80 μL, 1.65 mmol) was added to a stirred solution of i-2b (35 mg, 0.085 mmol) in ethanol (2.0 mL), and the resulting mixture was heated to reflux. After 1 h, the reaction was cooled to rt and concentrated in vacuo. The resulting crude residue was partitioned between EtOAc and water, and the layers were separated. The organics were washed w/brine, dried (Na$_2$SO$_4$), filtered and concentrated in vacuo to afford the title compound 6c. m/z (ES) 413 (MH)$^+$.

Step D: methyl 4-(2-(2-(4-(5-chloro-2-nitrophenyl)-2-oxopyridin-1(2H)-yl)-3-phenylpropanoyl)hydrazinocarbonyl)benzoate (6d)

Compound 6d was prepared following procedures similar to those described in Example 1, step A for the preparation of compound 1a, substituting 4-(methoxycarbonyl)benzoic acid for tert-butyl 4-aminobenzoate. m/z (ES) 575 (MH)$^+$.

Step E: Preparation of methyl 4-(5-(1-(4-(5-chloro-2-nitrophenyl)-2-oxopyridin-1(2H)-yl)-2-phenylethyl)-1,3,4-oxadiazol-2-yl)benzoate (6e)

Compound 6e was prepared following procedures similar to those described in Example 6, step B for the preparation of compound 6b, substituting compound 6d for compound 6b. m/z (ES) 557 (MH)$^+$.

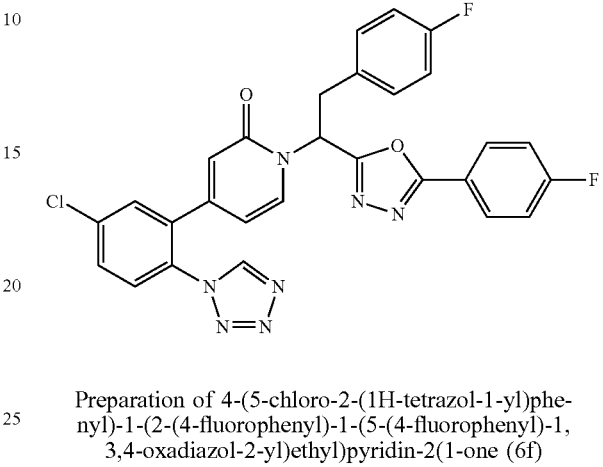

6f

Preparation of 4-(5-chloro-2-(1H-tetrazol-1-yl)phenyl)-1-(2-(4-fluorophenyl)-1-(5-(4-fluorophenyl)-1,3,4-oxadiazol-2-yl)ethyl)pyridin-2(1H)-one (6f)

Compound 6f was prepared from compound 6c following procedures similar to those described for the preparation of compound 1 in Example 1, Step C, substituting compound 6c for compound 1a. The product of this reaction was converted to compound 6f by substituting for compound 1c following procedures described in Example 1, Step D for the preparation of compound 1d. m/z (ES) 580 (MNa)$^+$.

6f →step F→

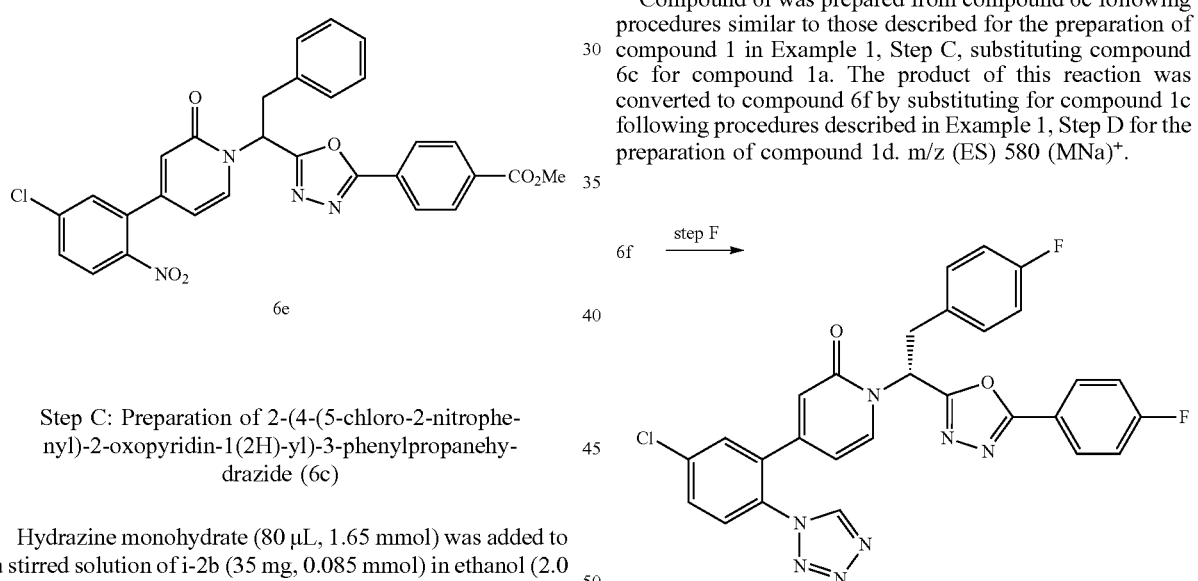

6g

6h

Step F: Preparation of 6g and 6h

Enantiomers 6g and 6h were separated using preparative normal phase chiral HPLC. A solution of 6f in methanol was injected onto a ChiralCel® AS-H (available from Chiral Technologies, Inc., Exton, Pa.) semi-preparative (25×2 mm) HPLC column (eluting with 12% methanol/CO$_2$ with a column temperature of 35° C. at 75 mL/min with UV detection at 220 nm). The enantiomers were separated with the faster eluting enantiomer 6g ($\alpha_D$ +160°, methanol) having a retention time of 10.75 min, and the slower eluting enantiomer 6h ($\alpha_D$ −145°, methanol) having a retention time of 12.09 min.

TABLE 6

| R | | | |
|---|---|---|---|
| 3-pyridyl | 6Aa | 6Ba | 6Ca |
| 4-Cl-phenyl | 6Ab | 6Bb | 6Cb |
| 4-CF3-phenyl | 6Ac | 6Bc | 6Cc |
| 4-(OCF3)-phenyl | 6Ad | 6Bd | 6Cd |

Table 6. Parent Ion m/z (MH)$^+$ data for compounds

For 6Aa: 4-(5-chloro-2-(1H-tetrazol-1-yl)phenyl)-1-(2-(4-fluorophenyl)-1-(5-(pyridin-3-yl)-1,3,4-oxadiazol-2-yl)ethyl)pyridin-2(1H)-one; m/z (ES) 541 (MH)$^+$.

For 6Ab: 4-(5-chloro-2-(1H-tetrazol-1-yl)phenyl)-1-(1-(5-(4-chlorophenyl)-1,3,4-oxadiazol-2-yl)-2-(4-fluorophenyl)ethyl)pyridin-2(1H)-one; m/z (ES) 596 (MNa)$^+$.

For 6Ba: (S)-4-(5-chloro-2-(1H-tetrazol-1-yl)phenyl)-1-(2-(4-fluorophenyl)-1-(5-(pyridin-3-yl)-1,3,4-oxadiazol-2-yl)ethyl)pyridin-2(1H)-one; m/z (ES) 541 (MH)$^+$.

For 6Bb: (S)-4-(5-chloro-2-(1H-tetrazol-1-yl)phenyl)-1-(1-(5-(4-chlorophenyl)-1,3,4-oxadiazol-2-yl)-2-(4-fluorophenyl)ethyl)pyridin-2(1H)-one; m/z (ES) 574 (MH)$^+$.

For 6Bc: (S)-4-(5-chloro-2-(1H-tetrazol-1-yl)phenyl)-1-(2-(4-fluorophenyl)-1-(5-(4-(trifluoromethoxy)phenyl)-1,3,4-oxadiazol-2-yl)ethyl)pyridin-2(1H)-one; m/z (ES) 608 (MH)$^+$.

For 6Bd: (S)-4-(5-chloro-2-(1H-tetrazol-1-yl)phenyl)-1-(2-(4-fluorophenyl)-1-(5-(4-(trifluoromethoxy)phenyl)-1,3,4-oxadiazol-2-yl)ethyl)pyridin-2(1H)-one; m/z (ES) 624 (MH)$^+$.

For 6ca: (R)-4-(5-chloro-2-(1H-tetrazol-1-yl)phenyl)-1-(2-(4-fluorophenyl)-1-(5-(pyridin-3-yl)-1,3,4-oxadiazol-2-yl)ethyl)pyridin-2(1H)-one; m/z (ES) 541 (MH)$^+$.

For 6Cb: (R)-4-(5-chloro-2-(1H-tetrazol-1-yl)phenyl)-1-(1-(5-(4-chlorophenyl)-1,3,4-oxadiazol-2-yl)-2-(4-fluorophenyl)ethyl)pyridin-2(1H)-one; m/z (ES) 574 (MH)$^+$.

For 6Cd: (R)-4-(5-chloro-2-(1H-tetrazol-1-yl)phenyl)-1-(2-(4-fluorophenyl)-1-(5-(4-(trifluoromethoxy)phenyl)-1,3,4-oxadiazol-2-yl)ethyl)pyridin-2(1H)-one; m/z (ES) 624 (MH)$^+$.

Example 7

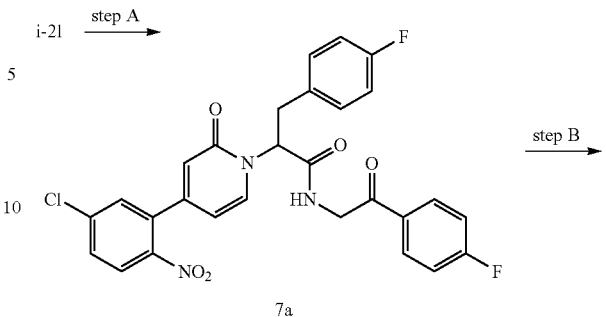

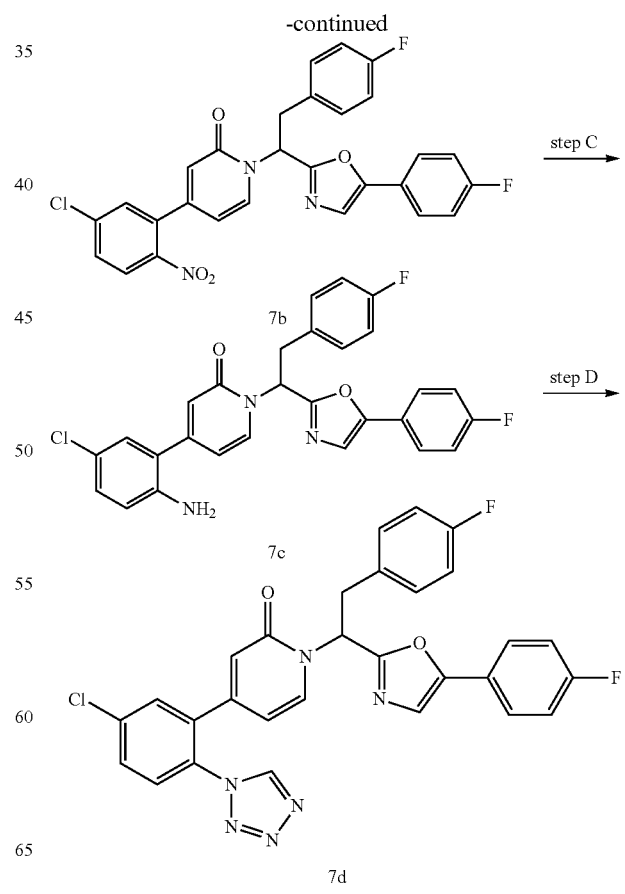

Step A: Preparation of 2-(4-(5-chloro-2-nitrophenyl)-2-oxopyridin-1(2H)-yl)-3-(4-fluorophenyl)-N-(2-(4-fluorophenyl)-2-oxoethyl)propanamide (7a)

Compound 7a was prepared following procedures similar to those described in Example 1, step A for the preparation of compound 1a, substituting 2-amino-1-(4-fluorophenyl)ethanone for tert-butyl 4-aminobenzoate. m/z (ES) 574 (MNa)+.

Step B: Preparation of 4-(5-chloro-2-nitrophenyl)-1-(2-(4-fluorophenyl)-1-(5-(4-fluorophenyl)oxazol-2-yl)ethyl)pyridin-2(1H)-one (7b)

Burgess reagent (65 mg, 0.272 mmol) was added to a stirred solution of 7a (75 mg, 0.136 mmol) in THF (0.68 mL), and the resulting mixture was heated to 65° C. After 2 h, the reaction mixture was partitioned between EtOAc and water. The layers were separated, and the organics were washed with brine, dried (Na$_2$SO$_4$), filtered and concentrated. The resulting crude residue was purified by flash chromatography on silica gel (gradient elution; 0%-100% EtOAc/hexanes as eluent) to afford the title compound 7b. m/z (ES) 534 (MH)+.

Step C: Preparation of 4-(2-amino-5-chlorophenyl)-1-(2-(4-fluorophenyl)-1-(5-(4-fluorophenyl)oxazol-2-yl)ethyl)pyridin-2(1H)-one (7c)

Compound 7c was prepared following procedures similar to those described in Example 1, step C for the preparation of compound 1c, substituting compound 7b for compound 1a.

Step D: Preparation of 4-(5-chloro-2-(1H-tetrazol-1-yl)phenyl)-1-(2-(4-fluorophenyl)-1-(5-(4-fluorophenyl)oxazol-2-yl)ethyl)pyridin-2(1H)-one (7d)

Compound 7d was prepared following procedures similar to those described in Example 1, step D for the preparation of compound 1d, substituting compound 7c for compound 1c. m/z (ES) 557 (MH)+.

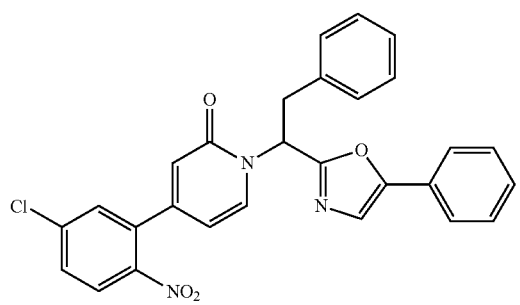

7e

For 7e: 4-(5-chloro-2-nitrophenyl)-1-(2-phenyl-1-(5-phenyloxazol-2-yl)ethyl)pyridin-2(1H)-one. m/z (ES) 498 (MH)+.

Example 8

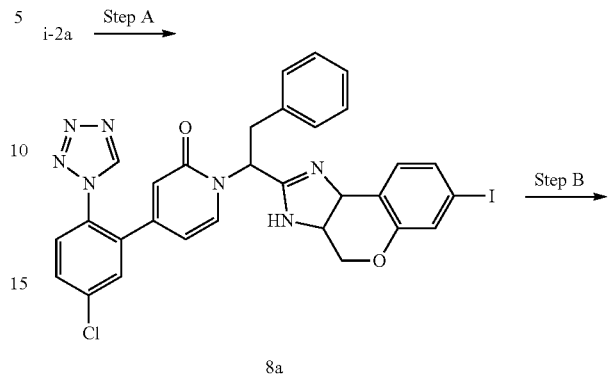

8a

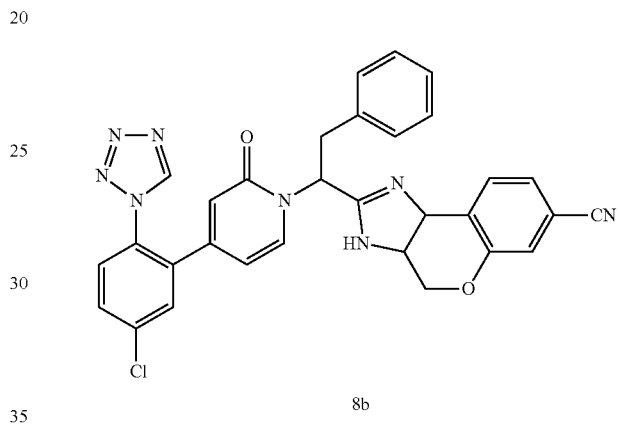

8b

Step A: Preparation of 4-(5-chloro-2-(1H-tetrazol-1-yl)phenyl)-1-(1-(7-iodo-3,3a,4,9b-tetrahydrochromeno[3,4-d]imidazol-2-yl)-2-phenylethyl)pyridin-2(1H)-one (8a)

Compound 8a was prepared following procedures similar to those described in Example 4, steps A and B for the preparation of compound 4b, substituting compound i-2a for compound i-2l, and i-5d for 2-bromo-1-(4-fluorophenyl)ethanone in Example 4, step A. m/z (ES) 674 (MH)+.

Step B: Preparation of 2-(1-(4-(5-chloro-2-(1H-tetrazol-1-yl)phenyl)-2-oxopyridin-1(2H)-yl)-2-phenylethyl)-3,3a,4,9b-tetrahydrochromeno[3,4-d]imidazole-7-carbonitrile (8b)

Compound i-2a (22 mg, 0.032 mmol), zinc cyanide (3.8 mg, 0.032 mmol), 1,1'-bis(diphenylphosphino)ferrocene (1.8 mg, 3.20 mol) and tris(dibenzylideneacetone)dipalladium(0) (5.8 mg, 6.4 mol) were suspended in DMF:water (0.21 mL of a 99:1 mixture). The reaction mixture was degassed and heated to 120° C. for 35 min. After cooling to rt, the reaction mixture was diluted with EtOAc and washed with brine. The organics were dried (Na$_2$SO$_4$), filtered and concentrated, and the resulting crude residue was purified by preparative reverse phase HPLC on YMC Pack Pro C18 stationary phase (CH$_3$CN/H$_2$O as eluent, 0.05% TFA as modifier), and lyophilization of the purified fractions afforded the title compound 8b. m/z (ES) 573 (MH)$^+$.

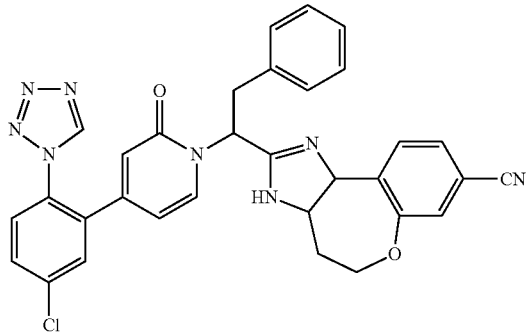

For 8c: 2-(1-(4-(5-chloro-2-(1H-tetrazol-1-yl)phenyl)-2-oxopyridin-1(2H)-yl)-2-phenylethyl)-3a,4,5,10b-tetrahydro-3H-benzo[2,3]oxepino[4,5-d]imidazole-8-carbonitrile; m/z (ES) 587 (MH)$^+$.

Factor XIa Assay

The effectiveness of compound of the present invention as inhibitors of Coagulation Factor XIa can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 150 mM NaCl, 5 mM CaCl$_2$, and 0.1% PEG 8000 (polyethylene glycol; JT Baker or Fisher Scientific). Determinations were made using purified human Factor XIa at a final concentration of 40 pM (Sekisui Diagnostics) and the synthetic substrate, Z-Gly-Pro-Arg-AFC, TFA salt (Sigma #C0980) at a concentration of 100 µM.

Activity assays were performed by diluting a stock solution of substrate at least tenfold to a final concentration ≤0.1 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m$/[S], [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in the following equation.

$V_o/V_i = 1 + [I]/K_i$

The activities shown by this assay indicate that the compounds of the invention may be therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels.

Factor XIa Inhibition

| Example | hFXIa Ki (nM) |
| --- | --- |
| 1Ag | 400 |
| 1Al | 340 |
| 1Aw | >10000 |
| 1Bc | <5 |
| 1Ea | 6 |
| 1Ef | <5 |
| 1Ff | 6 |
| 2d | 370 |
| 2Af | 7750 |
| 3g | <5 |
| 3Bc | 320 |
| 3Bd | <5 |
| 3Ca | 825 |
| 3Ce | 417 |
| 4Aa | <5 |
| 4Af | 154 |
| 4Ar | 275 |
| 4Bi | 39 |
| 4Bn | 18 |
| 4Bp | 54 |
| 4Cl | <5 |
| 4Co | 1035 |
| 5b | <5 |
| 6h | 240 |
| 6Aa | 280 |

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claim.

Compounds of the Formula (I) can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor XIa inhibitors can also be co-administered with suitable anticoagulants, including, but not limited to, other Factor XIa inhibitors, thrombin inhibitors, thrombin receptor antagonists, factor VIIa inhibitors, factor Xa inhibitors, factor IXa inhibitors, factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor XIa inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g., olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®, etc.); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin in immediate-release or controlled release forms, and particularly niacin in combination with a DP antagonist and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor XIa inhibitors of the invention in combination with other suitable anti-platelet agents, anticoagulation agents, or thrombolytic agents may be the same as those doses of Factor XIa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds in preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

What is claimed is:
1. A compound of Formula I

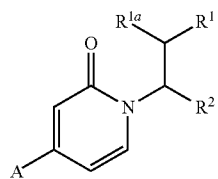

or a pharmaceutically acceptable salt thereof, where
A is
  1) 6-membered monocyclic carbocycle unsubstituted or mono-substituted with $R^3$ or di-substituted with $R^3$ and $R^4$, or
  2) 10-membered bicyclic carbocycle unsubstituted or substituted with $R^3$;
$R^1$ is
  1) $C_{1-6}$ alkyl, or
  2) 6-membered monocyclic carbocycle unsubstituted or substituted with $R^7$;
$R^{1a}$ is H or $CH_3$;
$R^2$ is benzimidazole, which is unsubstituted or substituted with $R^{16}$, $R^{17}$ or $R^{18}$;
$R^3$ is tetrazole;
$R^4$ is
  1) —C(NH)$NH_2$,
  2) —$NH_2$,
  3) Halogen,
  4) —$C_{1-6}$ alkyl, unsubstituted or substituted with —OH, F or —$NH_2$;
  5) —C(O)O$C_{1-6}$ alkyl,
  6) —$CF_3$,
  7) —$NO_2$,
  8) —CN, or
  9) —O$C_{1-6}$ alkyl;
$R^7$ is halogen, —$CF_3$ or —$OCF_3$;
$R^{10}$ is
  4-6-membered carbocycle either unsubstituted or substituted with —NHC(O)OH;

$R^{14}$ is $C_{1-6}$ alkyl unsubstituted or substituted with —OH, —$C_6H_5$, or —$((CH_2)_n—O)_m$—$CH_3$, where m is 1 or 2 and n is 1 or 2;
$R^{16}$ is and $R^{17}$ are each independently
  1) 6-membered carbocycle unsubstituted or substituted with $R^{20}$, or
  2) 6-membered carbocycle unsubstituted or substituted with $R^{19}$;
$R^{18}$ is
  1) —C(O)O$C_{1-6}$ alkyl,
  2) —C(O)OH,
  3) halogen,
  4) —P(O)(O$C_{1-6}$ alkyl)(O$C_{1-6}$ alkyl),
  5) —P(O)(OH)$_2$,
  6) —$SO_2C_{1-6}$ alkyl,
  7) —CN,
  8) —$CF_3$,
  9) —C(O)NH$R^{10}$,
  10) —NHC(O)O$R^{14}$,
  11) —NHC(O)$R^{10}$, or
  12) —P(O)(NH$C_{1-6}$ alkyl)(NH $C_{1-6}$ alkyl);
$R^{19}$ and $R^{20}$ are each independently
  1) halogen,
  2) —$SO_2C_{1-6}$ alkyl,
  3) —$CF_3$,
  4) —CN,
  5) —O$C_{1-6}$ alkyl,
  6) —$OCF_3$,
  7) —$C_{1-6}$ alkyl,
  8) —C(O)NH$R^{10}$,
  9) —NHC(O)$R^{10}$,
  10) —P(O)(OH)$_2$,
  11) —P(O)(O$C_{1-6}$ alkyl)(O$C_{1-6}$ alkyl), or
  12) —P(O)(NH$C_{1-6}$ alkyl)(NH $C_{1-6}$ alkyl).

2. A compound of claim 1 or a pharmaceutically acceptable salt thereof, where
A is
  1) 6-membered monocyclic carbocycle unsubstituted or mono-substituted with $R^3$ or di-substituted with $R^3$ and $R^4$, or
  2) 10-membered bicyclic carbocycle unsubstituted or substituted with $R^3$;
$R^1$ is
  1) $C_{1-6}$ alkyl, or
  2) 6-membered monocyclic carbocycle unsubstituted or substituted with $R^7$;
$R^{1a}$ is H or $CH_3$;
$R^2$ is benzimidazole, which is unsubstituted or substituted with $R^{18}$;
$R^3$ is tetrazole;
$R^4$ is
  1) —C(NH)$NH_2$,
  2) —$NH_2$,
  3) Halogen,
  4) —$C_{1-6}$ alkyl, unsubstituted or substituted with —OH, F or —$NH_2$,
  5) —C(O)O$C_{1-6}$ alkyl,
  6) —$CF_3$,
  7) —$NO_2$,
  8) —CN, or
  9) —O$C_{1-6}$ alkyl;
$R^7$ is halogen, —$CF_3$ or —$OCF_3$;
$R^{10}$ is
  4-6-membered carbocycle either unsubstituted or substituted with —NHC(O)OH;

$R^{14}$ is $C_{1-6}$ alkyl unsubstituted or substituted with —OH, —$C_6H_5$, or —$((CH_2)_n$—$O)_m$—$CH_3$, where m is 1 or 2 and n is 1 or 2;

$R^{18}$ is
1) —C(O)O$C_{1-6}$ alkyl,
2) —C(O)OH,
3) halogen,
4) —P(O)(O$C_{1-6}$ alkyl)(O$C_{1-6}$ alkyl),
5) —P(O)(OH)$_2$,
6) —SO$_2$$C_{1-6}$ alkyl,
7) —CN,
8) —CF$_3$,
9) —C(O)NHR$^{10}$,
10) —NHC(O)OR$^{14}$,
11) —NHC(O)R$^{10}$, or
12) —P(O)(NH$C_{1-6}$ alkyl)(NH $C_{1-6}$ alkyl).

3. A compound of claim 2 of formula Ia

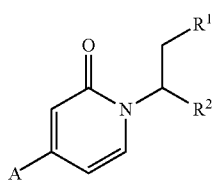

or a pharmaceutically acceptable salt thereof, where

A is
1) 6-membered monocyclic carbocycle unsubstituted or mono-substituted with $R^3$ or di-substituted with $R^3$ and $R^4$, or
2) 10-membered bicyclic carbocycle unsubstituted or substituted with $R^3$;

$R^1$ is
1) $C_{1-6}$ alkyl, or
2) 6-membered monocyclic carbocycle unsubstituted or substituted with $R^7$;

$R^2$ is benzimidazole, which is unsubstituted or substituted with $R^{18}$;

$R^3$ is tetrazole;

$R^4$ is —NO$_2$, $C_{1-6}$ alkyl, —CN, —NH$_2$, or —O$C_{1-6}$ alkyl;

$R^7$ is halogen, —CF$_3$ or —OCF$_3$;

$R^{10}$ is
4-6-membered carbocycle either unsubstituted or substituted with —NHC(O)OH;

$R^{14}$ is $C_{1-6}$ alkyl unsubstituted or substituted with —OH, —$C_6H_5$, or —$((CH_2)_n$—$O)_m$—$CH_3$, where m is 1 or 2 and n is 1 or 2;

$R^{18}$ is
1) —C(O)O$C_{1-6}$ alkyl,
2) —C(O)OH,
3) halogen,
4) —P(O)(O$C_{1-6}$ alkyl)(O$C_{1-6}$ alkyl),
5) —P(O)(OH)$_2$,
6) —SO$_2$$C_{1-6}$ alkyl,
7) —CN,
8) —CF$_3$,
9) —C(O)NHR$^{10}$,
10) —NHC(O)OR$^{14}$,
11) —NHC(O)R$^{10}$, or
12) —P(O)(NH$C_{1-6}$ alkyl)(NH $C_{1-6}$ alkyl).

4. A compound of claim 3, or a pharmaceutically acceptable salt thereof, wherein A is

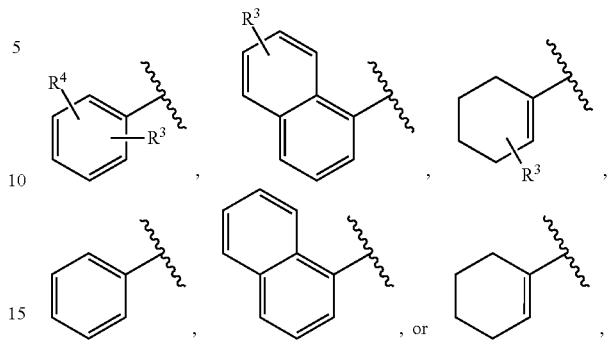

$R^1$ is

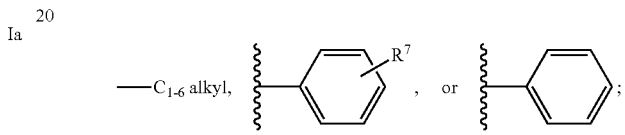

$R^2$ is

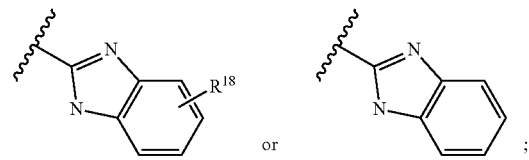

$R^3$ is

$R^4$ is
—NO$_2$, —CH$_3$, —CN, —NH$_2$, or —OCH$_3$, or $R^7$ is —Cl, F, or —OCF$_3$;

$R^{18}$ is —C(O)OCH$_3$, —C(O)OCH$_2$CH$_3$, —C(O)OH, —F, —P(O)(OCH$_2$CH$_3$)$_2$, —P(O)(OH)$_2$, —C(O)OC(CH$_3$)$_3$, —CN or —P(O)(NH$C_{1-6}$ alkyl)(NH$C_{1-6}$ alkyl).

5. A compound of claim 4, or a pharmaceutically acceptable salt thereof, wherein A is

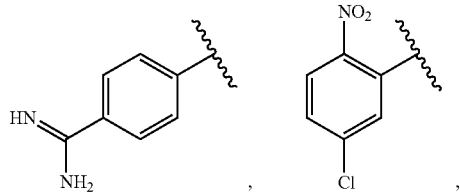

-continued

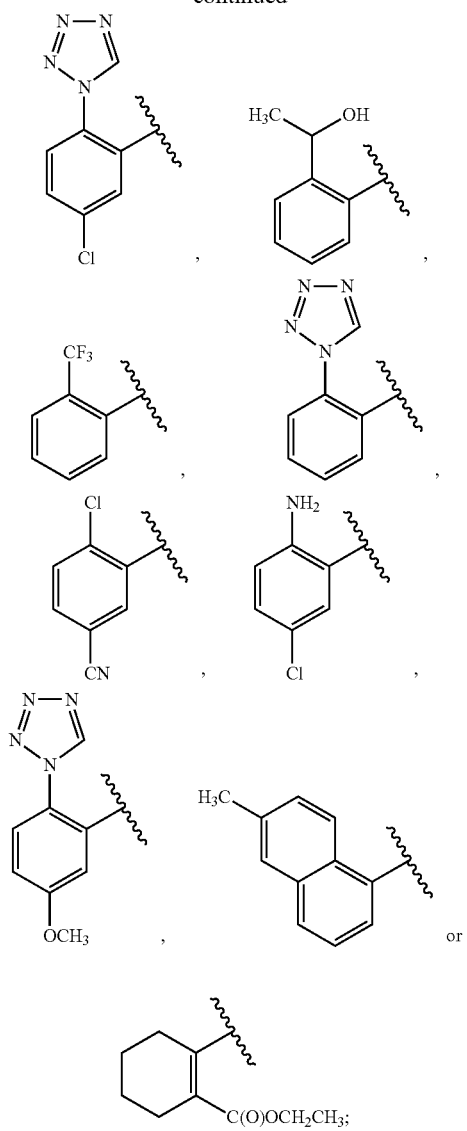

R¹ is

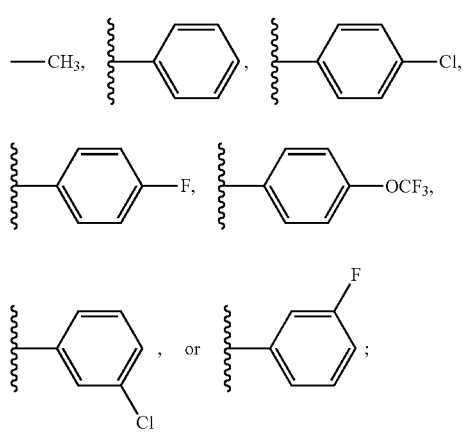

R² is

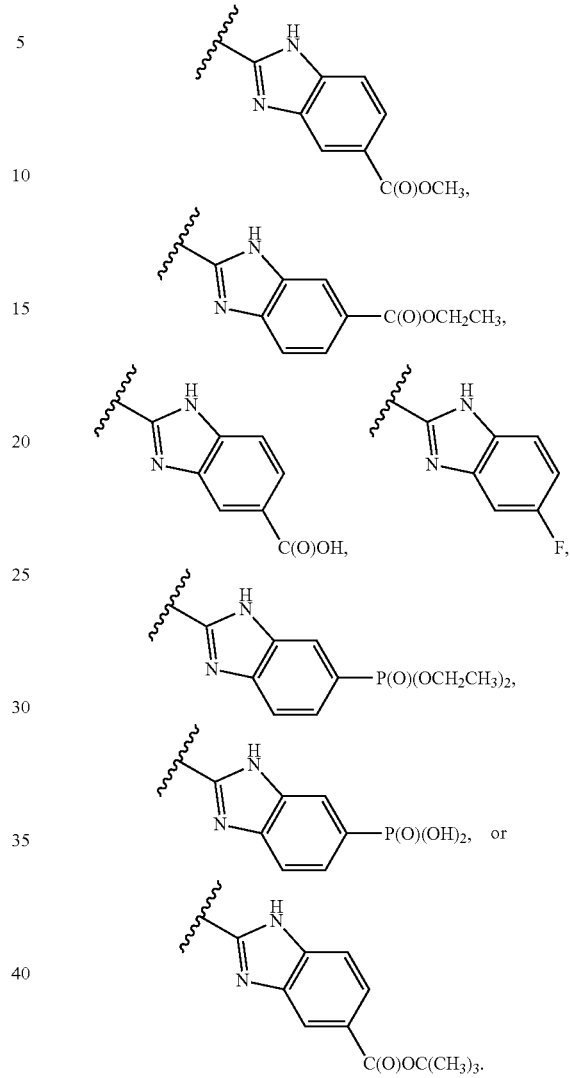

6. A compound, or a pharmaceutically acceptable salt thereof, which is
tert-butyl 2-(1-(4-(5-chloro-2-(1H-tetrazol-1-yl)phenyl)-2-oxopyridin-1(2H)-yl)-2-phenylethyl)-1H-benzo[d]imidazole-5-carboxylate,
(S)-tert-butyl 2-(1-(4-(5-chloro-2-(1H-tetrazol-1-yl)phenyl)-2-oxopyridin-1(2H)-yl)-2-phenylethyl)-1H-benzo[d]imidazole-5-carboxylate,
(R)-tert-butyl 2-(1-(4-(5-chloro-2-(1H-tetrazol-1-yl)phenyl)-2-oxopyridin-1(2H)-yl)-2-phenylethyl)-1H-benzo[d]imidazole-5-carboxylate,
(S)-2-(1-(4-(5-chloro-2-(1H-tetrazol-1-yl)phenyl)-2-oxopyridin-1(2H)-yl)-2-phenylethyl)-1H-benzo[d]imidazole-5-carboxylic acid,
methyl 2-(1-(4-(5-chloro-2-(1H-tetrazol-1-yl)phenyl)-2-oxopyridin-1(2H)-yl)-2-phenylethyl)-1H-benzo[d]imidazole-5-carboxylate,
2-(1-(4-(5-chloro-2-(1H-tetrazol-1-yl)phenyl)-2-oxopyridin-1(2H)-yl)-2-phenylethyl)-1H-benzo[d]imidazole-5-carboxylic acid,
4-(5-chloro-2-(1H-tetrazol-1-yl)phenyl)-1-(1-(5-fluoro-1H-benzo[d]imidazol-2-yl)-2-(4-fluorophenyl)ethyl)pyridin-2(1H)-one, (S)-methyl 2-(1-(4-(5-chloro-2-(1H-tetrazol-1-yl)phenyl)-2-oxopyridin-1(2H)-yl)-2-phenylethyl)-1H-benzo[d]imidazole-5-carboxylate, (S)-ethyl 2-(1-(4-(5-chloro-2-(1H-tetrazol-1-yl)phenyl)-2-oxopyridin-1(2H)-yl)-2-(4-fluorophenyl)ethyl)-1H-benzo[d]imidazole-5-carboxylate, (S)-2-(1-(4-(5-chloro-2-(1H-tetrazol-1-yl)phenyl)-2-oxopyridin-1(2H)-yl)-2-(4-fluorophenyl)ethyl)-1H-benzo[d]imidazole-5-carboxylic acid, (S)-4-(5-chloro-2-(1H-tetrazol-1-yl)phenyl)-1-(1-(5-fluoro-1H-benzo[d]imidazol-2-yl)-2-(4-fluorophenyl)ethyl)pyridin-2(1H)-one, (S)-4-(5-chloro-2-(1H-tetrazol-1-yl)phenyl)-1-(1-(5-bromo-1H-benzo[d]imidazol-2-yl)-2-(4-fluorophenyl)ethyl)pyridin-2(1H)-one, (R)-methyl 2-(1-(4-(5-chloro-2-(1H-tetrazol-1-yl)phenyl)-2-oxopyridin-1(2H)-yl)-2-phenylethyl)-1H-benzo[d]imidazole-5-carboxylate, (R)-2-(1-(4-(5-chloro-2-(1H-tetrazol-1-yl)phenyl)-2-oxopyridin-1(2H)-yl)-2-phenylethyl)-1H-benzo[d]imidazole-5-carboxylic acid, (R)-ethyl 2-(1-(4-(5-chloro-2-(1H-tetrazol-1-yl)phenyl)-2-oxopyridin-1(2H)-yl)-2-(4-fluorophenyl)ethyl)-1H-benzo[d]imidazole-5-carboxylate, (R)-4-(5-chloro-2-(1H-tetrazol-1-yl)phenyl)-1-(1-(5-fluoro-1H-benzo[d]imidazol-2-yl)-2-(4-fluorophenyl)ethyl)pyridin-2(1H)-one, (S)-diethyl (2-(1-(4-(5-chloro-2-(1H-tetrazol-1-yl)phenyl)-2-oxopyridin-1(2H)-yl)-2-(4-fluorophenyl)ethyl)-1H-benzo[d]imidazol-5-yl)phosphonate, (S)-(2-(1-(4-(5-chloro-2-(1H-tetrazol-1-yl)phenyl)-2-oxopyridin-1(2H)-yl)-2-(4-fluorophenyl)ethyl)-1H-benzo[d]imidazol-5-yl)phosphonic acid.

7. A composition for inhibiting thrombus formation in blood comprising a compound of claim 1 and a pharmaceutically acceptable carrier.

* * * * *